US009951330B2

(12) United States Patent
Crary et al.

(10) Patent No.: US 9,951,330 B2
(45) Date of Patent: Apr. 24, 2018

(54) MICRORNAS THAT SILENCE TAU EXPRESSION

(71) Applicant: The Trustees of Columbia University in the City of New York, New York, NY (US)

(72) Inventors: John Crary, Brooklyn, NY (US); Ismael Santa-Maria Perez, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/903,164

(22) PCT Filed: Jul. 11, 2014

(86) PCT No.: PCT/US2014/046373
§ 371 (c)(1),
(2) Date: Jan. 6, 2016

(87) PCT Pub. No.: WO2015/006705
PCT Pub. Date: Jan. 15, 2015

(65) Prior Publication Data
US 2017/0002348 A1 Jan. 5, 2017

Related U.S. Application Data

(60) Provisional application No. 61/844,977, filed on Jul. 11, 2013.

(51) Int. Cl.
C07H 21/02 (2006.01)
C12N 15/113 (2010.01)
C12Q 1/68 (2018.01)

(52) U.S. Cl.
CPC .......... *C12N 15/113* (2013.01); *C12Q 1/6883* (2013.01); *C12N 2310/141* (2013.01); *C12Q 2600/178* (2013.01)

(58) Field of Classification Search
CPC . A61K 31/713; C12N 15/113; C12N 2310/11
See application file for complete search history.

(56) References Cited

U.S. PATENT DOCUMENTS

| | | |
|---|---|---|
| 5,844,107 A | 12/1998 | Hanson et al. |
| 5,877,302 A | 3/1999 | Hanson et al. |
| 5,972,900 A | 10/1999 | Ferkol, Jr. et al. |
| 5,972,901 A | 10/1999 | Ferkol, Jr. et al. |
| 6,008,336 A | 12/1999 | Hanson et al. |
| 6,077,835 A | 6/2000 | Hanson et al. |
| 6,200,801 B1 | 3/2001 | Ferkol, Jr. et al. |
| 8,445,666 B2 | 5/2013 | Rigoutsos et al. |
| 2002/0150626 A1 | 10/2002 | Kohane et al. |
| 2003/0032615 A1 | 2/2003 | Felgner et al. |
| 2003/0203865 A1 | 10/2003 | Harvie et al. |
| 2004/0048787 A1 | 3/2004 | Cooper et al. |
| 2006/0185027 A1 | 8/2006 | Bartel et al. |
| 2007/0259827 A1 | 11/2007 | Aronin et al. |
| 2009/0317406 A1 | 12/2009 | Davies et al. |
| 2010/0179213 A1 | 7/2010 | Patrawala et al. |
| 2013/0116132 A1 | 5/2013 | Sharma et al. |

FOREIGN PATENT DOCUMENTS

| | | |
|---|---|---|
| WO | WO 2007/107789 | 9/2007 |
| WO | WO 2012/027558 | 3/2012 |

OTHER PUBLICATIONS

Abe and Bonini, "MicroRNAs and Neurodegeneration: Role and Impact", Jan. 2013. *Trends in Cell Biology* 23:30-36.
Ambros, "The functions of animal microRNAs", Sep. 16, 2004. *Nature* 431:350-355.
Anders and Huber, "Differential expression analysis for sequence count data", Oct. 2010. *Genome biology* 11:R106.
Aronov et al. "Identification of 3'UTR Region Implicated in Tau mRNA Stabilization in Neuronal Cells", Mar. 2, 1999. *Journal of Molecular Neuroscience* 12:131-145.
Aronov et al., "Axonal tau mRNA localization coincides with tau protein in living neuronal cells and depends on axonal targeting signal", Sep. 1, 2001. The Journal of Neuroscience: The Official Journal of the Society for Neuroscience 21:6577-6587.
Avila et al., "Role of Tau Protein in Both Physiological and Pathological Conditions" Apr. 2004. *Physiological Reviews* 84:361-384.
Baek et al., "The impact of microRNAs on protein Output", Sep. 4, 2008. *Nature* 455:64-71.
Bancher and Jellinger, "Neurofibrillary tangle predominant form of senile dementia of Alzheimer type: a rare subtype in very old subjects." Aug. 8, 1994, Acta Neuropathol 88: 565-570.
Bartel, "MicroRNA Target Recognition and Regulatory Functions", Jan. 23, 2009. *Cell* 136:215-233.
Barton et al., "Increased Tau Messenger RNA in Alzheimer's Disease Hippocampus", Sep. 1990. *The American Journal of Pathology* 137:497-502.
Bejarano et al., "A genome-wide transgenic resource for conditional expression of Drosophila microRNAs", May 14, 2012. *Development* 139:2821.
Beveridge and Cairns, "MicroRNA dysregulation in schizophrenia", (2012) *Neurobiology of Disease* 46:263-271. Available online Dec. 21, 2011.
Bilen et al. "MicroRNA Pathways Modulate Polyglutamine-Induced Neurodegeneration", Oct. 6, 2006. *Molecular Cell* 24:157-163.
Binder et al., "The Distribution of Tau in the Mammalian Central Nervous System," Oct. 1, 1985. *The Journal of Cell Biology* 101:1371-1378.
Borlongan, "Recent preclinical evidence advancing cell therapy for Alzheimer's disease", Jun. 27, 2012. *Experimental Neurology* 237:142-146.
Brewer et al., "Optimized Survival of Hippocampal Neurons in B27-Supplemented Neurobasalm™, a New Serum-free Medium Combination", May 14, 1993. *Journal of Neuroscience Research* 35:567-576.

(Continued)

*Primary Examiner* — Amy H Bowman
(74) *Attorney, Agent, or Firm* — Leason Ellis LLP

(57) ABSTRACT

This invention relates to the treatment and prevention of Alzheimer's disease (AD), tangle-predominant dementia (TPD) and other diseases associated with abnormal tau expression, e.g., tauopathies, using the 3'untranslated region (UTR) of the tau messenger RNA (mRNA) as a target, specifically using microRNAs that regulate the expression of tau. This invention is also in the field of screening for, identifying, and diagnosing such diseases. Specifically, this invention provides biomarkers for these diseases in the form of microRNAs.

10 Claims, 19 Drawing Sheets

(56) References Cited

OTHER PUBLICATIONS

Bullmann et al. "Expression of Embryonic Tau Protein Isoforms Persist During Adult Neurogenesis in the Hippocampus", 2007. *Hippocampus* 17:98-102. Published online Dec. 20, 2006.
Caceres et al. "The Effect of Tau Antisense Oligonucleotides on Neurite Formation of Cultured Cerebellar Macroneurons", Jun. 1991. T*he Journal of Neuroscience* 11:1515-1523.
Chin and Goldman, "Glial Inclusions in CNS Degenerative Diseases", May 1996. *Journal of Neuropathology and Experimental Neurology* 55:499-508.
Couratier et al., "Modulation of Tau Neuronal Expression Induced by NMDA, non-NMDA and Metabotropic Glutamate Receptor Agonists," Apr. 1995. *Neurodegeneration* 4:33-41.
Dai et al. "Exploiting Drosophila Genetics to Understand MicroRNA Function and Regulation", Dec. 2012. *Current Topics in Developmental Biology* 99:201.
Dawson et al. "Loss of Tau Elicits Axonal Degeneration in a Mouse Model of Alzheimer's Disease", Apr. 29, 2010. *Neuroscience* 169:516-531.
Dickson et al. "Alternative Polyadenylation and miR-34 Family Members Regulate Tau Expression", Dec. 2013. *Journal of Neurochemistry* 127:739 (2013).
Dickson (Aug. 25, 2009) "Neuropathology of non-Alzheimer degenerative disorders", International Journal of Clinical and Experimental Pathology 3 : 1 -23.
Dotti et al., "The Expression and Distribution of the Microtubule-Associated Proteins Tau and Microtubule-Associated Protein 2 in Hippocampal Neurons in the Rat in Situ and in Cell Culture," Feb. 17, 1987. *Neuroscience* 23:121-130.
Drubin and Hirokawa, "Cytoskeleton", 1998. *Current Opinion in Cell Biology* 10:13-15.
Drubin et al., "Nerve Growth Factor-induced Neurite Outgrowth in PC12 Cells Involves the Coordinate Induction of Microtubule Assembly and Assembly-promoting Factors", Nov. 1, 1985. *The Journal of Cell Biology* 101:1799-1807.
Drubin et al., "Regulation of Microtubule Protein Levels during Cellular Morphogenesis in Nerve Growth Factor-treated PC12 Cells," May 1, 1988. *The Journal of Cell Biology* 106:1583-1591.
Eacker et al., "Understanding microRNAs in Neurodegeneration," Dec. 2009. *Nature Reviews. Neuroscience* 10:837-841.
Ebert and Sharp, "MicroRNA sponges: Progress and possibilities", Nov. 2010. *RNA* 16:2043.
Ebneth et al., "Overexpression of Tau Protein Inhibits Kinesin-dependent Trafficking of Vesicles, Mitochondria, and Endoplasmic Reticulum: Implications for Alzheimer's Disease", Nov. 2, 1998. *The Journal of Cell Biology* 143:777-794.
Esclaire et al., "Glutamate Toxicity Enhances Tau Gene Expression in Neuronal Cultures", Mar. 20, 1997. *Journal of Neuroscience Research* 49:309-318.
Eulalio et al., "Getting to the Root of miRNA-Mediated Gene Silencing", Jan. 11, 2008. *Cell* 132:9-14.
Farias et al., "Tubulin, Actin, and Tau Protein Interactions and the Study of their Macromolecular Asseblies", Jan. 8, 2002. *Journal of Cellular Biochemistry* 85:315-324.
Flynt and Lai, "Biological principles of microRNA-mediated regulation: shared themes amid diversity", Nov. 2008. *Nature Reviews. Genetics* 9:831-842.
Friedman et al. Most mammalian mRNAs are conserved targets of microRNAs, (2009) *Genome Research* 19:92-105. Published online Oct. 27, 2008.
Fulga et al. "Abnormal bundling and accumulation of F-actin mediates tau-induced neuronal degeneration in vivo", Feb. 2007. *Nature Cell Biology* 9:139-148.
Garcia et al., "Weak Seed-Pairing Stability and High Target-Site Abundance Decrease the Proficiency of *lsy-6* and Other miRNAs", Sep. 11, 2011. *Nature Structural and Molecular Biology* 18:1139-1146.

Gascon and Gao, "Cause or effect: misregulation of microRNA pathways in neurodegeneration", Apr. 2012. *Frontiers in Neuroscience* 6:48.
Gasparini et al. (Jun. 2007) "Frontotemporal dementia with tau pathology", Neurodegener Dis 4: 236-253.
Gentleman et al. "Bioconductor: open software development for computational biology and bioinformatics", Sep. 15, 2004. *Genome Biology* 5:R80.
Gomez-Ramos et al., "Extracellular tau is toxic to neuronal cells", Aug. 8, 2006. *FEBS Letters* 580:4842-4850.
Gong et al., "Post-translational modifications of tau protein in Alzheimer's disease", (2005) *Journal of Neural Transmission* 112:813-838. Published online Oct. 27, 2004.
Grau and Greene, "Use of PC12 Cells and Rat Superior Cervical Ganglion Sympathetic Neurons as Models for Neuroprotective Assays Relevant to Parkinson's Disease", 2012. *Methods in Molecular Biology* 846:201-211. Available in PMC Jun. 11, 2013.
Greene and Tischler, "Establishment of a noradrenergic clonal line of rat adrenal pheochromocytoma cells which respond to nerve growth factor", Jul. 1976. *Proceedings of the National Academy of Sciences of the United States of America* 73:2424-2428.
Griffiths-Jones, "The microRNA Registry", 2004. *Nucleic Acids Research* 32:D109-111. Accepted Sep. 3, 2003.
Grimson et al., "MicroRNA Targeting Specificity in Mammals: Determinants Beyond Seed Pairing", Jul. 6, 2007. *Molecular Cell* 27:91-105.
Guo and Lee, "Seeding of Normal Tau by Pathological Tau Conformers Drives Pathogenesis of Alzheimer-like Tangles", Mar. 3, 2011. *The Journal of Biological Chemistry* 286:15317-15331.
Hafner et al., "RNA-ligase-dependent biases in miRNA representation in deep-sequenced small RNA cDNA libraries", Sep. 2011. *RNA* 17:1697-1712.
Hamada et al., "MicroRNA expression profiling of NGF-treated PC12 cells revealed a critical role for miR-221 in neuronal differentiation", Mar. 24, 2012. *Neurochemistry International* 60:743-750.
He et al., "The proline-rich domain of tau plays a role in interactions with actin", Nov. 8, 2009. *BMC Cell Biology* 10:81.
Hebert et al., "Loss of microRNA cluster miR-29a/b-1 in sporadic Alzheimer's disease correlates with increased BACE1/beta-secretase expression", Apr. 29, 2008. *Proceedings of the National Academy of Sciences of the United States of America* 105:6415-6420.
Hebert et al., "Genetic ablation of Dicer in adult forebrain neurons results in abnormal tau hyperphosphorylation and neurodegeneration", Jul. 21, 2010. *Human Molecular Genetics* 19:3959-3969.
Heidary and Fortini, "Identification and characterization of the *Drosophila tau* homolog", Jul. 2, 2001. M*ech Dev* 108:171.
Hong et al., "Essential Role of Tau Phosphorylation in Adult Hippocampal Neurogenesis", (2010) *Hippocampus* 20:1339-1349. Published Online Oct. 8, 2009.
Hutton et al. (Jun. 18, 1998) Association of missense and 5'-splice-site mutations in tau with the inherited dementia FTDP-17. Nature 393 : 702-705.
Jackson et al., "Human Wild-Type Tau Interacts with *wingless* Pathway Components and Produces Neurofibrillary Pathology in *Drosophila*", May 16, 2002. *Neuron* 4(4):509-19.
Kim et al. "A microRNA feedback circuit in midbrain dopamine neurons", Aug. 31, 2007. *Science* 317:1220-1224.
Kosik, "The neuronal microRNA system", Dec. 2006. N*ature Reviews. Neuroscience* 7:911-920.
Kotani et al. "Calmodulin Inhibits Interaction of Actin with MAP2 and Tau, Two Major Microtubule-associated Proteins", Sep. 5, 1985. *The Journal of Biological Chemistry* 260:10779-10783.
Kozomara and Griffiths-Jones, "miRBase: integrating microRNA annotation and deep-sequencing data", 2011. *Nucleic Acids Research* 39:D152-157. Published online Oct. 30, 2010.
Kuersten and Goodwin, "The Power of the 3' UTR: Translational Control and Development", Aug. 2003. *Nature Reviews. Genetics* 4:626-637.
Lau et al. "Alteration of the microRNA network during the progression of Alzheimer's disease", Jul. 26, 2013. *EMBO Mol Med* 5:1613.

(56) References Cited

OTHER PUBLICATIONS

Le et al. "Multiple mechanisms of extracellular tau spreading in a non-transgenic tauopathy model", Nov. 30, 2012. *American Journal of Neurodegenerative Disease* 1:316-333.

Lee et al., "The *C. elegans* Heterochronic Gene *lin-4* Encodes Small RNAs with Antisense Complementarity to *lin-14*", Dec. 3, 1993. *Cell* 75:843-854.

Lewis et al. "Conserved Seed Pairing, Often Flanked by Adenosines, Indicates that Thousands of Human Genes are MicroRNA Targets", Jan. 14, 2005. *Cell* 120:15-20.

Lippens et al. "Towards understanding the phosphorylation code of tau" Feb. 28, 2012. *Biochemical Society Transactions* 40:698-703.

Loya et al., "Transgenic microRNA inhibition with spatiotemporal specificity in intact organisms", Dec. 2009. *Nature Methods* 6:897.

Maas et al., "Interaction of Tau with the Neural Membrane Cortex Is Regulated by Phosphorylation at Sites That Are Modified in Paired Helical Filaments", Mar. 16, 2000 *The Journal of Biological Chemistry* 275:15733-15740.

Mandell and Banker, "The Microtubule Cytoskeleton and the Development of Neuronal Polarity", May-Jun 1995. *Neurobiology of Aging* 16:229-238.

Mandelkow and Mandelkow, "Biochemistry and Cell Biology of Tau Protein in Neurofibrillary Degeneration", Mar. 20, 2012. *Cold Spring Harbor Perspectives in Medicine* 2:a006247.

Matoulkova et al. "The role of the 3' untranslated region in posttranscriptional regulation of protein expression in mammalian cells", May 1, 2012. *RNA Biology* 9:563-576.

Mazumder et al., "Translational control by the 3'-UTR: the ends specify the means", Feb. 2003. *Trends in Biochemical Sciences* 28:91-98.

Morris et al. "The Many Faces of Tau", May 12, 2011. *Neuron* 70:410-426.

Nunez-Iglesias et al. "Joint Genome-Wide Profiling of miRNA and mRNA Expression in Alzheimer's Disease Cortex Reveals Altered miRNA Regulation", Feb. 1, 2010. *PLoS One* 5:e8898.

Packer et al., "The Bifunctional microRNA miR-9/miR-9* Regulates REST and CoREST and Is Downregulated in Huntington's Disease", Dec. 31, 2008. *The Journal of Neuroscience* 28:14341-14346.

Perron and Provost, "Protein components of the microRNA pathway and human Diseases," 2009. *Methods in Molecular Biology* 487:369-385. Available in PMC Jul. 13, 2010.

Phelan and Larson, ""Successful Aging"—Where Next?", Jul. 2002. *Journal of the American Geriatrics Society* 50:1306-1308.

Pittman et al., "Untangling the tau gene association with neurodegenerative disorders", Jul. 25, 2006. *Human Molecular Genetics* 15 Spec No. 2:R188-195.

Rademakers et al., "Common variation in the miR-659 binding-site of *GRN* is a major risk factor for TDP43-positive frontotemporal dementia", Aug. 20, 2008. *Human Molecular Genetics* 17:3631-3642.

Roberson et al., "Reducing Endogenous Tau Ameliorates Amyloid b—Induced Deficits in an Alzheimer's Disease Mouse Model," May 4, 2007. *Science* 316:750-754.

Roberson et al., "Amyloid-β/Fyn—Induced Synaptic, Network, and Cognitive Impairments Depend on Tau Levels in Multiple Mouse Models of Alzheimer's Disease", Jan. 12, 2011. *The Journal of Neuroscience* 31:700-711.

Rowe and Kahn, "Human Aging: Usual and Successful", Jul. 10, 1987. *Science* 237:143-149.

Santa-Maria et al., "The MAPT H1 haplotype is associated with tangle-predominant Dementia", Jul. 17, 2012 (1). *Acta Neuropathologica* 124:693-704.

Santa-Maria et al., "Paired Helical Filaments from Alzheimer Disease Brain Induce Intracellular Accumulation of Tau Protein in Aggresomes", Jun. 8, 2012 (2). *The Journal of Biological Chemistry* 287:20522-20533.

Santacruz et al., "Tau Suppression in a Neurodegenerative Mouse Model Improves Memory Function", Jul. 15, 2005. *Science* 309:476-481.

Sato et al., "A Tau-tubulin kinase 1 (TTBK1), a neuron-specific tau kinase candidate, is involved in tau phosphorylation and aggregation", Oct. 2006 *Journal of Neurochemistry* 98(5):1573-84.

Saugstad, "MicroRNAs as effectors of brain function with roles in ischemia and injury, neuroprotection, and neurodegeneration", Jul. 7, 2010. *Journal of Cerebral Blood Flow and Metabolism* 30:1564-1576.

Schaefer et al., "Cerebellar neurodegeneration in the absence of microRNAs", Jul. 2, 2007. *The Journal of Experimental Medicine* 204:1553-1558.

Schonrock et al., "MicroRNA networks surrounding APP and amyloid-β metabolism—Implications for Alzheimer's disease", (2012) *Experimental Neurology* 235:447-454. Available online Nov. 16, 2011.

Schonrock and Gotz, "Decoding the non-coding RNAs in Alzheimer's disease", Sep. 6, 2012. *Cellular and Molecular Life Sciences* 69:3543-3559.

Selbach et al., "Widespread changes in protein synthesis induced by microRNAs", Sep. 4, 2008. *Nature* 455:58-63.

Sempere et al. "Expression profiling of mammalian microRNAs uncovers a subset of brain-expressed microRNAs with possible roles in murine and human neuronal differentiation", Published Feb. 16, 2004. *Genome Biology* 5:R13.

Silver et al., "Functional screening identifies miR-315 as a potent activator of Wingless signaling", Sep. 20, 2007. *Proc Natl Acad Sci U S A* 104:18151.

Sindou et al., "A dose-dependent increase of Tau immunoataining is produced by glutamate toxicity in primary neuronal cultures", (1992) *Brain Research* 572:242-246. Accepted Oct. 29, 1991.

Spencer et al. "Unraveling 50-year-old clues linking neurodegeneration and cancer to cycad toxins: are microRNAs common mediators?", Sep. 2012. *Frontiers in Genetics* 3:192.

Terwel et al., "Axonal Transport, Tau Protein, and Neurodegeneration in Alzheimer's Disease", May 22, 2002. *Neuromolecular medicine* 2:151-165.

Thinakaren and Koo, "Amyloid Precursor Protein Trafficking, Processing, and Function", Jul. 23, 2008, *The Journal of Biological Chemistry*, 283:29615-29619.

Ulrich et al. (Oct. 14, 1992) Abundant neurofibrillary tangles without senile plaques in a subset of patients with senile dementia. Neurodegeneration 1 : 257-284.

Vandrovcova et al., "Disentangling the role of the tau gene locus in sporadic tauopathies", Feb. 4, 2010. Current Alzheimer Research: 7, 726-734.

Wade-Martins et al. "The MAPT locus—a genetic paradigm in disease susceptibility", Sep. 2012, *Nature Reviews. Neurology* 8:477-478.

Wang et al., "A Modular Toolset for Recombination Transgenesis and Neurogenetic Analysis of Drosophila", Jul. 2012. *PLoS One* 7: e42102.

Wang and Mandelkow, "Degradation of tau protein by autophagy and proteasomal pathways", Mar. 8, 2012. 40:644-652.

Wang et al., "The Expression of MicroRNA miR-107 Decreases Early in Alzheimer's Disease and May Accelerate Disease Progression through Regulation of β-Site Amyloid Precursor Protein-Cleaving Enzyme 1", Jan. 30, 2008. *Journal of Neuroscience* 28:1213-1223.

Wang et al. "Patterns of microRNA expression in normal and early Alzheimer's disease human temporal cortex: white matter versus gray matter", Oct. 10, 2010. *Acta Neuropathol* 121:193-205.

Weingarten et al. "A Protein Factor Essential for Microtubule Assembly", May 1975. *Proceedings of the National Academy of Sciences of the United States of America* 72:1858-1862.

Williams et al. "Tau and Tau Reporters Disrupt Central Projections of Sensory Neurons in *Drosophila*", Sep. 1, 2000. *Journal of Comparative Neurology.* 428(4):630-40.

Wittmann et al., "Tauopathy in *Drosophila*:Neurodegeneration Without Neurofibrillary Tangles", Jul. 27, 2001. *Science* 293(5530):711-4.

Yamada et al., "Senile dementia of the neurofibrillary tangle type: a comparison with Alzheimer's disease", (2001) Dement Geriatr Cogn Disord 12: 117-126. Accepted Jun. 19, 2000.

(56) References Cited

OTHER PUBLICATIONS

Zhao et al., "MicroRNA-Mediated Control of Oligodendrocyte Differentiation", Mar. 11, 2010. *Neuron* 65:612-626.

Zhang and Verbeek, "Comparison and Integration of Target Prediction Algorithms for microRNA Studies", Mar. 25, 2010. *Journal of Integrative Bioinformatics* 7.

Santa-Maria et al., "MicroRNA profiling in tangle-only dementia", Annual Meeting of the Neuroscience-Society; New Orleans, LA, USA; Oct. 13-17, 2012, Society for Neuroscience Abstract Viewer and Itinerary Planner, US vol. 42 Jan. 1, 2012 (Jan. 1, 2012), pp. 1-4, XP008182531, Retrieved from the Internet: URL:http://www.abstractsonline.com/Plan/ViewAbstract.aspx?sKey=53dl6b96-c6fl-4185-aO32-2bf33ce602e9&cKey=a09f0301-3c8f-4b29-954c-399e6d62b178&mKey=%7b70007181-01C9-4DE9-AOA2-EEBFA14CD9F1%7d * the whole document *.

P. Y. Smith et al: "MicroRNA-132 loss is associated with tau exon 10 inclusion in progressive supranuclear palsy", Human Molecular Genetics, vol. 20, No. 20, Aug. 1, 2011 (Aug. 1, 2011), pp. 4016-4024, XP055329133, gb ISSN : 0964-6906, DOI : 10.1093/hmg/ddr330 *p. 4017, right-hand column, line 7-line 9; figures 1A, 1B *.

Pierre Lau et al: "Alteration of the microRNA network during the progression of Alzheimer's disease", EMBO Molecular Medicine, vol. 5, No. 10, Oct. 1, 2013 (Oct. 1, 2013), pp. 1613-1634, XP055239373, Weinheim ISSN: 1757-4676, DOI: 10.1002/emmm.201201974 * figure 8 *.

Wu Hao et al: "Regulation of microtubule-associated protein tau (MAPT) by miR-34c-5p determines the chemosensitivity of gastric cancer to paclitaxel", Cancer Chemotherapy and Pharmacology, Springer Verlag, Berlin, vol. 71, No. 5, Feb. 20, 2013 (Feb. 20, 2013), pp. 1159-1171, XP035339887, ISSN: 0344-5704, DOI: 10.1007/S00280-013-2108-Y [retrieved on Feb. 20, 2013]* the whole document *.

Sebastien S. Hebert et al: "MicroRNAs and the Regulation of Tau Metabolism", International Journal of Alzheimer's Disease, vol. 10, No. 4, Jan. 1, 2012 (Jan. 1, 2012), pp. 333-336, XP055227407, ISSN: 2090-8024 , DOI: 10.1101/gr.118638.110.

Ismael Santa-Maria et al: "Dysregulation of microRNA-219 promotes neurodegeneration through post-transcriptional regulation of tau", Journal of Clinical Investigation, vol. 125, No. 2, Jan. 9, 2015 (Jan. 9, 2015), pp. 681-686, XP055326248, US, ISSN: 0021-9738, DOI: 10 .1172/JCI78421.

Jinwal et al., "Reconstructing the Hsp90/Tau Machine", 2013 *Curr Enzym Inhib.* 9(1):41-5. Accepted Jun. 30, 2012.

Figure 5A
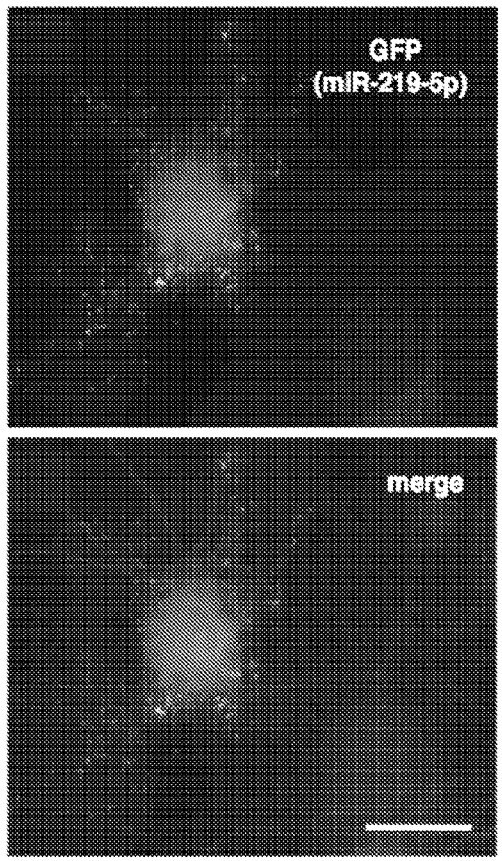
Figure 5B
Figure 5C
Figure 5D
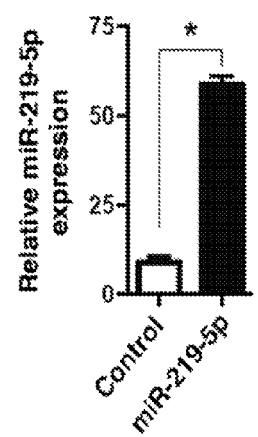

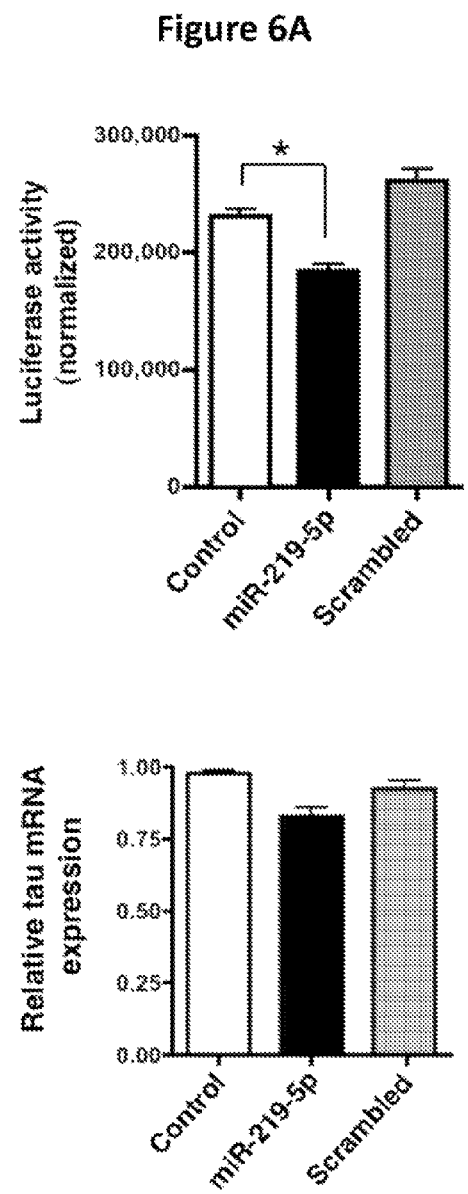
Figure 6A
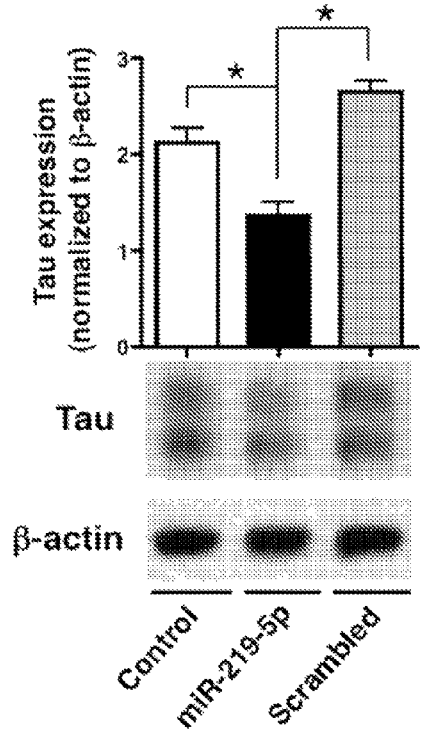
Figure 6B
Figure 6C

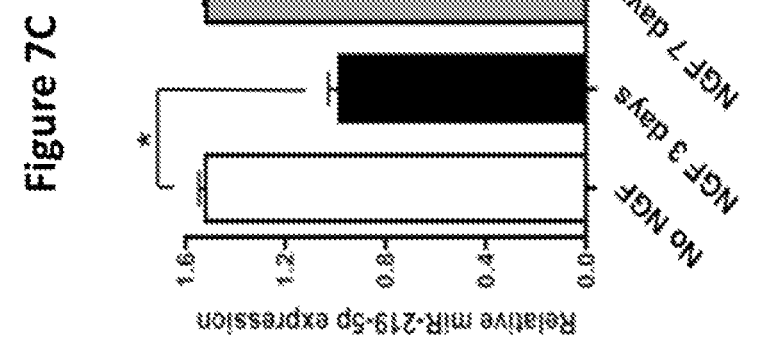
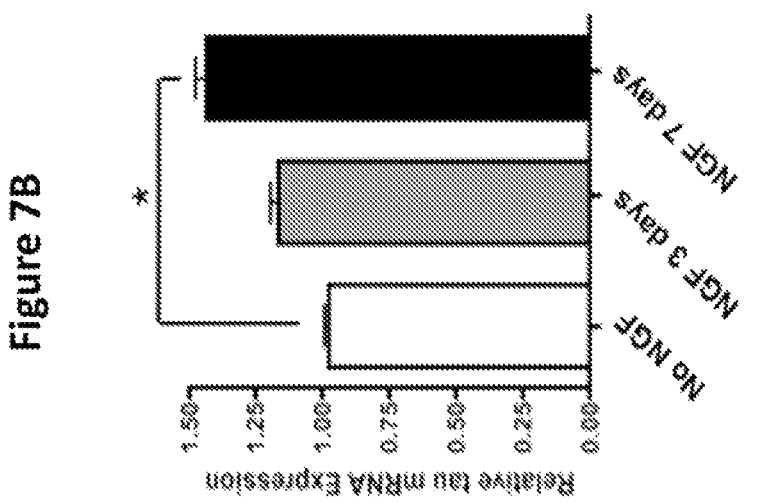
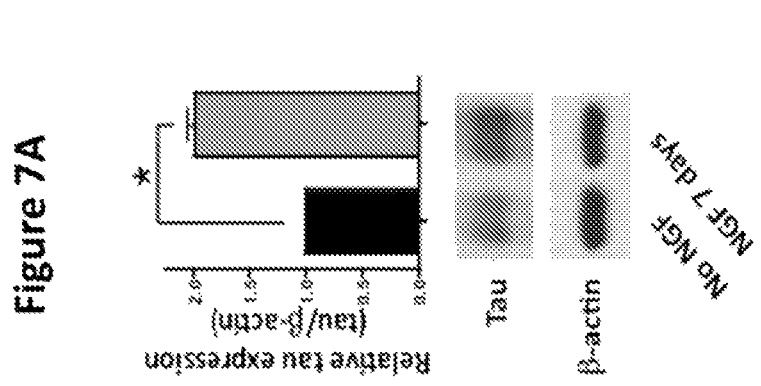

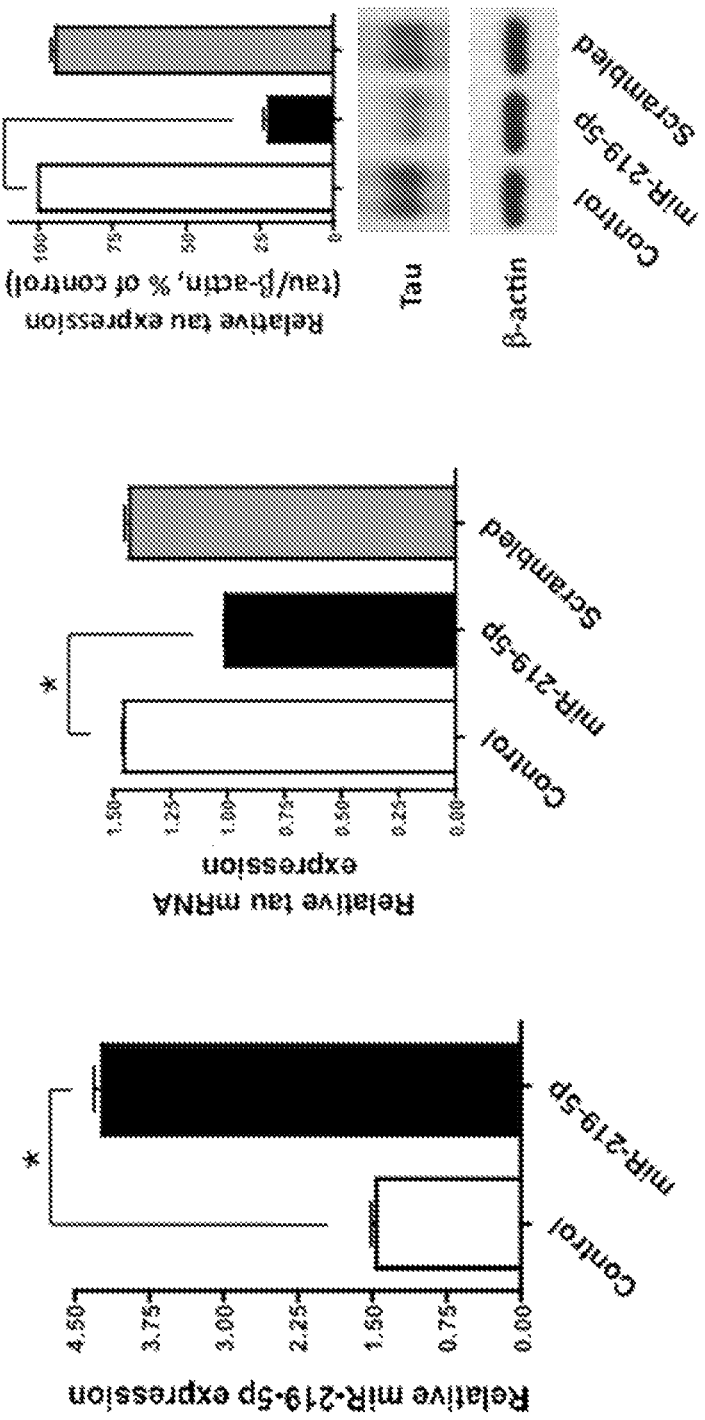

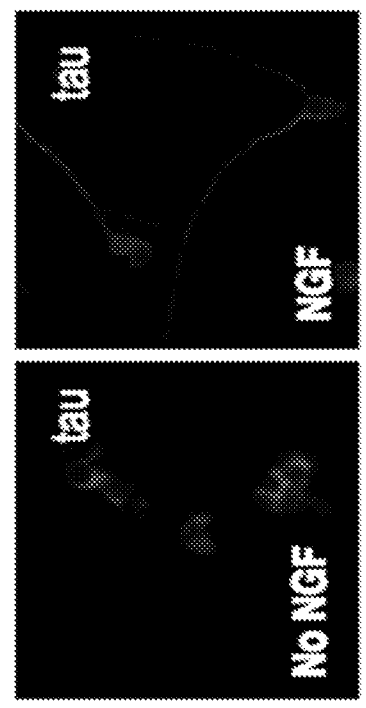

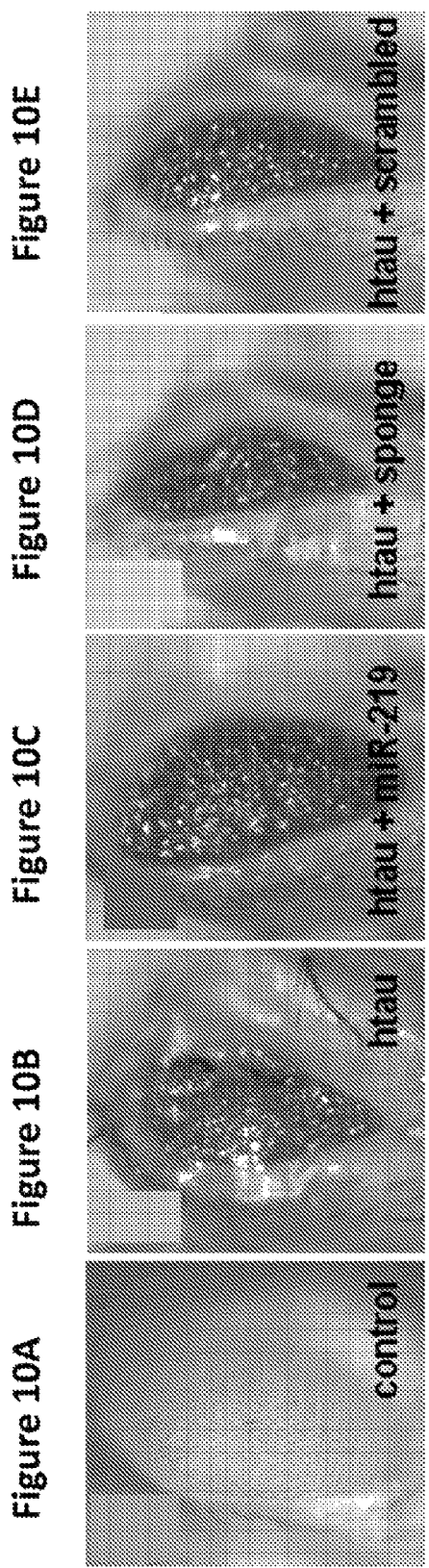

SEQUENCE LISTING

<160> NUMBER OF SEQ ID NOS: 14

<210> SEQ ID NO 1

```
<211> LENGTH: 23
<212> TYPE: RNA
<213> ORGANISM: Homo sapiens

<400> SEQUENCE: 1
ugauugucca aacgcaauuc uug                                              23

<210> SEQ ID NO 2
<211> LENGTH: 22
<212> TYPE: RNA
<213> ORGANISM: Homo sapiens

<400> SEQUENCE: 2
agaggcuggc cgugaugaau uc                                               22

<210> SEQ ID NO 3
<211> LENGTH: 23
<212> TYPE: RNA
<213> ORGANISM: Homo sapiens

<400> SEQUENCE: 3
aacauucauu guugucggug ggu                                              23

<210> SEQ ID NO 4
<211> LENGTH: 4433
<212> TYPE: DNA
<213> ORGANISM: Homo sapiens

<400> SEQUENCE: 4
accctccctc ccttcctctt cttgcagatt gaaacccaca agctgacctt ccgcgagaac        60
gccaaagcca agacagacca cggggcggag atcgtgtaca agtcgccagt ggtgtctggg       120
gacacgtctc cacggcatct cagcaatgtc tcctccaccg gcagcatcga catggtagac       180 tcgcccccagc tcgccacgct agctgacgag gtgtctgcct ccctggccaa gcagggtttg       240
tgatcaggcc cctggggcgg tcaataattg tggagaggag agaatgagag agtgtggaaa       300
aaaaaagaat aatgacccgg ccccccgccct ctgcccccag ctgctcctcg cagttcggtt       360
aattggttaa tcacttaacc tgcttttgtc actcggcttt ggctcgggac ttcaaaatca       420
gtgatgggag taagagcaaa tttcatcttt ccaaattgat gggtgggcta gtaataaaat       480
atttaaaaaa aaacattcaa aaacatggcc acatccaaca tttcctcagg caattccttt       540
tgattctttt ttcttccccc tccatgtaga agagggagaa ggagaggctc tgaaagctgc       600
ttctggggga tttcaaggga ctgggggtgc aaccacctc tggccctgtt gtggggtgt       660 cacagaggca gtggcagcaa caaaggattt gaaacttggt gtgttcgtgg agccacaggc       720
agacgatgtc aaccttgtgt gagtgtgacg ggggttgggg tggggcggga ggccacgggg       780
gaggccgagg caggggctgg gcagagggga gaggaagcac aagaagtggg agtgggagag       840
gaagccacgt gctggagagt agacatcccc ctccttgccg ctgggagagc caaggcctat       900
gccacctgca gcgtctgagc ggccgcctgt ccttggtggc cggggtggg ggcctgctgt        960 gggtcagtgt gccacccctct gcagggcagc ctgtgggaga agggacagcg ggtaaaaaga      1020
gaaggcaagc tggcaggagg gtggcacttc gtggatgacc tccttagaaa agactgacct      1080
tgatgtcttg agagcgctgg cctcttcctc cctccctgca gggtagggg cctgagttga       1140 ggggcttccc tctgctccac agaaaccctg ttttattgag ttctgaaggt tggaactgct      1200
gccatgattt tggccacttt gcagacctgg gactttaggg ctaaccagtt ctctttgtaa      1260
ggacttgtgc ctcttgggag acgtccaccc gtttccaagc ctgggccact ggcatctctg      1320
```

```
gagtgtgtgg gggtctggga ggcaggtccc gagccccctg tccttcccac ggccactgca    1380
gtcaccccgt ctgcgccgct gtgctgttgt ctgccgtgag agcccaatca ctgcctatac    1440
ccctcatcac acgtcacaat gtcccgaatt cccagcctca ccaccccttc tcagtaatga    1500
ccctggttgg ttgcaggagg tacctactcc atactgaggg tgaaattaag ggaaggcaaa    1560
gtccaggcac aagagtggga ccccagcctc tcactctcag ttccactcat ccaactggga    1620
ccctcaccac gaatctcatg atctgattcg gttccctgtc tcctcctccc gtcacagatg    1680
tgagccaggg cactgctcag ctgtgaccct aggtgtttct gccttgttga catggagaga    1740
gccctttccc ctgagaaggc ctggcccctt cctgtgctga gcccacagca gcaggctggg    1800
tgtcttggtt gtcagtggtg gcaccaggat ggaagggcaa ggcacccagg gcaggcccac    1860
agtcccgctg tcccccactt gcaccctagc ttgtagctgc caacctccca gacagcccag    1920
cccgctgctc agctccacat gcatagtatc agccctccac acccgacaaa ggggaacaca    1980
cccccttgga aatggttctt ttcccccagt cccagctgga agccatgctg tctgttctgc    2040
tggagcagct gaacatatac atagatgttg ccctgccctc cccatctgca ccctgttgag    2100
ttgtagttgg atttgtctgt ttatgcttgg attcaccaga gtgactatga tagtgaaaag    2160
aaaaaaaaaa aaaaaaaagg acgcatgtat cttgaaatgc ttgtaaagag gtttctaacc    2220
caccctcacg aggtgtctct cacccccaca ctgggactcg tgtggcctgt gtggtgccac    2280
cctgctgggg cctcccaagt tttgaaaggc tttcctcagc acctgggacc caacagagac    2340
cagcttctag cagctaagga ggccgttcag ctgtgacgaa ggcctgaagc acaggattag    2400
gactgaagcg atgatgtccc cttccctact tccccttggg gctccctgtg tcagggcaca    2460
gactaggtct tgtggctggt ctggcttgcg gcgcgaggat ggttctctct ggtcatagcc    2520
cgaagtctca tggcagtccc aaaggaggct tacaactcct gcatcacaag aaaaaggaag    2580
ccactgccag ctgggggat ctgcagctcc cagaagctcc gtgagcctca gccacccctc    2640
agactgggtt cctctccaag ctcgccctct ggaggggcag cgcagcctcc caccaagggc    2700
cctgcgacca cagcagggat tgggatgaat tgcctgtcct ggatctgctc tagaggccca    2760
agctgcctgc ctgaggaagg atgacttgac aagtcaggag acactgttcc caaagccttg    2820
accagagcac ctcagcccgc tgaccttgca caaactccat ctgctgccat gagaaaaggg    2880
aagccgcctt tgcaaaacat tgctgcctaa agaaactcag cagcctcagg cccaattctg    2940
ccacttctgg tttgggtaca gttaaaggca accctgaggg acttggcagt agaaatccag    3000
ggcctcccct ggggctggca gcttcgtgtg cagctagagc tttacctgaa aggaagtctc    3060
tgggcccaga actctccacc aagagcctcc ctgccgttcg ctgagtccca gcaattctcc    3120
taagttgaag ggatctgaga aggagaagga aatgtgggt agatttggtg gtggttagag    3180
atatgccccc ctcattactg ccaacagttt cggctgcatt tcttcacgca cctcggttcc    3240
tcttcctgaa gttcttgtgc cctgctcttc agcaccatgg gccttcttat acggaaggct    3300
ctgggatctc ccccttgtgg ggcaggctct tggggccagc ctaagatcat ggtttagggt    3360
gatcagtgct ggcagataaa ttgaaaaggc acgctggctt tgatcttaa atgaggacaa    3420 tcccccagg gctgggcact cctcccctcc cctcacttct cccacctgca gagccagtgt    3480
ccttgggtgg gctagatagg atatactgta tgccggctcc ttcaagctgc tgactcactt    3540
tatcaatagt tccattaaa ttgacttcag tggtgagact gtatcctgtt tgctattgct    3600
tgttgtgcta tgggggagg gggaggaat gtgtaagata gttaacatgg gcaaagggag    3660
```

| | |
|---|---|
| atcttggggt gcagcactta aactgcctcg taacccttttt catgatttca accacatttg | 3720 |
| ctagagggag ggagcagcca cggagttaga ggcccttggg gtttctcttt tccactgaca | 3780 |
| ggctttccca ggcagctggc tagttcattc cctccccagc caggtgcagg cgtaggaata | 3840 |
| tggacatctg gttgctttgg cctgctgccc tctttcaggg gtcctaagcc cacaatcatg | 3900 |
| cctccctaag accttggcat ccttccctct aagccgttgg cacctctgtg ccacctctca | 3960 |
| cactggctcc agacacacag cctgtgcttt tggagctgag atcactcgct tcaccctcct | 4020 |
| catctttgtt ctccaagtaa agccacgagg tcggggcgag ggcagaggtg atcacctgcg | 4080 |
| tgtcccatct acagacctgc agcttcataa aacttctgat ttctcttcag ctttgaaaag | 4140 |
| ggttaccctg ggcactggcc tagagcctca cctcctaata gacttagccc catgagtttg | 4200 |
| ccatgttgag caggactatt tctggcactt gcaagtccca tgatttcttc ggtaattctg | 4260 |
| agggtggggg gagggacatg aaatcatctt agcttagctt tctgtctgtg aatgtctata | 4320 |
| tagtgtattg tgtgttttaa caaatgattt acactgactg ttgctgtaaa agtgaatttg | 4380 |
| gaaataaagt tattactctg attaaataag gtctccattc atggattcca agg | 4433 |

<210> SEQ ID NO 5
<211> LENGTH: 4503
<212> TYPE: DNA
<213> ORGANISM: Homo sapiens

<400> SEQUENCE: 5

| | |
|---|---|
| ctggcacttc atctcaccct ccctcccttc ctcttcttgc agattgaaac ccacaagctg | 60 |
| accttccgcg agaacgccaa agccaagaca gaccacgggg cggagatcgt gtacaagtcg | 120 |
| ccagtggtgt ctggggacac gtctccacgg catctcagca atgtctcctc caccggcagc | 180 |
| atcgacatgg tagactcgcc ccagctcgcc acgctagctg acgaggtgtc tgcctccctg | 240 |
| gccaagcagg gtttgtgatc aggcccctgg ggcggtcaat aatcgtggag aggagagaat | 300 |
| gagagagtgt ggaaaaaaaa agaataatga cccggccccc gccctctgcc cccagctgct | 360 |
| cctcgcagtt cggttaattg gttaatcact taacctgctt ttgtcactcg gctttggctc | 420 |
| gggacttcaa aatcagtgat gggagtaaga gcaaatttca tctttccaaa ttgatgggtg | 480 |
| ggctagtaat aaaatatttt aaaaaaaaac attcaaaaac atggccacat ccaacatttc | 540 |
| ctcaggcaat tcctttgat tcttttttct tccccctcc atgtagaaga gggggaagga | 600 |
| gaggctctga aagctgcttc tgggggattt caagggactg ggggtgccaa ccacctctgg | 660 |
| ccctgttgtg ggggtgtcac agaggcagtg gcagcaacaa aggatttgaa acttggtgtg | 720 |
| ttcgtggagc cacaggcaga cgatgtcaac cttgtgtgag tgtgacgggg gttggggtgg | 780 |
| ggcgggaggc cacgggggag gccgaggcag ggggctggca gaggggagag gaagcacaag | 840 |
| aagtgggagt gggagaggaa gccacgtgct ggagagtaga catccccctc cttgccgctg | 900 |
| ggagagccaa ggcctatgcc acctgcagcg tctgagcggc cgcctgtcct tggtggccgg | 960 |
| gggtggggc ctgctgtggg tcagtgtgcc accctctgca gggcagcctg tgggagaagg | 1020 |
| gacagcgggt aaaaagagaa ggcaagctgg caggagggtg gcacttcgtg gatgacctcc | 1080 |
| ttagaaaaga ctgaccttga tgtcttgaga gcgctggcct cttcctccct ccctgcaggg | 1140 |
| taggggcct gagttgaggg gcttccctct ctgctccaca gaaaccctgt tttattgagt | 1200 |
| tctgaaggtt ggaactgctg ccatgatttt ggccactttg cagacctggg actttagggc | 1260 |
| taaccagttc tctttgtaag gacttgtgcc tcttgggaga cgtccacccg tttccaagcc | 1320 |
| tgggccaccg gcatctctgg agtgtgtggg ggtctgggag gcgggtcccg agcccctgt | 1380 |

```
ccttcccacg gccactgcag tcacccctgt ctgccccgct gtgctgttgt ctgccgtgag    1440
agcccaatca ctgcctatac ccctcatcac gtcacaatgt cccgaattcc cagcctcacc    1500
accccttctc agtaatgacc ctggttggtt gcaggaggta cctactccat actgagggtg    1560
aaattaaggg aaggcaaagt ccaggcacca gagtgggacc ccagcctctc actctcagtt    1620
ccactcatcc aactgggacc ctcaccacga atctcacgat ctgattcggt tccctgtctc    1680
ctcctcccgt cacagatgtg agccagggca ctgctcagct gtgaccctag gtgtttctgc    1740
cttgttgaca tggagagagc cctttcccct gagaaggcct ggccccttcc tgtgctgagc    1800
ccacagcagc aggctgggtg tcttggttgt cagtggtggc accaggatgg aagggcaagg    1860
cacccagggc aggcccacag tcccgctgtc ccccacttgc accctagctt gtagctgcca    1920
acctcccaga cagcccagcc cgctgctcag ctccacatgc atagtatcag ccctccacac    1980
ccgacaaagg ggaacacacc cccttggaaa tggttctttc cccccagtcc cagctggaag    2040
ccatgctgtc tgttctgctg gagcagctga acatatacat agatgttgcc ctgccctccc    2100
catctgcacc ctgttgagtt gtagttggat ttgtctgttt atgcttggat tcaccagagt    2160
gactatgata gtgaaaagaa aaaaaaaaaa aaaaaaagga cgcatgtatc ttgaaatgct    2220
tgtaaagagg tttctaaccc accctcacga ggtgtctctc accccacac tgggactcgt     2280 gtggcctgtg tggtgccacc ctgctggggc ctcccaagtt ttgaaaggct ttcctcagca    2340
tctgggaccc aacagagacc agcttctagc agctaaggag gccgttcagc tgtgacgaag    2400
gcctgaagca caggattagg actgaagcga tgatgtcccc ttccctactt cccccttgggg   2460 ctccctgtgt cagggcacag actaggtctt gtggctggtc tggcttgcgg cgcgaggatg    2520
gttctctctg gtcatagccc gaagtctcac agcagtccca aaggaggctt acaactcctg    2580
catcacaaga aaaaggaagc cactgccagc tgggggatc tgcagctccc agaagctccg     2640
tgagcctcag cctaccccctc agactgggtt cctctccaag ctcgccctct ggaggggcag   2700
cgcagcctcc caccaagggc cctgcgacca cagcagggat tgggatgaat tgcctgtcct    2760
ggatctgctc tagaggccca agctgcctgc ctgaggaagg atgacttgac aagtcaggag    2820
acactgttcc caaagccttg accagagcac ctcagcccgc tgaccttgca caaactccat    2880
ctgctgccat gagaaaaggg aagccgcctt tgcaaaacat tgctgcctaa agaaactcag    2940
cagcctcagg cccaattctg ccacttctgg tttgggtaca gttaaaggca accctgaggg    3000
acttgcagta gaaatccagg gcctcccctg gggctggcag cttcgtgtgc agctagagct    3060
ttacctgcaa ggaagtctct gggcccagaa ctctccacca agagcctccc tgccgttcgc    3120
tgagtcccag caattctaag ttgaagggat ctgagaagga aaggaaatg tggggtagat     3180 ttggtggtgg ttagagatat gccccctca ttactgccaa cagttccggc cgcatttctt     3240
cacgcacctc ggttcctctt cctgaagttc ttgtgccctg ctcttcagca ccatgggcct    3300
tatacggaag gctctgggat ctccccttg tggggcaggc tcttggggcc agcctaagat     3360
catggtttag ggtgatcagt gctggcagat aaattgaaaa ggcacgctgg cttgtgatct    3420
taaatgagga caatcccccc agggctgggc actcctcccc tccctcact tctcccacct     3480 gcagagccag tgtccttggg tgggctagat aggatatact gtatgccggc tccttcaagc    3540
tgctgactca ctttatcaat agttccattt aaattgactt cagtggtgag actgtatcct    3600
gtttgctatt gcttgttgtg ctatgggggg agggggagg aatgtgtaag atagttaaca     3660
tgggcaaagg gagatcttgg ggtgcagcac ttaaactgcc tcgtaaccct tttcatgatt    3720
```

-continued

```
tcaaccacat tgctagagg gagggagcag ccacggagtt agaggccctt ggggtttctc    3780
ttttccactg acaggctttc ccaggcagct ggctagttca ttccctcccc agccaggtgc    3840
aggcgtagga atatggacat ctggttgctt tggcctgctg ccctctttca ggggtcctaa    3900
gcccacaatc atgcctccct aagaccttgg catccttccc tctaagccgt tggcacctct    3960
gtgccacctc tcacactggc tccagacaca cagcctgtgc ttttggagct gagatcactc    4020
gcttcaccct cctcatcttt gttctccaag taaagccacg aggtcggggc gagggcagag    4080
gtgatcacct gcgtgtccca tctacagacc tgcggcttca taaaacttct gatttctctt    4140
cagctttgaa aagggttacc ctgggcactg gcctagagcc tcacctccta atagacttag    4200
ccccatgagt tgccatgtt gagcaggact atttctggca cttgcaagtc ccatgatttc    4260
ttcggtaatt ctgagggtgg ggggagggac atgaaatcat cttagcttag ctttctgtct    4320
gtgaatgtct atatagtgta ttgtgtgttt taacaaatga tttacactga ctgttgctgt    4380
aaaagtgaat ttggaaataa agttattact ctgattaaat aaggtctcca ttcatggatt    4440
ccaaggacaa gaaagtcata tagaatgtct atttttaag ttctttccca cgcacccta     4500 gat                                                                  4503
```

<210> SEQ ID NO 6
<211> LENGTH: 23
<212> TYPE: RNA
<213> ORGANISM: Homo sapiens

<400> SEQUENCE: 6
gugaucuuaa augaggacaa ucc                                            23

<210> SEQ ID NO 7
<211> LENGTH: 23
<212> TYPE: RNA
<213> ORGANISM: Homo sapiens

<400> SEQUENCE: 7
aaugucccga auucccagcc uca                                            23

<210> SEQ ID NO 8
<211> LENGTH: 23
<212> TYPE: RNA
<213> ORGANISM: Homo sapiens

<400> SEQUENCE: 8
uuagcuuucu gucugugaau guc                                            23

<210> SEQ ID NO 9
<211> LENGTH: 41
<212> TYPE: DNA
<213> ORGANISM: Homo sapiens

<400> SEQUENCE: 9
aattctaggc gatcgctcga gaagcagggt ttgtgatcag g                        41

<210> SEQ ID NO 10
<211> LENGTH: 43
<212> TYPE: DNA
<213> ORGANISM: Homo sapiens

<400> SEQUENCE: 10
attttattgc ggccagcggc cgcggtgcgt gggaaagaac tta                      43

```
<210> SEQ ID NO 11
<211> LENGTH: 52
<212> TYPE: DNA
<213> ORGANISM: Homo sapiens

<400> SEQUENCE: 11
cacgctggct tgtgatctta aatgagggtc gatcccccag ggctgggcac tc              52

<210> SEQ ID NO 12
<211> LENGTH: 52
<212> TYPE: DNA
<213> ORGANISM: Homo sapiens

<400> SEQUENCE: 12
gagtgcccag ccctggggga tcgaccctca tttaagatca caagccagcg tg              52

<210> SEQ ID NO 13
<211> LENGTH: 41
<212> TYPE: DNA
<213> ORGANISM: Homo sapiens

<400> SEQUENCE: 13
tggtggcctg caggtgaatt caagcagggt ttgtgatcag g                          41

<210> SEQ ID NO 14
<211> LENGTH: 41
<212> TYPE: DNA
<213> ORGANISM: Homo sapiens

<400> SEQUENCE: 14
gagctgcagt ctagaggatc cggtgcgtgg gaaagaactt a                          41
```

MICRORNAS THAT SILENCE TAU EXPRESSION

CROSS-REFERENCE TO RELATED APPLICATIONS

The present application is a U.S. national phase application under 35 U.S.C. § 371 of International Patent Application No. PCT/US2014/046373 filed Jul. 11, 2014, which claims the benefit of priority to U.S. provisional patent application Ser. No. 61/844,977 filed Jul. 11, 2013, the disclosures of all of which are hereby incorporated by reference in their entireties. The International Application was published in English on Jan. 15, 2015 as WO 2015/006705.

GOVERNMENT SUPPORT CLAUSE

This invention was made with government support under grant AG036453 awarded by the NIH. The Government has certain rights in this invention

FIELD OF THE INVENTION

This invention relates to the treatment and prevention of Alzheimer's disease (AD), tangle-predominant dementia (TPD) and other diseases associated with abnormal tau expression, e.g., tauopathies, as well as neurodegeneration, using the 3'untranslated region (UTR) of the tau messenger RNA (mRNA) as a target, specifically using microRNAs that regulate the expression of tau. This invention is also in the field of screening for, identifying, and diagnosing such diseases. Specifically, this invention provides biomarkers for these diseases in the form of microRNAs.

BACKGROUND OF THE INVENTION

The presence of abnormal neuronal and glial filamentous inclusions composed of the microtubule-associated protein tau defines a heterogeneous group of neurodegenerative disorders, termed tauopathies (Dickson (2009)). Alzheimer's disease (AD) is currently classified as a secondary tauopathy, with tangles arising as a result of increased levels of toxic species of the amyloid-beta peptide (Aβ) (Hardy (2006)). The discovery of mutations in the microtubule-associated protein tau gene (MAPT) that cause frontotemporal lobar degeneration (FTLD) show that tau dysfunction on its own is sufficient to induce neurodegeneration (Hutton et al. (1998); Gasparini et al. (2007)), but the majority of patients with tangles lack such mutations. One example of a sporadic non-mutational primary tauopathy is tangle-predominant dementia (TPD) (Ulrich et al. (1992); Bancher and Jellinger (1994)). These exceptional patients develop neurofibrillary tangles that are regionally, morphologically, ultrastructurally and biochemically identical to those in moderate-stage AD, yet lack significant Aβ deposition as plaques (Santa-Maria et al. (2012)(1)). There are currently no effective treatments for either AD or TPD.

In the adult brain, a single gene (MAPT) on chromosome 17 gives rise to predominantly six tau isoforms (Wade-Martins (2012)). Alternative splicing of exon 10 results in tau containing either three or four tandem micro-tubule-binding domain repeats that mediate binding to tubulin (Weingarten et al. (1975)). Alternative splicing of exons 2 and 3 also occurs. Tau expression is not limited to neurons, as its presence in oligodendrocytes and astrocytes has also been observed (Binder et al. (1985); Chin and Goldman (1996)). Tau is found in somatodendritic compartments where it interacts with various proteins and the plasma membrane to modulate a wide variety of processes and signaling pathways (Tashiro et al. (1997); Maas et al. (2000); Avila et al. (2004); Morris et al. (2011)). Tau is highly abundant in axons (Mandell and Banker (1995); Dotti et al. (1987); Trojanski et al. (1989); Litman et al. (1993)), where it facilitates tubulin assembly by nucleating, bundling and stabilizing microtubules. Tau also binds to actin, influencing polymerization, and might orchestrate the interaction of microtubules and actin polymers in the organization of the cytoskeletal network (Kotani et al. (1985); Fulga et al. (2007); He et al. (2009); Farias et al. (2002)). By binding to sites on tubulin that overlap with those of other proteins, such as the molecular motor kinesin, tau can also influence axonal transport (Ebneth et al. (1998); Terwel et al. (2002)). Finally, tau may also play a role in neurogenesis (Bullmann et al. (2007); Hong et al. (2010)).

Since tau has numerous functions, it likely contributes to neurodegeneration in multiple ways, including both gain- and loss-of-function effects. Under pathological conditions, tau becomes hyperphosphorylated (Lippens et al. (2012)), aggregated (Mandelkow and Mandelkow (2012); Hernandez and Avila (2008)) and disseminated to neighboring neurons (Le et al, (2012); Santa-Maria et al. (2012)(2)). How this occurs in the absence of coding region mutation or imbalances in alternative splicing is not clear, but secondary post-translational modification plays a role (Lippens et al. (2012); Mandelkow and Mandelkow (2012)). Alternatively, accumulation of abnormal tau protein could be facilitated by failure in protein degradation systems (Wang and Mandelkow (2012)). One additional mechanism that has not been directly addressed is whether increased tau synthesis stemming from dysregulation of tau translation by microRNAs plays a role in tauopathy.

MicroRNAs are small non-coding RNAs averaging 22 nucleotides that regulate the expression of their target mRNA transcripts (Ambros (2004); Bartel (2009), and likely play a role in brain aging, neurodegeneration and neuroprotection (Kosik (2006); Saugstad (2010); Abe and Bonini (2013); Gascon and Gao (2012); Schonrock and Gotz (2012)). Mature microRNAs are derived from 70-100 bp precursors that are consecutively processed by the type III RNases, Drosha and Dicer, in the nucleus and the cytoplasm, respectively (Perron and Provost (2009)). RNA strands are then incorporated into the RNA-induced silencing complex. Binding of microRNAs to their targets is specified by complementary base pairing between positions 2-8 of the microRNA and the target 3' untranslated region (3' UTR) (Bartel (2009), an mRNA component that influences translation, stability and localization (Mazumder et al. (2003)); Kuersten and Goodwin (2003); Matoulkova et al. (2012). The precise mechanism whereby microRNAs silence their targets is under debate (Eulalio et al. (2008); Flynt and Lai (2008)).

While tau is regulated post-transcriptionally, it is not known whether microRNAs play a direct role.

SUMMARY OF THE INVENTION

This invention is based on the surprising discovery that a dysregulation of microRNAs contribute to the development of tauopathies. Specifically, these microRNAs bind to the 3'UTR of the tau mRNA derived from the tau gene, MAPT, regulating the expression of tau. In patients with tauopathies, such as Alzheimer's disease and tangle-predominant dementia, there is a decreased level of some microRNAs, including one designated miR-219-5p, which leads to the overexpression of pathological tau. This discovery can be used for many applications including screening for, diagnosis, prevention, and treatment of tauopathies, in particular Alzheimer's disease and tangle-predominant dementia. It can also be used for drug screening of potential therapies for diseases and disorders caused by excessive tau as well as the basis for models for research regarding tauopathies.

One embodiment of the present invention is a method of treating or preventing a tauopathy, especially Alzheimer's disease and tangle-predominant dementia, in a subject by increasing the level of microRNAs that binds to the 3'UTR of the tau mRNA gene in a subject in need thereof. The increase can be accomplished by administering a therapeutically effective amount of an agent that increases the production of microRNA that binds to the 3'UTR of the MAPT gene, or an agent that increases the binding or facilitates the binding of microRNA to the 3'UTR of the MAPT gene.

This increase can also be accomplished by administering a therapeutically effective amount of a composition comprising a microRNA that binds to the 3'UTR of the tau mRNA derived from the tau MAPT gene. The composition can also comprise a ligand, a conjugate, a vector, a lipid, a liposome, a carrier, an adjuvant or a diluent. The microRNA that can be used in the method include those listed in Tables 4 and 5 as well as those from miRNA families miR-181abcd/4262, miR-27ABC/27a-3p, miR-34ac/34bc-5p/449abc/449c-5p, miR-132/212/21/-3p, miR-146ac/146b-5p, miR-204/204b/211, and miR-219-5p/508/508-3p/4782-3p. Additional microRNAs that can be used in the method include miR-185, miR-151-5p, miR-149, and miR-409-3p. Preferred microRNAs for use in the method are miR-34c-5p, miR-132-3p, miR-27a-5p, miR-204-5p, miR-485-5p, miR-181b-5p, 181d-5p, and miR-219-5p.

The most preferred microRNA for use in the method is from family miR219-5p/508/508-3p/4782-3p and more specifically designated miR-219-5p comprising the nucleotide sequence of SEQ ID NO: 1, or a microRNA with a nucleotide sequence similar to or homologous to the sequence of SEQ ID NO: 1, sufficient to maintain binding to the 3'UTR of the MAPT gene. Other preferred microRNAs that can be used the method include but are not limited to the microRNA designated miR-485-5p comprising the nucleotide sequence of SEQ ID NO: 2, the microRNA 181d-5p comprising the nucleotide sequence SEQ ID NO: 3, and miR-34c-5p, miR-132-3p, miR-27a-5p, miR181b-5p, and miR-204-5p.

Additionally, a microRNA or microRNA mimic that binds to the tau mRNA derived from the tau MAPT 3'UTR can be designed by using the sequence information. The H1 haplotype of the MAPT 3' UTR is found at chromosome 17 between base pairs 44,101295 and 44,105,727 and is set forth in SEQ ID NO: 4. The H2 haplotype of the MAPT 3'UTR is found at chromosome 17 between base pairs 76,2196-76,6698 and is set forth in SEQ ID NO: 5.

More specifically a microRNA or microRNA mimic that binds to the conserved region of the MAPT 3' UTR mRNA that miR-219-5p binds can be designed using that sequence which is:

SEQ ID NO: 6
5'-gugaucuuaaaugaggacaaucc-3'

Also a microRNA that binds to the conserved region of the MAPT 3'UTR mRNA that miR-485-5p binds can be designed using that sequence which is:

SEQ ID NO: 7
5'-aaugucccgaauucccagccuca-3'

Also a microRNA that binds to the conserved region of the MAPT 3'UTR mRNA that miR-181-5p binds can be designed using that sequence which is:

SEQ ID NO: 8
5'-uuagcuuucugucugugaauguc-3'

This increase can also be accomplished by administering a therapeutically effective amount of a composition comprising DNA that encodes a microRNA that binds to the 3'UTR of the tau mRNA derived from the tau MAPT gene including those listed in Tables 4 and 5 as well as those from miRNA families miR-181abcd/4262, miR-27ABC/27a-3p, miR-34ac/34bc-5p/449abc/449c-5p, miR-132/212/21/-3p, miR-146ac/146b-5p, miR-204/204b/211, and miR-219-5p/508/508-3p/4782-3p. DNA that encodes microRNA miR-185, miR-151-5p, miR-149, and miR-409-3p, can also be used in the method. Preferred microRNAs for use in the method are miR-34c-5p, miR-132-3p, miR-27a-5p, miR-204-5p, miR-485-5p, miR-181b-5p. miR-181d-5p and miR-219-5p.

The composition can also comprise a ligand, a conjugate, a vector, a lipid, a liposome, a carrier, an adjuvant or a diluent. The preferred DNA for use in the method is one which encodes the microRNA designated miR-219-5p comprising the nucleotide sequence of SEQ ID NO: 1, or a microRNA with a nucleotide sequence similar to or homologous to the sequence of SEQ ID NO: 1, sufficient to maintain binding to the 3'UTR of the MAPT gene. Other DNA that can be used the method include but are not limited to DNA that encodes microRNA designated miR-485-5p comprising the nucleotide sequence of SEQ ID NO: 2, or a microRNA with a nucleotide sequence similar to or homologous to the sequence of SEQ ID NO: 2, sufficient to maintain binding to the 3'UTR of the MAPT gene, DNA that encodes microRNA designated miR-181d-5p comprising nucleotide sequence of SEQ ID NO: 3, or a microRNA with a nucleotide sequence similar to or homologous to the sequence of SEQ ID NO: 3, sufficient to maintain binding to the 3'UTR of the MAPT gene and DNA that encodes microRNA designed to bind to the nucleotides comprising SEQ ID NOs: 4-8 or miR-34c-5p, miR-132-3p, miR-27a-5p, or miR-204-5p.

Another embodiment of the present invention is a method for screening, diagnosing, predicting and/or identifying a tauopathy, especially Alzheimer's disease or tangle-predominant dementia, comprising obtaining biological tissue and/or bodily fluid from a subject, purifying and/or isolating the RNA from the tissue or fluid, and detecting the presence or absence of particular microRNAs.

Specifically low levels or no presence of some microRNA, including but not limited to the miRNA designated miR-219-5p, with the nucleotide sequence set forth in SEQ ID NO: 1, and/or high levels of some microRNA, including but not limited to the miRNA designated miR181d-5p, with the nucleotide sequence set forth in SEQ ID NO: 3, determines, diagnoses, predicts or identifies a patient as having a tauopathy, including AD or TPD.

A further embodiment of the present invention is a method for screening, diagnosing predicting, and/or identifying a tauopathy, in particular, Alzheimer's disease and/or tangle-predominant dementia, comprising obtaining biological tissue and/or bodily fluid from a subject, purifying and isolating RNA from said biological tissue, and detecting the levels of microRNA, including but not limited to those designated miR-219-5p in the purified and isolated RNA sample. The level of miRNA, e.g., miR-219-5p is compared to the levels in an RNA sample from a healthy control. If the level of miR-219-5p, e.g., is different, either qualitatively, e.g., by visualization, or quantitatively, e.g., comparison to a known quantity of the proteins in a healthy control, the patient can be diagnosed or identified as having a tauopathy A further embodiment of the present invention is a method for screening, diagnosing predicting, and/or identifying a tauopathy, in particular, Alzheimer's disease and/or tangle-predominant dementia, comprising obtaining biological tissue and/or bodily fluid from a subject, purifying and isolating RNA from said biological tissue, and detecting the levels of microRNA including but not limited to those designated miR-181d-5p in the purified and isolated RNA sample. The level of miRNA, e.g., miR-181d-5p is compared to the levels in an RNA sample from a healthy control. If the level of miRNA, e.g., miR-181d-5p is different, either qualitatively, e.g., by visualization, or quantitatively, e.g., comparison to a known quantity of the proteins in a healthy control, the patient can be diagnosed or identified as having a tauopathy In a preferred embodiment, the patient who is being tested has a cognitive impairment that might be diagnosed as Alzheimer's disease and/or tangle-predominant dementia.

The purified and/or isolated RNA can be obtained from any biological tissue. Preferred biological tissues include, but are not limited to, brain, epidermal, whole blood, and plasma.

The purified and/or isolated RNA can be obtained from any bodily fluid. Preferred bodily fluids include, but are not limited to, cerebrospinal fluid, plasma, saliva, sweat, and urine.

The microRNA can be purified and isolated using any method known in the art.

Methods for detecting microRNA include but are not limited to Northern blots, in situ hybridization, real time PCR, nuclease protection assays, poly-A tailed reverse transcription, microRNA amplification profiling, microRNA serial analysis of gene expression, microarrays, enzyme amplified assays, sequencing, RNA-seq., and nanoparticle methods.

In a preferred embodiment, the quantity of miRNA is measured in the RNA sample from the subject and compared to a reference value of the quantity of miRNA in a healthy control, wherein the reference value represents a known diagnosis or prediction of normal cognitive function, and finding a deviation in the quantity of miRNA from the RNA sample of the subject and the reference value, wherein if the quantity of miRNA is different from the RNA sample of the subject than the reference value, then the subject can be determined, diagnosed, predicted or identified as having AD or TPD.

Other miRNA can be used in a method for screening, diagnosing, predicting and/or identifying a tauopathy, especially Alzheimer's disease or tangle-predominant dementia. Any miRNA that is differentially expressed in Alzheimer's disease or tangle-predominant dementia can be used. miRNAs that are down-regulated or found in lower levels in patients with Alzheimer's disease include but not limited to those listed in Table 11. miRNAs that are up-regulated or found in higher levels in Alzheimer's disease include but are not limited to those listed in Table 12. miRNAs that are down-regulated or found in lower levels in patients with tangle-predominant dementia include but not limited to those listed in Table 13. miRNAs that are up-regulated or found in higher levels in patients with tangle-predominant dementia include but are not limited to those list in Table 14. miRNAs that down-regulated or found in lower levels in patients with tangle-predominant dementia as compared to patients with Alzheimer's disease include but are not limited to those listed in Table 15. miRNAs that are up-regulated or found in higher levels in patients with tangle-predominant dementia as compared to patients with Alzheimer's disease include but are not limited to those listed in Table 16.

The present invention also includes kits embodying any of the aforementioned assays and methods.

The present invention also provides for methods and tools for drug design, testing of agents, and tools for basic research into the causes and etiology of tauopathies including Alzheimer's disease and tangle-predominant dementia. The present invention also provides a method for determining target genes or proteins for drug development and basic research regarding these diseases.

A further embodiment of the present invention is a method and/or assay for screening and/or identifying a test agent for the prevention and/or treatment of tauopathies, including but not limited to AD and TPD, comprising contacting or incubating a test agent to a nucleotide comprising 3' UTR of MAPT or a portion thereof, including but not limited to, SEQ ID NOs: 4-8 and determining if the test agent binds to the nucleotide, i.e., DNA or RNA, wherein if the test agent binds to the nucleotide, the test agent is identified as a therapeutic and/or preventative agent for tauopathies, including but not limited to AD and TPD.

A further embodiment of the present invention is a method and/or assay for screening and/or identifying a test agent for the prevention and/or treatment of tauopathies, including but not limited to AD and TPD comprising contacting or incubating a test agent with a nucleotide comprising 3' UTR of MAPT or a portion thereof, including but not limited to, SEQ ID NOs: 4-8, and detecting the expression of the nucleotide before and after contact or incubation with the test agent, wherein if the expression of the nucleotide is decreased after the contact or incubation with the test agent, the test agent is identified as a therapeutic and/or preventative agent for tauopathies, including but not limited to AD and TPD.

A further embodiment of the present invention is a method and/or assay for screening and/or identifying a test agent for the prevention and/or treatment of tauopathies, including but not limited to AD and TPD comprising contacting or incubating a test agent with a gene construct comprising a nucleotide comprising 3' UTR of MAPT or a portion thereof, including but not limited to, SEQ ID NOs: 4-8, and detecting the expression of the nucleotide in the gene construct before and after contacting or incubating the test agent with the gene construct, wherein if the expression of the gene is reduced or decreased after contact with the test agent, the test agent is identified as a therapeutic and/or preventative agent for tauopathies, including but not limited to AD and TPD.

A further embodiment of the present invention is a method and/or assay for screening and/or identifying a test agent for the prevention and/or treatment of tauopathies, including but not limited to AD and TPD, comprising transforming a host cell with a gene construct comprising a nucleotide comprising the 3' UTR of MAPT or a portion thereof, including but not limited to, SEQ ID NOs: 4-8, detecting the expression of the nucleotide in the host cell, contacting the test agent with the host cell, and detecting the expression of the nucleotide in the host cell after contact with the test agent or compound, wherein if the expression of the nucleotide is reduced or decreased after contact with the test agent or compound, the test agent is identified as a therapeutic and/or preventative agent for tauopathies, including but not limited to AD and TPD.

The expression of a nucleotide or gene can be determined using a measurable phenotype, either one that is native to the gene or one that is artificially linked, such as a reporter gene.

A further embodiment of the invention is a method and/or assay for screening and/or identifying a test agent for the prevention and/or treatment of tauopathies, including but not limited to AD and TPD, comprising contacting or incubating a test agent with an animal, comprising a phenotype that is correlated to the 3'UTR of the MAPT gene or a portion thereof including but not limited to, SEQ ID NOs: 4-8, and/or a phenotype correlated with the expression of a microRNA and/or a phenotype correlated to excessive tau expression, detecting or observing the phenotype in the animal, contacting or incubating the test agent with the animal, and detecting or observing the phenotype after contact or incubation with the test agent, wherein if the phenotype is altered or changed after contact or incubation with the test agent, the test agent is identified as a therapeutic and/or preventative agent for tauopathies, including but not limited to AD and TPD.

The phenotype can be native to the animal or one that has been artificially produced, e.g., transgenic Drosophila.

A test agent can include microRNAs not yet known to have a target gene.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIGS. 5A-C depict images of immunohistochemistry using antisera targeting the neuronal marker MAP2 in primary hippocampal neurons that have been transduced with a lentiviral vector containing the miR-219 precursor and GFP. Scale bar=25 µm. FIG. 5D is a graph depicting results of QPCR on total RNA isolated from cultures transduced with the mir-219 lentivirus. * p<0.05.

FIG. 6A is a graph of the results of luciferase activity in hippocampal cultures co-transduced with lentiviral vectors containing firefly luciferase upstream of the entire human tau 3' UTR together with a vector containing miR-219, a negative control lentiviral vector containing a scrambled miR, and an empty vector control. FIG. 6B is representative immunoblot analysis, both images and quantified results, of primary hippocampal cultures using antisera targeting total tau (TauC). FIG. 6C is a graph of the results of QPCR analysis of primary hippocampal cultures transduced with lentiviral vectors containing firefly luciferase upstream of the entire human tau 3' UTR together with a vector containing miR-219, a negative control lentiviral vector containing a scrambled miR, and an empty vector control tau mRNA levels. * p<0.05

FIG. 7A is a representative immunoblot analysis, both images and quantified results, using antisera targeting total tau reveals increased expression of tau protein in PC-12 cells following NGF treatment compared to controls. FIG. 7B is a graph of tau mRNA levels in control, and PC-12 cells treated with NGF for 3 days and 7 days. FIG. 7C is a graph of miR-219-5p levels in control, and PC-12 cells treated with NGF for 3 days and 7 days. FIG. 7D is a graph of the results of QPCR analysis of miR-219-5p levels following lentiviral transduction, and FIG. 7E is a graph of QPCR analysis of tau mRNA levels in cells transduced with lentiviral miR-219-5p and the scrambled miR. FIG. 7F is a representative immunoblot analysis, both images and quantified results of PC12 cells transduced with miR-219-5p, scrambled RNA, or an empty vector, using antisera against total tau. FIGS. 7G and 7H are images of immunohistochemistry using antisera recognizing total tau in PC12 cells without NGF exposure and exposed to NGF for seven days. FIG. 7I-K are images observed by immunofluorescence confocal microscopy of PC-12 cells transduced with lentiviral miR-219-5p and a GFP reporter. FIG. 7K is the merge of FIGS. 8I and 8J. Scale bar=25 µm. * p<0.05.

FIG. 8A shows flies with the overexpression of miR-219. These flies have a wing held up phenotype as compared to controls shown in FIG. 8B. FIG. 8C shows the flies in a negative geotaxis or climbing assay, with controls in the left tube, flies overexpressing miR-219 in the center tube, and flies overexpressing miR-134 in the right tube. FIG. 8D is a graph quantifying the results of the negative geotaxis assay.

FIG. 10A-E are images of the eyes of Drosophila.

DETAILED DESCRIPTION OF THE INVENTION

Definitions

Figure 1A:
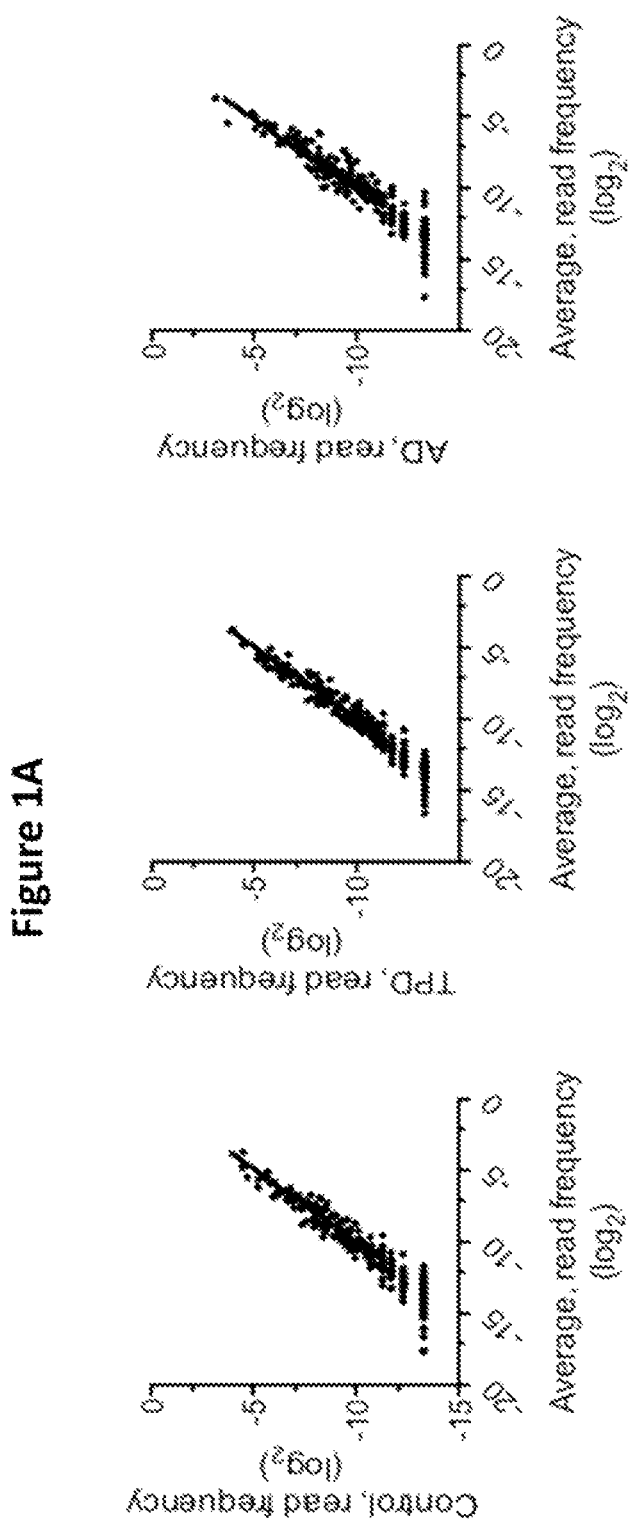
FIG. 1A are graphs of the average read frequency versus the read frequency for Alzheimer's disease (AD), tangle-predominant dementia (TPD) and control subjects from RNA-seq experiments.
Figure 1B:
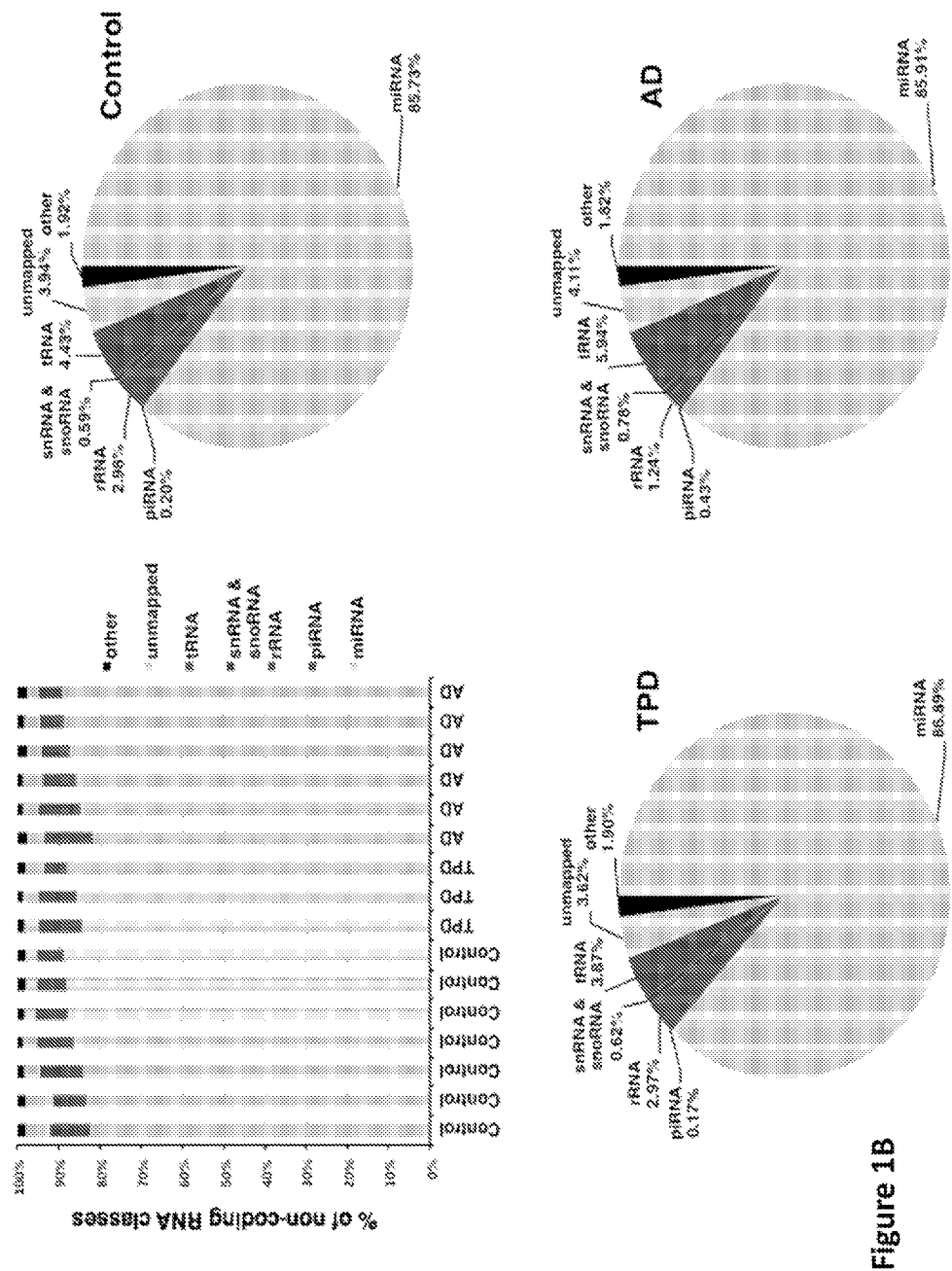
FIG. 1B is a histogram and pie charts showing the proportion of reads mapping to non-coding RNA sub-groups.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is one suffering with cognitive impairment ranging from mild to severe, or with pre-dementia in the prodromal phase.

The term "healthy control" or "control" would be a human subject who is not suffering from dementing illness and has normal cognitive function. Moreover, it is preferred that the healthy control be age-matched to the subject, within a reasonable range.

The term "mild cognitive impairment" or "MCI" as used in this application means an intermediate stage between the expected cognitive decline of normal aging and the more serious decline of dementia. It is a brain function syndrome involving the onset and evolution of cognitive impairments beyond those expected based on the age and education of the individual, but which are not significant enough to interfere with their daily activities. It is often found to be a transitional stage between normal aging and dementia. Although MCI can present with a variety of symptoms, when memory loss is the predominant symptom it is termed "amnestic MCI" and is frequently seen as a prodromal stage of Alzheimer's disease.

The terms "Alzheimer's disease" and "AD" will be used interchangeable and is a disease in which there is mild cognitive impairment and the presence of amyloid plaques comprising Aβ.

The terms "tangle-predominant dementia", "tangle-only dementia", "TOD", and "TPD", "tangle-predominant senile dementia", "senile dementia of the tangle type", "senile dementia with tangles", and "limbic neurofibrillary tangle dementia", will be used interchangeably in this application and are defined as patients who develop neurofibrillary tangles that are regionally, morphologically, ultrastructurally and biochemically similar to those in moderate-stage AD, but lack significant Aβ deposition as plaques (Santa-Maria et al. (2012)(1)).

The term "tauopathy" as used herein means a neurodegenerative disease characterized by the accumulation of tau protein in the brain. These tauopathies include, but are not limited to, progressive supranuclear palsy, chronic traumatic encephalopathy, frontotemporal dementia with Parkinsonism linked to chromosome 17 (FTLD-tau), frontotemporal dementia, ganglioglioma, gangliocytoma, meningioangiomatosis, Pick's disease, and corticobasal degeneration.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "in need thereof" would be a subject known or suspected of having or being at risk of Alzheimer's disease, tangle-predominant dementia, or another tauopathy or a disease or condition that causes neurodegeneration. In the case of AD or TPD, the subject may be suffering from cognitive impairment ranging from mild to severe, or with pre-dementia in the prodromal phase The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The terms "screen" and "screening" and the like as used herein means to test a subject or patient to determine if they have a particular illness or disease, in this case AD, TPD or another tauopathy. The term also means to test an agent to determine if it has a particular action or efficacy.

The terms "diagnosis", "diagnose", diagnosing" and the like as used herein means to determine what physical disease or illness a subject or patient has, in this case AD, TPD or another tauopathy.

The terms "identification", "identify", "identifying" and the like as used herein means to recognize a disease in a subject or patient, in this case AD, TPD or another tauopathy. The term also means to recognize an agent as being effective for a particular use.

The terms "prediction", "predict", "predicting" and the like as used herein means to tell in advance based upon special knowledge.

The term "reference value" as used herein means an amount of a quantity of a particular protein or nucleic acid in a sample from a healthy control.

The terms "MAPT", "MAPT gene" and "MAPT locus" are used interchangeably in this application and mean the microtubule-associated protein tau gene.

The terms "3'UTR" or "3'UTR of the MAPT gene" are used interchangeably in this application and mean the critical cis-acting regulatory elements that are capable of regulating gene expression on the post-transcriptional level by influencing mRNA stability and localization, among other functions (Aronov et al. (2001); Aronov et al. (1999)).

The terms "microRNA" or "miRNA" will be used interchangeably and are defined as small non-coding RNAs averaging 22 nucleotides that regulate the expression of their target mRNA transcripts (Ambros (2004); Bartel (2009)).

The term "microRNA mimics" are defined as containing non-natural or artificial double stranded microRNA-like RNA fragments that are constructed to contain a sequence motif on its 5'-end that is partially complementary to the target sequence in the 3'UTR.

The terms "microRNA family" or "miRNA family" will be used interchangeably throughout the application and will refer to microRNAs with the same seed, which is defined as nucleotide positions 2 through 8 of the 5' end of the mature microRNA. For example, miR-181b-5p and miR-181d-5p are from the microRNA family miR-181abcd/4262 and have the identical seed sequence. Thus, if one or two microRNA from a family is shown or predicted to bind to the 3'UTR of MAPT, then it would be assumed that the other microRNA in that family would also bind to the 3'UTR of MAPT.

The terms "miR-219-5p" or "miR-219" are used interchangeably throughout the application and refer to one of the microRNAs identified as useful in the diagnosis, prevention and treatment of tauopathies and neurodegeneration. When two mature microRNAs originate from opposite arms of the same pre-miRNA, they are denoted with a -3p or -5p suffix. Persons of skill in the art will recognize that one mature miRNA is more abundant than the other and that with regard to other microRNAs described throughout the application that at some times have the "5p" or "3p" designation, and at some times do not, are describing the same microRNA, e.g., miR-181d and mir-181d-5p.

The term "antisense DNA" is the non-coding strand complementary to the coding strand in double-stranded DNA.

As used herein, the term "isolated" and the like means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, an isolated genomic DNA, or a restriction fragment. In another embodiment, an isolated nucleic acid is preferably excised from the chromosome in which it may be found. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated material may be, but need not be, purified.

The term "purified" and the like as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

The term "nucleic acid hybridization" refers to antiparallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an antiparallel hybrid).

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA.

Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts, and many appropriate host cells, are known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described herein.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin. Sequence identity can be determined using any of a number of publicly available sequence comparison algorithms, such as BLAST, FASTA, DNA Strider, or GCG (Genetics Computer Group, Program Manual for the GCG Package, Version 7, Madison, Wis.).

The terms "substantially homologous" or "substantially similar" when at least about 80%, and most preferably at least about 90 or 95%, 96%, 97%, 98%, or 99% of the nucleotides match over the defined length of the DNA sequences, as determined by sequence comparison algorithms, such as BLAST, FASTA, and DNA Strider. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

MicroRNA as a Regulator of Tau

Intracellular aggregation and accumulation of tau protein as neurofibrillary tangles occurs in the soma and processes of neurons and glia in at least 23 brain diseases, the most common of which is Alzheimer's disease (AD). It was hypothesized that disregulation of tau-silencing microRNAs plays a role in the pathogenesis of neurofibrillary tangle formation by provoking an increase in the levels of tau protein independently of tau mRNA levels or imbalances in splicing. This hypothesis builds on previous studies describing alterations in microRNAs in AD and other neurodegenerative diseases (Wang et al. (2008); Hebert et al. (2008); Nunez-Iglesias et al. (2010); Smith et al. (2011); Kim et al. (2007); Packer et al. (2008); Rademakers et al. (2008); Wang et al. (2010)). This hypothesis is also based on the fact that the majority of human genes are regulated by microRNAs (Friedman et al. (2009)), and that MAPT has a relatively large (4.2 Kb) 3' UTR with multiple conserved predicted microRNA recognition elements.

This study utilized small RNA-sequences as it is quantitative and hybridization independent, avoiding cross reactivity of hybridization probes. Using strict neuropathological inclusion criteria and focusing on both AD and TPD patients, the study was able to pinpoint microRNAs that are associated with temporal lobe tau accumulation, a hallmark feature of AD. Furthermore, the inclusion for controls was strict, stratifying cases based on a model proposed by Rowe and Khan (1987). While tangles are commonly observed in aging, a subset of elderly individuals, termed successful "cerebral" aging, have essentially no age-linked temporal lobe tangles (Santa-Maria et al. (2012)(2)). Such controls are fundamentally different from younger controls without pathology, as they have escaped neurofibrillary degeneration and are enriched for protective factors. Together, this approach allowed the generation of a unique set of micro-RNA signatures that can be useful for differentiating AD and TPD from age-associated cognitive impairment, as well as be used for treatment of AD and TPD and other neurodegenerative conditions.

The findings set forth herein support the hypothesis that microRNAs are regulators of neurofibrillary degeneration, reducing tau expression at the post-transcriptional level. As decreasing tau expression protects from Aβ-induced cognitive impairment (Santacruz et al. (2005); Roberson et al. (2007); Roberson et al. (2011)), and tau reduction is generally well-tolerated in transgenic mouse models (Dawson et al. (2010)), reducing tau expression is an attractive strategy for treating AD and TPD and increasing microRNA can be accomplish this reduction.

The results presented herein strongly support the assertion that microRNA, in particular one designated miR-219-5p with a sequence comprising SEQ ID NO: 1, is a regulator of tau. This finding is supported by the broad conservation of the miR-219-5p recognition element in the tau 3' UTR (Examples 2 and 3) and in vitro experimentation using luciferase reporter assays demonstrating direct binding and silencing of tau 3' UTR activity by miR-219-5p (Examples 4 and 15). When hippocampal cultures were transduced with miR-219-5p, a significant decrease in tau protein levels was observed, while tau mRNA levels remained unchanged, illustrating that the mechanism of miR-219-5p silencing of tau expression includes inducing translational repression (Example 5).

Having shown that miR-219 can interact with the tau 3' UTR, it was next necessary to ask whether this occurs in a more physiological context. Functional trend analysis of predicted targets suggests that miR-219 plays a role in neuron differentiation, axon development and gene expression (Example 12; Table 9). Previous work has shown that tau is an important developmental protein, playing a functional role in neurite outgrowth (Drubin et al. (1988); Drubin et al. (1985)). Using PC12 cells exposed to nerve growth factor (NGF), a well-established neurite outgrowth model, it was confirmed that application of NGF induces differentiation into neuron-like cells with neurite outgrowth with concomitant increases in tau mRNA and protein levels. It was also found that NGF induces a transient but significant down-regulation of miR-219 that returns to baseline once the cells have fully differentiated, demonstrating an inverse correlation between active tau protein synthesis and miR-219 levels. Finally, it was found that overexpression of miR-219-5p blocked the increase in tau levels and abrogated neurite outgrowth in PC12 cells following neuron growth factor (NGF) application (Example 6). Altogether, these results suggest that NGF-induced tau protein synthesis is regulated post-transcriptionally by miR-219.

All of the findings herein were replicated in vivo using Drosophila. In Drosophila, many protein regulatory mechanisms are conserved with humans, including miRNA regulation (Dai et al. (2012)). Bioinformatics analysis reveals that the mature Drosophila miR-219 sequence has 100% sequence identity with human miR-219. Drosophila has a single tau gene that encodes a protein with 66% amino acid similarity with human tau. Drosophila and human tau share many critical features, including the microtubule binding domains (Hedari and Fortinin (2001)). Examination of the Drosophila genome reveals that the fly tau gene has a previously incompletely annotated 3' UTR region that extends for 1439 bp and contains a single miR-219 recognition element (Example 7; Table 8). In fact, of all the miRNAs predicted to target human tau, only the miR-219 recognition element is conserved in Drosophila, indicating a striking evolutionarily conserved relationship.

To ask whether Drosophila tau is also regulated by miR-219, this miRNA was overexpressed in neurons (Bejarano et al. (2012)). When miR-219 was overexpressed in the fly brain, the flies had different phenotypes, including a wings up phenotype and the inability to climb as high as controls (Example 8). Also there was a highly significant reduction in tau protein level compared to the scrambled miRNA control (Example 9). However, when a sponge inhibitor, a recombinant transcript containing multiple tandem miR-219 binding sites was expressed in the Drosophila, the levels of miR-219 expressed in Drosophila neurons decreased and there was a significant increase in the levels of endogenous tau protein compared to controls (Example 9). Overexpression of the miR-219 sponge also resulted in a significant increase in the Drosophila tau mRNA (Example 9). However, the Drosophila tau mRNA levels were unchanged following overexpression of miR-219, suggesting effects on both mRNA levels and translation (Example 9). Additionally, it was confirmed that that miR-219 is also capable of regulating human tau 3' UTR activity in vivo, using Drosophila that express a luciferase reporter fused to the human tau 3' UTR. In contrast, the miR-219 sponge inhibitor significantly increases luciferase activity, confirming an evolutionarily conserved bidirectional mechanism of tau regulation (Example 9).

Studies have shown that overexpression of tau results in a marked rough eye phenotype in transgenic Drosophila (Jackson et al. (2002); Wittman et al. (2001); Williams et al. (2000)), a finding replicated herein (Example 10). The results herein also show that both miR-219 and the human 3' UTR rescue the phenotype, showing that miR-219 regulates tau toxicity and there is a protective cis-acting regulatory element in the 3'UTR (Examples 10 and 11).

Among the pathogenic mechanisms that might contribute to tau toxicity are tau hyperphosphorylation, aggregation, decreased clearance and spreading to neighboring neurons (Morris et al. (2011)). One treatment strategy is to reduce the burden of toxic tau species in neurons either by reducing production or increasing clearance of hyperphosphorylated tau (p-tau) (Jinwal et al. (2013)). As shown herein, miR-219 is also predicted to silence the expression of GSK3β, a proline-directed serine/threonine kinase implicated in tau hyperphosphorylation (Example 14). Additionally, it is shown herein that miR-219 and other miRNAs target other kinases implicated in tau, such as human tau-tubulin kinase 1 (TTBK1), calcium/calmodulin-dependent protein kinase II gamma, and protein kinase A (PKA) (Example 14). These findings open up the possibility that a hitherto unrecognized post-transcriptional mechanism involving miRNA, regulates the expression of both tau and GSK3β and perhaps other kinases involved in tau.

Because microRNA targets the 3'UTR of MAPT, other tauopathies can also be treated using the microRNA. A tauopathy is a neurodegenerative disease characterized by the accumulation of tau protein in the brain. These tauopathies include, but are not limited to, progressive supranuclear palsy, chronic traumatic encephalopathy, frontotemporal dementia with Parkinsonism linked to chromosome 17

(FTLD-tau), frontotemporal dementia, ganglioglioma, gangliocytoma, meningioangiomatosis, Pick's disease, and corticobasal degeneration.

Moreover, while the mechanism underlying tauopathy may involve either a gain or loss of tau function, many investigators now argue that increased levels of toxic tau drive neurofibrillary degeneration (Morris et al. (2011); Mandelkow and Mandlekow (2012)). Previous studies in which the endoribonuclease Dicer, which is required for microRNA maturation, was genetically inactivated support the proposed role of microRNAs as modulators of tau toxicity in Drosophila melanogaster and rodent models (Hebert et al. (2010); Bilen et al. (2006)), raising the possibility that alterations in microRNAs may play a causative role in many neurodegenerative disorders (Schaefer et al. (2007)). The finding herein that neuron growth factor or NOF-mediated reduction in miR-219-5p may influence tau-mediated neurite outgrowth is intriguing as alterations in NOF signaling have been proposed to contribute to the pathogenesis of AD, and NGF is currently being evaluated as a therapeutic agent for neurodegeneration (Borlongon (2012)). Other studies have shown that disruption of NMDA receptor signaling reduces levels of miR-219-5p (Kocerha et al. (2009); Beveridge and Cairns (2012)), thus, microRNAs, specifically miR-219-5p, could play a role in the glutamate-induced toxicity through modulation of tau expression induced by NMDA, non-NMDA and metabotropic glutamate receptors agonists (Sindou et al. (1992); Couratier et al. (1995); Esclaire et al. (1997)). Additionally, the cycad-derived toxin known as cycasin as well as endogenous glutamate may increase tau expression, promoting tau protein accumulation and neurodegeneration in the amyotrophic lateral sclerosis/parkinsonism dementia complex of Guam through alterations in microRNA networks (Spencer et al. (2012)).

Additionally, the role of microRNA, specifically miR-219-5p, in tangle formation may not be limited to neurons, as miR-219-5p is present in glia as well, where it regulates oligodendrocyte differentiation and myelination (Zhao et al. (2010)).

Thus, other neurodegenerative diseases can be treated by increasing microRNA, as well as diseases associated with the glia.

Together, the results herein establish that tau expression is regulated by miRNA and more specifically at least miR-219. This conclusion is based on the fact that miR-219 specifically binds the tau 3' UTR in vitro and is bi-directionally regulated by miR-219 overexpression and inhibition in vivo. It is unlikely that miR-219 is alone among miRNAs in its ability to regulate human tau, as there are an abundance of miRNA recognition elements in the tau 3' UTR, and in vitro studies set forth herein have suggested other candidate tau regulating miRNAs. These include microRNA designated miR-34c-5p, miR-132-3p, miR-27a-5p, miR-204-5p, miR-485-5p, miR-181b-5p, mir-181d-5p, and miR-219-5p. Moreover, the results herein also show that the families of these miRNAs target other kinases involved in tauopathy (Example 14).

Also shown herein is that microRNA can regulate human tau via the 3'UTR of the MAPT gene in vivo and decrease a negative phenotype resulting from overexpression of tau. These in vivo results show the great promise for miRNA as a preventative and treatment for tauopathies caused by overexpression of tau and tau toxicity.

MicroRNAs

The results set forth herein show that microRNAs are implicated in tauopathies including but not limited to AD and TPD as well as other neurodegenerative diseases and conditions.

To start the results herein show there are 76 miRNAs differentially expressed in Alzheimer's disease versus controls, 152 miRNAs differentially expressed in tangle-predominant dementia versus controls and 54 miRNAs differentially expressed in tangle-predominant dementia and Alzheimer's disease. See Example 13, Tables 11-16.

Additionally certain miRNA have been shown to be differentially expressed in AD and TPD and target MAPT. These miRNAs include but are not limited to miR-185, miR151-5p, miR-219-5p, miR-149, miR-181d-5p, and miR-409-3p. See Example 2, Table 3.

Other miRNA families have been shown to target the 3'UTR of tau. These miRNA families are miR-181abcd/4262, miR-27ABC/27a-3p, mi-R34ac/34bc-5p/449abc/449c-5p, miR-132/212/21/-3p, miR-146ac/146b-5p, miR-204/204b/211, and miR-219-5p/508/508-3p/4782-3p (Example 2, Table 6; Example 15). These miRNAs are also predicted to target kinases involved in tauopathies, including GSK3β (Example 14, Table 17).

Additionally, several microRNAs have been predicted to target tau using Targetscan and are broadly conserved in vertebrates (Table 4) and mammals (Table 5).

Any of these microRNAs can be used in the methods of the present invention for the treatment and prevention of tauopathies as well as methods for screening for, identifying, and diagnosing such diseases. Preferred microRNAs for use in the method are miR-34c-5p, miR-132-3p, miR-27a-5p, miR-204-5p, miR-485-5p, miR-181b-5p, miR-181d-5p, and miR-219-5p.

Using expression profiling RNA from TPD, AD, and control brains, two microRNAs in particular, miR-219-5p and miR-181d-5p, were found that both have predicted recognition elements that are broadly conserved among vertebrates within the tau 3' UTR (Examples 1 and 2). miR-181 is increased in AD and TPD compared to controls. In contrast, miR-219-5p is decreased in AD and TPD compared to controls.

While it would be apparent why a decrease in a miRNA that regulates tau expression would increase tau production, it is less apparent why an increase in a miRNA that regulates tau expression would cause an increase for tau expression and be a marker for a tauopathy. Without being bound by any theory, the increase in some miRNAs that target tau including miR-181d is a reactive change. The brain in response to the increase in tau ramps up the miRNA production in an effort to decrease the overexpresssion of tau but it is too little too late and the miRNA level increases without actually decreasing tau expression. Thus, increasing this miRNA would also be beneficial in preventing and/or treating tauopathies, including AD and TPD.

Two precursors, designated mir-219-1 and mir-219-2, that arise from separate genes on chromosome 6 and 9, respectively, can produce an identical mature miR-219-5p. In the obtained profiles, negligible levels of miR-219-1-3p were obtained, suggesting the differences in the mir-219-2 precursor are responsible for the observed changes in miR-219-5p (Table 7).

The mature miR-219-5p sequence is highly conserved and distinct from miR-219-2-3p, which is not predicted to target tau. In contrast, while the miR-219-5p family (miR-219-5/508/508-3p/4782-3p) recognition element is not contained in the 3' UTR of other representative microtubule associated proteins, a highly-conserved miR-181 recognition element is found in the MAP1a, MAP1b and MAP2 3' UTRs, suggesting a relative selectivity of miR-219-5p for MAPT-derived transcripts (Table 6). Thus, miR-219-5p is a highly-conserved microRNA predicted to target tau that was observed to be down-regulated in AD and TPD brain.

Thus, one embodiment of the present invention is the isolated microRNA and the use of the isolated microRNA designated microRNA-219-5p, comprising the sequence:

(SEQ ID NO: 1)
5'ugauuguccaaacgcaauucuug-3'

Another microRNA that is useful in the methods of the invention is the microRNA designated miR-485-5p comprising the sequence of SEQ ID NO: 2. Thus, another embodiment of the present invention is the isolated microRNA designated microRNA-485-5p and the use of the isolated microRNA designated microRNA-485-5p, comprising the sequence:

(SEQ ID NO: 2)
5'-agaggcuggccgugaugaauuc-3'

Another microRNA that is useful in the methods of the invention is the microRNA designated miR-181d comprising the sequence of SEQ ID NO: 3. Thus, another embodiment of the present invention is the isolated microRNA designated microRNA-181d-5p, comprising the sequence and the use of the isolated microRNA designated microRNA-181d-5p, comprising the sequence:

(SEQ ID NO: 3)
5'-aacauucauuguugucggugggu-3'

Further embodiments of the invention are isolated microRNAs with sequence homology or similarity to SEQ ID NOs: 1, 2, or 3 sufficient to maintain the function of binding to the 3' UTR of the MAPT gene and the use of an isolated microRNA with sequence homology or similarity to SEQ ID NOs: 1, 2, or 3 sufficient to maintain the function of binding to the 3'UTR of the MAPT gene.

A further embodiment of the present invention is an isolated DNA which encodes the microRNA comprising SEQ ID NOs: 1, 2 or 3, and the use of an isolated DNA which encodes the microRNA comprising SEQ ID NOs: 1, 2, or 3.

Yet a further embodiment of the invention is an isolated DNA which encodes an RNA with sequence homology or similarity to SEQ ID NOs: 1, 2, or 3, sufficient to maintain the function of binding to the 3'UTR of the MAPT gene and the use of an isolated DNA which encodes an RNA with sequence homology or similarity to SEQ ID NOs: 1, 2, or 3 sufficient to maintain the function of binding to the 3'UTR of the MART gene.

The present invention also includes recombinant constructs comprising the RNA or the DNA encoding the microRNA having the nucleotide sequence of SEQ ID NOs: 1, 2, or 3, and a vector that can be expressed in a transformed host cell. The present invention also includes the host cells transformed with the recombinant construct comprising the microRNA or DNA encoding the microRNA having the nucleotide sequence of SEQ ID NOs: 1, 2, or 3, and a vector.

The present invention also includes recombinant constructs comprising an RNA with sequence homology to SEQ ID NOs: 1, 2, or 3 sufficient to maintain the function of binding to the 3'UTR of the MAPT gene or the DNA encoding the microRNA with sequence homology to SEQ ID NOs: 1, 2, or 3, sufficient to maintain the function of binding to the 3'UTR of the MAPT gene and a vector that can be expressed in a transformed host cell. The present invention also includes the host cells transformed with the recombinant construct comprising this microRNA or DNA and a vector.

The present invention also includes the use of the antisense microRNA or DNA of the nucleotide sequence comprising SEQ ID NOs: 1, 2, or 3.

The present invention also includes recombinant constructs comprising the antisense microRNA or the DNA encoding the antisense microRNA having the nucleotide sequence of SEQ ID NOs: 1, 2, or 3, and a vector that can be expressed in a transformed host cell. The present invention also includes the host cells transformed with the recombinant construct comprising the antisense microRNA or DNA encoding the antisense microRNA having the nucleotide sequence of SEQ ID NO: 1, 2, or 3, and a vector.

A further embodiment of the invention is microRNA that binds to the 3'UTR designed from the sequences comprising SEQ ID NOs: 4-8 and the use of microRNA that binds to the 3'UTR designed from the sequences comprising SEQ ID NOs: 4-8.

A further embodiment of the present invention is an isolated DNA which encodes the microRNA that binds to the 3'UTR designed from the sequences comprising SEQ ID NOs: 4-8 and the use of an isolated DNA which encodes the microRNA that binds to the 3'UTR designed from the sequences comprising SEQ ID NOs: 4-8.

The present invention also includes recombinant constructs comprising the microRNA or the DNA encoding the microRNA that binds to the 3'UTR designed from the sequences comprising SEQ ID NOs: 4-8 and a vector that can be expressed in a transformed host cell. The present invention also includes the host cells transformed with the recombinant construct comprising the microRNA or DNA encoding the microRNA that binds to the 3'UTR designed from the sequences comprising SEQ ID NOs: 4-8 and a vector.

The present invention also includes the use of the antisense microRNA or DNA of the nucleotide sequence that binds to the 3'UTR designed from the sequences comprising SEQ ID NOs: 4-8.

The present invention also includes recombinant constructs comprising the antisense microRNA or the DNA encoding the antisense microRNA that binds to the 3'UTR designed from the sequences comprising SEQ ID NOs: 4-8, and a vector that can be expressed in a transformed host cell. The present invention also includes the host cells transformed with the recombinant construct comprising the antisense microRNA or DNA encoding the antisense microRNA that binds to the 3'UTR designed from the sequences comprising SEQ ID NOs: 4-8, and a vector.

It will also be understood that any of the methods for treatment, prevention, diagnosis or screening of the present invention that utilizes microRNA can also utilize a microRNA mimic. microRNA mimics are molecules designed for gene silencing approaches and contain non-natural or artificial double stranded microRNA-like RNA fragments, that can bind to the 3'UTR of the MAPT gene.

Increasing MicroRNA as a Treatment for AD and TPD and Other Tauopathies

As shown herein, patients suffering from AD and TPD have low levels of microRNA that binds to the 3'UTR of the MAPT gene, allowing the increased expression of tau, leading to pathological tau accumulation. Thus, increasing microRNA that binds to the 3'UTR of the MAPT gene would decrease this overexpression of tau.

Thus, an embodiment of the present invention is the treatment or prevention of tauopathies, including but not limited to Alzheimer's disease and tangle-predominant dementia, as well as progressive supranuclear palsy, chronic traumatic encephalopathy, frontotemporal dementia with Parkinsonism linked to chromosome 17 (FTLD-tau), frontotemporal dementia, ganglioglioma, gangliocytoma, meningioangiomatosis, Pick's disease, and corticobasal degeneration, by increasing microRNA that binds to the 3'UTR of the tau mRNA derived from the tau MAPT gene in a subject in need thereof. It will be understood by those of skill in the art that any microRNA that is differentially expressed in tauopathies, including those listed in Table 11-16 can be increased and used to prevent and treat tauopathies. Additionally microRNAs that target the 3'UTR of the tau MAPT gene such as those listed in Tables 3-6 could also be increased and used to prevent and treat tauopathies.

Preferred microRNAs that can be increased and used in the method are miR-34c-5p, miR-132-3p, miR-27a-5p, miR-204-5p, miR-485-5p, miR-181b-5p, miR-181d-5p, and miR-219-5p.

In a preferred embodiment, the microRNA used is the one designated miR-219-5p comprising the sequence of SEQ ID NO: 1. In another preferred embodiment, the microRNA comprises a nucleotide sequence with similarity or homology to SEQ ID NO: 1 sufficient to maintain the function of binding to the 3'UTR of the tau mRNA derived from the tau MAPT gene. In another preferred embodiment, the microRNA used is the one designated miR485-5p comprising the sequence of SEQ ID NO: 2. In another preferred embodiment, the microRNA comprises a nucleotide sequence with similarity or homology to SEQ ID NO: 2 sufficient to maintain the function of binding to the 3'UTR of the tau mRNA derived from the tau MAPT gene. In another preferred embodiment, the microRNA used is the one designated miR181d comprising the sequence of SEQ ID NO: 3. In another preferred embodiment, the microRNA comprises a nucleotide sequence with similarity or homology to SEQ ID NO: 3 sufficient to maintain the function of binding to the 3'UTR of the tau mRNA derived from the tau MAPT gene.

Although this microRNA and others are found in higher levels in patients with tauopathies, including AD and TPD, as discussed above, this is because the patient is reacting the overproduction of tau and any microRNA that targets the 3'UTR of the MAPT gene can be used to prevent and/or treat tauopathies.

In another embodiment, the microRNA can comprise a nucleotide sequence that would bind to the 3'UTR of the tau mRNA derived from the tau MAPT gene and regulate tau expression. Such microRNA can be designed using the known sequence of the 3'UTR of the MAPT gene, and in particular sequences with the nucleotide sequences comprising SEQ ID NOs 4-8.

The increase of microRNA can be accomplished different ways.

One method of increasing the microRNA in a subject in need thereof would be to administer a therapeutically effective amount of an agent to the subject, wherein the agent increases microRNA production.

Another method of increasing the microRNA that binds to the 3'UTR of the tau mRNA derived from the tau MAPT gene is by administering an agent that increases or maximizes the ability of the microRNA to bind to its target.

A further method of increasing microRNA in a subject in need thereof would be to administer a microRNA or microRNA mimic that binds to the 3'UTR of the tau mRNA derived from the tau MAPT gene to the subject, or a microRNA or microRNA mimic that is differentially expressed in AD or TPD.

This can be accomplished using a microRNA that is designed to maintain the function of this microRNA in that it can bind to the 3'UTR of the tau mRNA derived from the tau MAPT gene. This microRNA can be made by recombinant methods known in the art. The microRNA can also be modified for increasing other desirable properties, such as increased stability, decreased degradation in the body, and increased cellular uptake.

One such method for delivering the RNA is receptor mediated endocytosis where the RNA is coupled to a targeting molecule that can bind to a specific cell surface receptor, inducing endocytosis and transfer of the RNA into cells. Coupling is normally achieved by covalently linking poly-lysine to the receptor molecule and then arranging for (reversible) binding of the negatively charged RNA to the positively charged poly-lysine component. Another approach utilizes the transferrin receptor or folate receptor which is expressed in many cell types. When producing the microRNA for this method of administration, the microRNA could be manufactured to have a guide strand which is identical to the microRNA of interest and a passenger strand that is modified and linked to a molecule for increasing cellular uptake. In particular, a ligand-receptor pair that is particular to neurons would be useful in the current invention.

Thus, a preferred embodiment of the present invention is a microRNA or microRNA mimic including those comprising the nucleotide sequence of SEQ ID NOs: 1, 2, or 3, or with a nucleotide sequence sufficient to maintain the function of binding to the 3'UTR of the tau mRNA derived from the tau MAPT gene, or designed using the known sequence of the 3'UTR of the MAPT gene, in particular sequences with the nucleotide sequences comprising SEQ ID NOs 4-8, linked to a ligand or conjugate that increases cellular uptake of the RNA. This conjugation can take place at the terminal positions 5'/3'-OH but the ligands may also take place at the sugars and/or the bases. Examples of conjugates/ligands that can be linked to the microRNA molecule for include, but are not limited to, transferrin, folate, cholesterol moieties, duplex intercalators such as acridine, poly-L-lysine, and phosphoromonothioate.

Another method to administer the RNA to the proper tissue is direct injection/particle bombardment, where the RNA is be injected directly with a syringe and needle into a specific tissue, such as muscle.

An alternative direct injection approach uses particle bombardment ('gene gun') techniques: RNA is coated on to metal pellets and fired from a special gun into cells. Successful gene transfer into a number of different tissues has been obtained using this approach. Such direct injection techniques are simple and comparatively safe.

Another method for delivery of microRNA to the proper tissue or cell is by using adeno-associated viruses (AAV). microRNA delivered in these viral vectors is continually expressed, replacing the expression of the microRNA that is not expressed in the subject. Also, AAV have different serotypes allowing for tissue-specific delivery due to the natural tropism toward different organs of each individual AAV serotype as well as the different cellular receptors with which each AAV serotype interacts. The use of tissue-specific promoters for expression allows for further specificity in addition to the AAV serotype.

Other mammalian virus vectors that can be used to deliver the RNA include oncoretroviral vectors, adenovirus vectors, Herpes simplex virus vectors, and lentiviruses.

In particular, HSV vectors are tropic for the central nervous system (CNS) and can establish lifelong latent infections in neurons and thus, are a preferred vector for use in this invention.

Thus, a further preferred embodiment of the present invention is a microRNA or microRNA mimic including those comprising the nucleotide sequence of SEQ ID NOs: 1, 2, or 3, or with a nucleotide sequence sufficient to maintain the function of binding to the 3'UTR of the tau mRNA derived from the tau MAPT gene, or designed using the known sequence of the 3'UTR of the MAPT gene, in particular sequences with the nucleotide sequences comprising SEQ ID NOs 4-8, packaged in a virus vector.

Liposomes are spherical vesicles composed of synthetic lipid bilayers which mimic the structure of biological membranes. The RNA to be transferred is packaged in vitro with the liposomes and used directly for transferring the RNA to a suitable target tissue in vivo. The lipid coating allows the RNA to survive in vivo, bind to cells and be endocytosed into the cells. Cationic liposomes (where the positive charge on liposomes stabilize binding of negatively charged DNA), have are one type of liposome.

The microRNAs can also be administered with a lipid to increase cellular uptake. The microRNA may be administered in combination with a cationic lipid, including but not limited to, lipofectin, DOTMA, DOPE, and DOTAP.

Other lipid or liposomal formulations including nanoparticles and methods of administration have been described as for example in U.S. Patent Publication 2003/0203865, 2002/0150626, 2003/0032615, and 2004/0048787. Methods used for forming particles are also disclosed in U.S. Pat. Nos. 5,844,107, 5,877,302, 6,008,336, 6,077,835, 5,972,901, 6,200,801, and 5,972,900.

Thus, a further embodiment of the present invention is a microRNA or microRNA mimic including those comprising the nucleotide sequence of SEQ ID NOs: 1, 2, or 3, or with a nucleotide sequence sufficient to maintain the function of binding to the 3'UTR of the tau mRNA derived from the tau MAPT gene, or designed using the known sequence of the 3'UTR of the MAPT gene, in particular sequences with the nucleotide sequences comprising SEQ ID NOs 4-8, packaged in a liposome. Another embodiment of the present invention is a microRNA or microRNA mimic comprising the nucleotide sequence of SEQ ID NOs: 1, 2, or 3, or with a nucleotide sequence sufficient to maintain the function of binding to the 3'UTR of the tau mRNA derived from the tau MAPT gene, or designed using the known sequence of the 3'UTR of the MAPT gene, in particular sequences with the nucleotide sequences comprising SEQ ID NOs 4-8, combined with a lipid.

A further embodiment of the present invention is a pharmaceutical composition comprising a microRNA or microRNA mimic, including miRNA comprising the nucleotide sequence of SEQ ID NOs: 1, 2, or 3, or with a nucleotide sequence sufficient to maintain the function of binding to the 3'UTR of the tau mRNA derived from the tau MAPT gene, or designed using the known sequence of the 3'UTR of the MAPT gene, in particular sequences with the nucleotide sequences comprising SEQ ID NOs: 4-8, and a pharmaceutically acceptable, diluent, carrier or adjuvant. Adjuvants can also be added to the microRNA to protect it from degradation.

For certain embodiments, the microRNA would be targeted to particular tissues or cells. In a preferred embodiment, the tissue is brain or neurological, and the cells are neurons.

A further method for increasing the microRNA in a subject in need thereof would be to administer a DNA that would encode an microRNA that binds to the 3'UTR of the tau mRNA derived from the tau MAPT gene, to the subject.

This can be accomplished by the methods outlined above to deliver the DNA in vivo, wherein the DNA expresses the microRNA, including those miRNAs comprising SEQ ID Nos: 1, 2, or 3, and/or those that bind to the 3'UTR of the tau mRNA derived from the tau MAPT gene.

Classical gene therapies normally require efficient transfer of cloned genes into disease cells so that the introduced genes are expressed at suitably high levels. Following gene transfer, the inserted genes may integrate into the chromosomes of the cell, or remain as extrachromosomal genetic elements (episomes).

For the former situation, the DNA recombines with the endogenous gene that produces the microRNA present in the cell. Such recombination requires a double recombination event which results in the correction of the mutation in the gene producing the microRNA.

The more preferred situation is that the gene will be expressed by the cell from an extrachromosomal location.

Vectors for introduction of the DNA in either recombination or extrachromosomal reproduction are known in the art and have been discussed herein. Methods for introduction of genes into cells including electroporation, calcium phosphate co-precipitation, and viral transduction are known in the art.

Use of microRNA as a Screen or Diagnosis for Tauopathies, Especially AD and/or TPD As stated above, and shown in Example 3, low levels of microRNA, designated miR-219-5p with the nucleotide sequence comprising SEQ ID NO: 1, is associated with higher levels of tau, which in turn signals a tauopathy. Thus, one embodiment of the present invention is the screening, diagnosis or identification of a tauopathy in a subject, by detection of decreased levels microRNA, designated miR-219-5p with the nucleotide sequence comprising SEQ ID NO: 1, in a sample from a subject. In particular, because cognitive impairment can be caused by many other diseases and disorders other than AD and TPD, this method is particularly useful for screening for, identifying and diagnosing AD and/or TPD in a subject with cognitive impairment.

Also as shown, an increased level of microRNA, designated miR-181d-5p with the nucleotide sequence comprising SEQ ID NO: 3, is associated with AD and TPD. Thus, one embodiment of the present invention is the screening, diagnosis or identification of a tauopathy in a subject, by detection of increased levels microRNA, designated miR-181d-5p, with the nucleotide sequence comprising SEQ ID NO: 3, in a sample from a subject. In particular, because cognitive impairment can be caused by many other diseases and disorders other than AD and TPD, this method is particularly useful for screening for, identifying and diagnosing AD and/or TPD in a subject with cognitive impairment.

In order to detect one of the microRNAs associated with Alzheimer's disease and tangle-predominant dementia, a biological sample from a subject with cognitive impairment ranging from mild to severe, or with pre-dementia in the prodromal phase is obtained and prepared and analyzed for the presence of the microRNAs. This can be achieved in numerous ways, by a diagnostic laboratory, and/or a health care provider.

The levels of microRNA, designated miR-219-5p and/or miR-181d-5p found in a sample are compared to the levels of these microRNAs in healthy controls. This comparison can be done in many ways. The same assay can be performed simultaneously or consecutively, on a purified and isolated RNA sample from a healthy control and the results compared qualitatively, e.g., visually, i.e., does the RNA sample from the healthy control produce the same intensity of signal as the RNA sample from the subject in the same assay, or the results can be compared quantitatively, e.g., a value of the signal for the RNA sample from the subject is obtained and compared to a known value of the RNA in a healthy control.

Figure 3:
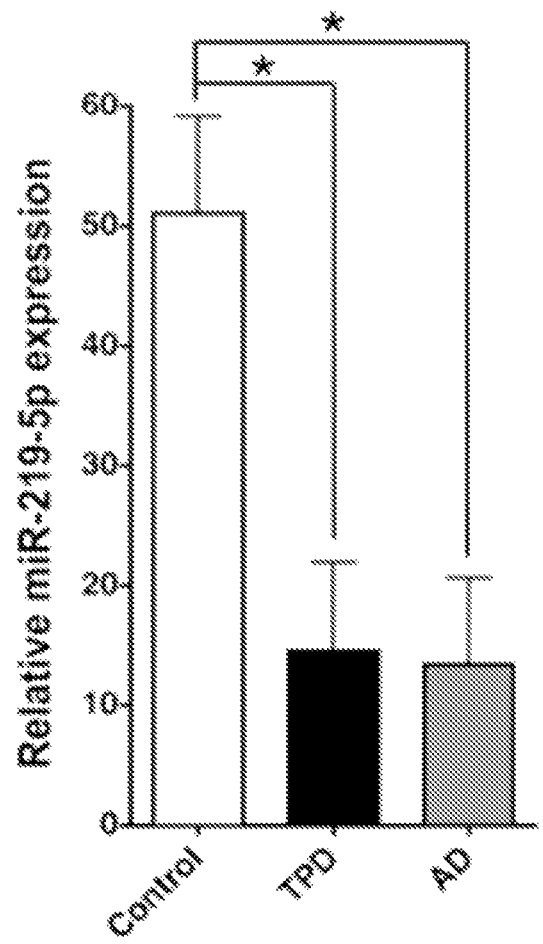
FIG. 3 shows the results of QPCR using a Taqman assays confirming decreased levels of miR-219-5p in TPD (n=19) and AD (n=7) compared to controls (n=20). * p<0.05.

A lower level of microRNA, designated miR-219-5p in a sample from a subject as compared to the healthy control would indicate the subject has tauopathy. If the subject has MCI, it would indicate the subject has AD or TPD. As shown in FIG. 3, there is a significant difference (about 5 times more) in miR-219 levels in control subjects as compared to AD or TPD. Also as set forth in Table 3, there is a fold change of −1.4 for this miRNA in TPD versus controls, and a fold change of −1.9 for this miRNA in AD versus controls.

A higher level of microRNA, designated miR-181d in a sample from a subject as compared to the healthy control would indicate the subject has tauopathy. If the subject has MCI, it would indicate the subject has AD or TPD. As set forth in Table 3, there is a fold change of +0.8 for this miRNA in TPD versus controls, and a fold change of +0.6 for this miRNA in AD versus controls.

Moreover, the miRNAs listed in Table 3 including miR-185, miR-151-5p, and the miRNAs listed in Tables 11 and 13 can be used in a method similar to one for miR219-5p as these miRNAs are found in lower levels in AD and TPD versus controls. The microRNAs listed in Table 3 including miR-149 and those listed in Tables 12 and 14 can be used in a method similar to one for miR-181 as these miRNAs are found in higher levels in AD and TPD patients versus controls. Finally, miRNAs listed in Tables 15 and 16 can be used in diagnosing or identifying AD from TPD in that these miRNAs are differentially expressed in these patients.

Any method that detects microRNA can be used to screen for, diagnose, predict, and identify AD or TPD in a subject with cognitive impairment utilizing the surprising discoveries of the association of microRNAs with AD and TPD.

Methods for screening for and diagnosing AD or TPD in a patient with cognitive impairment ranging from mild to severe, or with pre-dementia in the prodromal phase, begin by obtaining a sample of biological tissue or bodily fluid from the patient and extracting, isolating and/or purifying the nucleic acid (e.g., genomic DNA, cDNA, RNA) from the tissue or fluid.

The nucleic acid can be obtained from any biological tissue. Preferred biological tissues include, but are not limited to, brain, epidermal, whole blood, and plasma.

The nucleic acid can be obtained from any bodily fluid. Preferred bodily fluids include, but are not limited to, cerebrospinal fluid, plasma, saliva, sweat, and urine.

The nucleic acid is extracted, isolated and purified from the cells of the tissue or fluid by methods known in the art. Many protocols have been developed for the extraction of high-quality RNA using various kits and reagents. Although it is possible to use total RNA for microarray analysis, because small RNAs only make up approximately 0.01% of all RNAs, microRNA enrichment increases sensitivity.

Methods for detecting microRNA include but are not limited to Northern blots, in situ hybridization, real time PCR, nuclease protection assays, poly-A tailed reverse transcription, microRNA amplification profiling, microRNA serial analysis of gene expression, microarrays, enzyme amplified assays, sequencing, and nanoparticle methods.

One useful technique for determining whether the microRNAs are present in a sample from a subject is small RNA sequencing and annotation using barcoded small RNA cDNA libraries and generating microRNA expression profiles of the sample, as exemplified in Examples 1.

Next generation sequencing platforms such as Genome Analyzer (Illumina Inc) or Genome Sequencer FLX (454 Life Science and Roche Applied Science) are also useful to detect microRNA by sequencing. Deep sequencing uses massively parallel sequencing, generating millions of small RNA sequence reads from a given sample.

When a probe is to be used to detect the presence of the microRNAs, the biological sample that is to be analyzed must be treated to extract the nucleic acids. The nucleic acids to be targeted usually need to be at least partially single-stranded in order to form a hybrid with the probe sequence. It the nucleic acid is single stranded, no denaturation is required. However, if the nucleic acid to be probed is double stranded, denaturation must be performed by any method known in the art.

The nucleic acid to be analyzed and the probe are incubated under conditions which promote stable hybrid formation of the target sequence in the probe and the target sequence in the nucleic acid. The desired stringency of the hybridization will depend on factors such as the uniqueness of the probe in the part of the genome being targeted, and can be altered by washing procedure, temperature, probe length and other conditions known in the art, as set forth in Maniatis et al. (1982) and Sambrook et al. (1989).

Labeled probes are used to detect the hybrid, or alternatively, the probe is bound to a ligand which labeled either directly or indirectly. Suitable labels and methods for labeling are known in the art, and include biotin, fluorescence, chemiluminescence, enzymes, and radioactivity.

Assays using such probes include Northern blot analysis. After transferring these small RNAs from the gel onto a membrane, the RNA is fixed onto the membrane by UV crosslinking and/or baking the membrane. Because of the small size and the low abundance of microRNA molecules, the use of an oligonucleotide probe with increased sensitivity is essential to detect the microRNA. The ability of the Northern blot probe to distinguish between related microRNAs depends on the level of sequence homology and the position of the base mismatch(es). If the base mismatches are distributed across the length of the microRNA sequence, 3-bp mismatches are sufficient to confer probe specificity.

Dot-blot hybridization can also be used to screen for the microRNAs. Nucleic acid including RNA is obtained from the subject with suspected AD or TPD, denatured and spotted onto a nitrocellulose or nylon membrane and allowed to dry. The membrane is exposed to a solution of labeled single stranded probe sequences and after allowing sufficient time for probe-target heteroduplexes to form, the probe solution is removed and the membrane washed, dried and exposed to an autoradiographic film. A positive spot is an indication of the target sequence in the RNA of the subject and a no spot an indication of the lack of the target sequence in the RNA of the subject.

In situ hybridization (ISH) can also be used to detect microRNA using probes. ISH does not require the isolation or electrophoretic separation of RNA. Hybridization of the probe takes place within the cell or tissue. Since cellular structure is maintained throughout the procedure, ISH provides information about the location of mRNA within the tissue sample.

ISH is performed by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

Nuclease protection assays can also be used to detect the microRNA. This assay (including both ribonuclease protection assays and S1 nuclease assays) is an extremely sensitive method for the detection and quantitation of specific microRNAs. The basis of the nuclease protection assay is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 µg of sample RNA, compared with the 20-30 µg maximum of blot hybridizations.

RNA microarrays can also be used to screen for the microRNAs. The surfaces involved are glass rather than porous membranes and similar to reverse dot-blotting, the RNA microarray technologies employ a reverse nucleic acid hybridization approach: the probes consist of unlabeled DNA fixed to a solid support (the arrays of DNA or oligonucleotides) and the target is labeled and in solution.

Microarray analysis allows for parallel analysis of large numbers of microRNAs and can be used to detect the presence and/or regulation of a wide range of defined microRNAs. After extracting RNA, the mature microRNAs can be directly labeled, usually by using T4 RNA ligase, to attach 1 or 2 fluorophore-labeled nucleotides to the 3' end of the microRNA Microarray technology also permits an alternative approach to RNA sequencing by permitting by hybridization of the target RNA to a series of oligonucleotides of known sequence, usually about 7-8 nucleotides long. If the hybridization conditions are specific, it is possible to check which oligonucleotides are positive by hybridization, feed the results into a computer and use a program to look for sequence overlaps in order to establish the required DNA sequence. RNA microarrays have permitted sequencing by hybridization to oligonucleotides on a large scale.

Another preferred and commonly used technique for determining whether microRNA is present in a sample is the use of real-time PCR. This is exemplified in Example 13.

A microRNA real-time reaction stalls with reverse transcribing RNA into cDNA. The limited length of the mature microRNA (approximately 22 nt), the lack of a common sequence feature like a poly(A) tail, and the fact that the mature microRNA sequence is also present in the pri- and pre-microRNA transcript pose several challenges for appropriate reverse transcription. However, to date, mainly two different methods are used for the reverse transcription: microRNA-specific or universal reverse transcription. In the first approach, microRNAs are reverse transcribed individually by using stem-loop-specific reverse transcription primers. Stem-loop primers are designed to have a short single-stranded region that is complementary to the known sequence on the 3' end of the microRNA, a double-stranded part (the stem), and the loop that contains the universal primer-binding sequence. The resulting cDNA is then used as a template for quantitative (q)PCR with 1 microRNA-specific primer and a second universal primer (TaqMan PCR, Applied Biosystems). Stem-loop primers are more difficult to design, but their structure reduces annealing of the primer to pre- and pri-microRNAs, thereby increasing the specificity of the assay. This technique is exemplified in Example 3.

The second approach first tails all microRNAs with a common sequence and then reverse transcribes the microRNA by using a universal primer. This approach is widely used and especially useful if several different microRNAs need to be analyzed from a small amount of starting material. The 3' ends of all microRNAs are elongated with a poly(A) tail using *Escherichia coli* poly(A) polymerase (miRCURY, Exiqon). A primer consisting of an oligo(dT) sequence with a universal primer-binding sequence at its 5' end is then used to prime reverse transcription and to amplify the target sequences in the qPCR reaction. The stretch of "dTs" between the microRNA and the universal sequence of the oligo(dT) primer is defined by using a template binding sequence at the 5' end of the primer that anchors the primer to the 3' end of the microRNA.

Another new technique that can be used to detect microRNA called "optical liquid stamping" works by imprinting microparticle structures onto photosensitive fluids. The resulting three-dimensional hydrogel particles, encoded with unique "barcodes," can be used for the detection of microRNAs across large numbers of samples. These particles are custom-designed for readout in virtually any flow cytometer. A commercial product, FirePlex miRSelect, using this technique is available.

Kits

It is contemplated that all of the diagnostic and screening assays disclosed herein can be in kit form for use by a health care provider and/or a diagnostic laboratory.

Diagnostic and screening assays based upon miRNA would include for example, probes for miRNA, such as those designated miR-219 and miR-181-d, reagents for isolating and purifying nucleic acids from biological tissue or bodily fluid, reagents for performing assays on the isolated and purified nucleic acid, instructions for use, and comparison sequences could be included in a kit for detection of the miRNAs. These kits could also include primers specific for the MART 3'UTR.

Drug Screening and Research Tools

A further embodiment of the invention is the use of the microRNA and its binding site on the 3'UTR of the tau mRNA derived from the tau MART gene and the methods set forth herein as a method for screening for potential therapies for tauopathies, especially Alzheimer's disease and tangle-predominant dementia.

In one embodiment, the DNA or mRNA comprising the 3'UTR of the tau mRNA derived from the tau MAPT gene is used, and more specifically the conserved region to which microRNA binds to regulate tau synthesis, and more specifically the region to which miR-219-5p binds.

In this assay to screen for potential therapeutics for tauopathies, including AD and/or TPD, an agent is contacted with DNA or RNA as described above, and a complex between the DNA or RNA and the agent is detected by methods known in the art. One such method is labeling the DNA or RNA and then separating the free DNA or RNA from that bound to the agent. If the agent binds to the DNA or RNA, the agent would be considered a potential therapeutic for AD and/or TPD, or other tauopathies.

Additionally, the 3' UTR of the tau mRNA derived from the tau MART gene can be amplified using primers such as those comprising the nucleotide sequence of SEQ ID NOs: 9, 10, 13, and 14, and cloned into any of the vectors described herein by the methods described herein. The recombinant constructs of the 3'UTR and vector can also have a means to measure expression of the 3'UTR such as a reporter construct. Such constructs include but are not limited to those exemplified in Example 4, a dual luciferase reporter gene psiCHECK-2 vector. The 3'UTR can also be linked to another gene with a measurable phenotype, such as tau, as exemplified in Example 5.

These recombinant constructs can be transfected into any host cell described herein, by the methods described herein. Host cells include but are not limited to neuroblastoma cells and hippocampal cells.

The host cells with the recombinant constructs can then be used for screening for therapeutic agents for AD and/or TPD. In this embodiment, the expression of the 3'UTR is measured by the expression of the linked gene prior to the contact with the agent. The transformed host cells are then contacted with the agent, and if the expression of the gene linked to the 3'UTR decreases, then the agent is binding to the 3'UTR blocking expression and can be considered a potential therapy for AD and/or TPD.

In this method the 3'UTR DNA or RNA in the recombinant construct can also be mutated to delete the conserved binding site of miR-219-5p or another miRNA known to target the 3'UTR of tau, and used in a drug screening assay. If after contact with an agent that decreased expression in the recombinant construct with the entire 3'UTR, the expression of the linked gene does not decrease, the agent can be considered to bind to the 3'UTR at the conserved site of binding of miR-219-5p. Since it has been shown herein that this binding decreases the expression of tau, any agent that binds to this region of the 3'UTR of the MAPT gene, can be considered a therapeutic for diseases and disorders resulting from the overexpression of tau.

Any of the constructs and transformed host cells can also be used for basic research related to AD, TPD, and other tauopathies. For instance, these constructs and cells can be used to measure the effects of naturally occurring substances on the 3'UTR of the tau mRNA derived from the tau MAPT gene, such as A3 peptide or neuron growth factor.

These gene constructs as well as the host cells transformed with these gene constructs can also be the basis for transgenic animals for testing both as research tools and for therapeutic agents. Such animals would include but are not limited to, nude mice and *Drosophila*. Phenotypes can be correlated to the genes and looked at in order to determine the genes effect on the animals as well as the change in phenotype after administration or contact with a potential therapeutic agent.

Additionally, host cells and animals that overexpress or under express microRNA that bind to the 3'UTR of the tau mRNA derived from the tau MAPT gene are also contemplated by the invention and are useful in both screening for therapeutic agents, as well as basic research. This is exemplified in Example 7 with *Drosophila melanogaster* that overexpress miR-219. These flies have a different wing phenotype and are weak in flight muscles as compared to their control counterparts, as shown by the negative geotaxis assay. A test agent could be administered to or contacted with these flies and the phenotypes determined. Additionally, a test agent could be administered to the control flies and if their phenotype became more similar to the flies overexpressing the miR-219, i.e., climbing less high and/or wings up phenotype, the test agent could be considered as increasing microRNA that binds to the 3'UTR of the tau mRNA derived from the tau gene, and is a potential therapeutic for tauopathies, including AD and TPD.

Animals that have an overexpression of tau with an identifiable phenotype, such as transgenic flies with rough eye phenotype, exemplified in Example 10, can also be used to screen for therapeutic and prophylactic agents, as well as be used for basic research. As shown in the Examples, miR-219 rescued this phenotype associated with tau toxicity.

EXAMPLES

The present invention may be better understood by reference to the following non-limiting examples, which are presented in order to more fully illustrate the preferred embodiments of the invention. They should in no way be construed to limit the broad scope of the invention.

Example 1—MicroRNA Expression in Post-Mortem Alzheimer's Disease, Tangle-Predominant Dementia and Control Brains Materials and Methods Patient samples were de-identified fresh frozen human autopsy brain tissue (Table 1) from the frontal cortex (Broadmann area 9), obtained from the New York Brain Bank at Columbia University, University of Kentucky (Lexington, Ky., USA), the University of California San Diego (San Diego, Calif., USA), the Banner Sun Health Research Institute (Sun City, Ariz., USA) and the University of Washington (Seattle, Wash., USA).

RNA isolation was obtained by pulverizing fresh-frozen brain tissue in liquid nitrogen, lysed in QIAzol and homogenized using a QIAshredder column. Total RNA was extracted using the miRNeasy Kit (Qiagen, Valencia, Calif.). A subset of total RNA samples were purified using TRIzol and similar results were obtained (Invitrogen/Life Technologies, Carlsbad, Calif.). RNA was assessed on an Agilent 2100 Bioanalyzer system using the Agilent RNA 6000 Nano Assay kit and a Nanodrop Spectrophotometer (Thermoscientific, Waltham, Mass.).

Small RNA sequencing and annotation was performed by using a barcoded small RNA cDNA library and subsequent pooled library preparation steps were prepared from fresh frozen-extracted RNA as previously described in Hafner et al. (2011). MicroRNA expression profiles were generated for all samples in two barcoded sequencing runs. A computer pipeline was used to extract barcodes, align to the genome (hg19) and assign small RNA annotations to the reads. MicroRNA abundance was determined as the sum of all reads with up to two annotation mismatches and presented as the normalized read frequency. Curated definitions were used for microRNA annotation. Heat map generation and data analysis were performed within the R/Bioconductor statistical framework (Gentleman et al. (2004); Anders and Huber (2010)).

Results

MicroRNA expression was profiled in Alzheimer's disease (AD, n=6), tangle-predominant dementia (TPD, n=3), and controls (n=7) (shown in Table 1) using an established small RNA-sequencing protocol as set forth in Hafner et al. (2011). An average of about 12.9 million sequence reads (range=3.8-47.2 million) for each sample were obtained (Table 2). Regression analysis revealed a high degree of correlation among normalized read counts (average r2=0.88, range=0.76-0.96) and all the small RNA classes showed a similar distribution of reads (FIGS. 1A and B). For all subjects, reads were highly enriched for microRNAs, with approximately 86% of the reads mapping to known microRNAs and the remainder mapping to other non-coding small RNAs including tRNA, snoRNA, snRNA, rRNA and piRNA (Table 2).

Figure 2A:
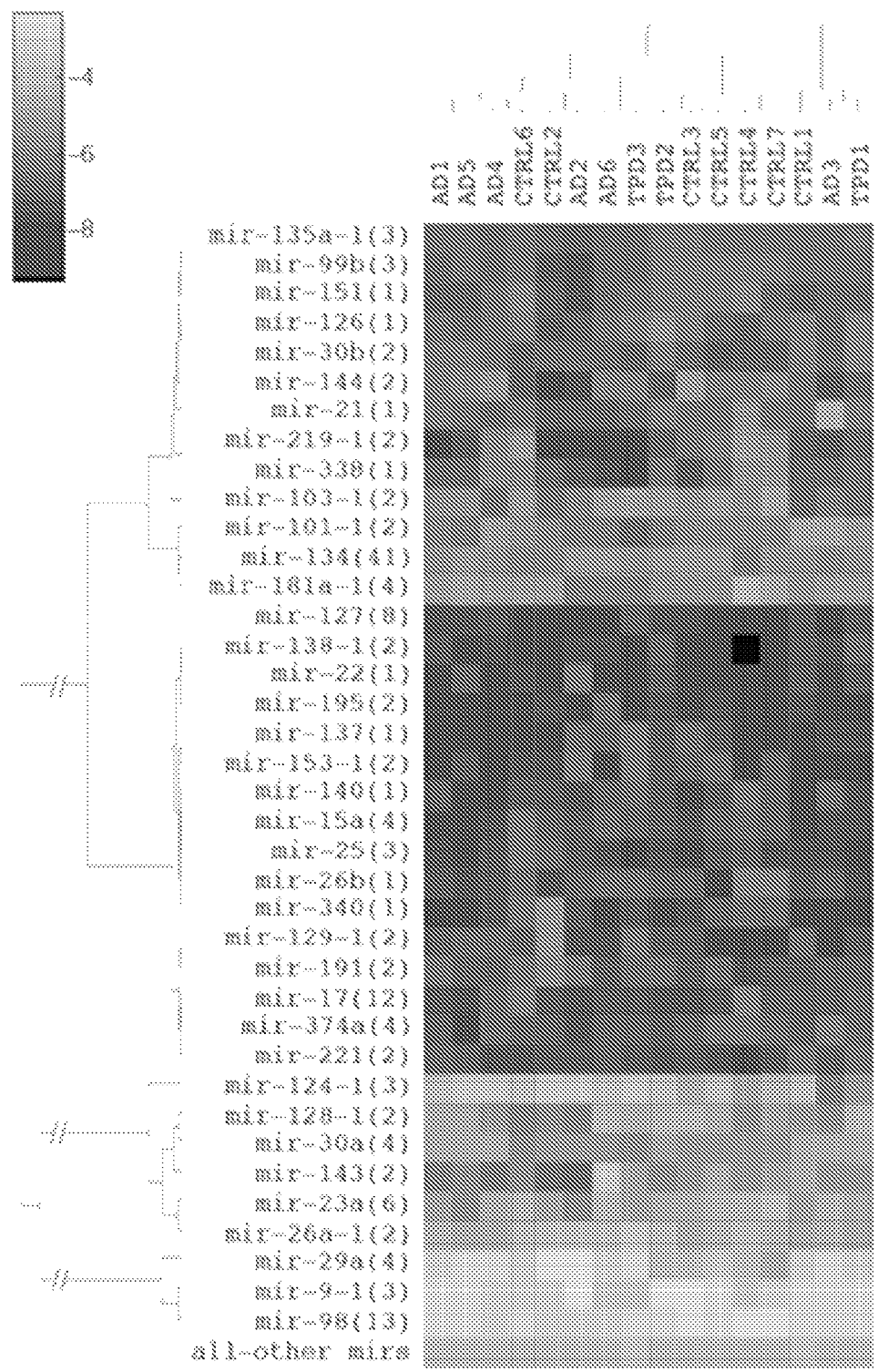
FIG. 2A is a heat map diagram of the small RNA-sequencing with unsupervised hierarchical clustering of microRNA changes in AD (n=6), TPD (n=3) and control (n=7). Data are shown as a pseudo-colored heat map (log 2 transformed relative expression values of the normalized read frequency).
Figure 2B:
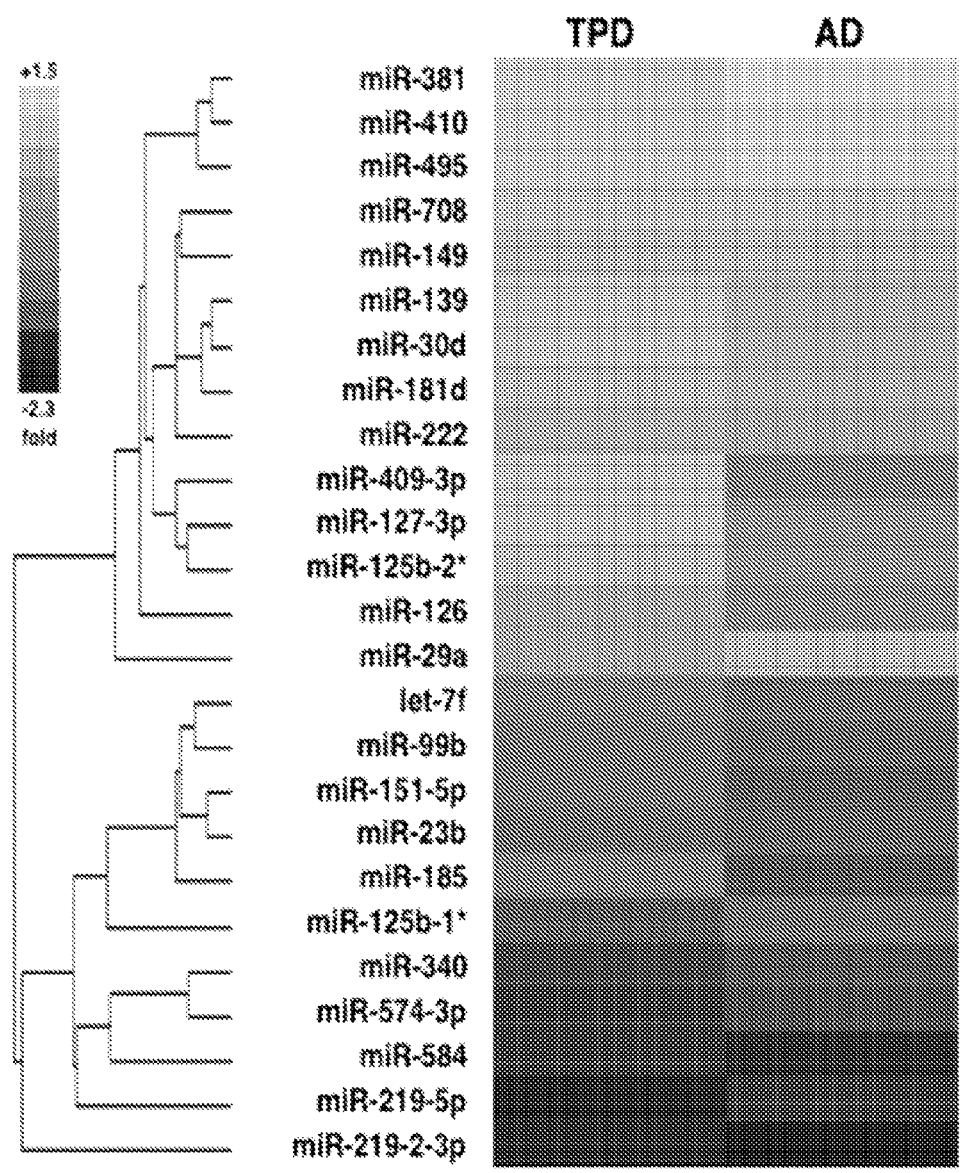
FIG. 2B is a heat map diagram of the small RNA-sequencing with unsupervised hierarchical clustering of microRNA changes in average levels from the most significant 25 microRNAs identified among AD (n=6), TPD (n=3) and control (n=7) (one-way ANOVA, p<0.05, unadjusted).

To generate microRNA signatures, the normalized read frequencies from AD, TPD and controls were compared (FIG. 2A). When ranked by significance, differences in 25 microRNAs among AD, TPD and controls were observed (p<0.05; one-way ANOVA, unadjusted, FIG. 2B). 11 microRNAs were identified that are different between TPD and control, 20 between AD and control, and 6 between TPD and AD. Of the microRNAs identified, only those derived from the mir-219-1 and mir-219-2 precursors are known to be brain-specific (Sempere et al. (2004)). Notably, no difference was seen in the neuronal mir-124, suggesting that the observed differences are not secondary to neuronal loss.

Example 2—Prediction of MAPT Targeting

Materials and Methods

Currently, integration of various computational methods is a common approach to improve prediction accuracy and to create an optimal framework for deciphering biological functions of microRNAs (Zhang and Verbeck (2010)). Of the programs available TargetScan (Friedman et al. (2009); Lewis et al. (2005); Grimson et al. (2007); Garcia et al. (2011)) and miRBase (Kozomara and Griffith-Jones (2011); Griffith-Jones et al. (2008); Griffith-Jones et al. (2006); Griffith-Jones (2004)) were selected. TargetScan, a well-established algorithm of seed and sequence complementarity with conservation of binding sites across multiple species, has been shown to result in the most accurate predictions upon target validation (Back et al. (2008); Selbach et al. (2008)).

TargetScan was used to identify candidate microRNAs that are predicted to bind the tau mRNA 3' UTR (Table 3). TargetScan was also used to identify microRNA families that are broadly conserved in vertebrates (Table 4) and

TABLE 1

Summary of Patient Data

| Classification | n | Sex (M/F) | Average age (yr ± SEM) | Braak NFT | Limbic NFT Frequency | CERAD plaque score | Clinical Diagnosis |
|---|---|---|---|---|---|---|---|
| Control | 20 | 9/11 | 89 ± 4.5 | 0-IV | Sparse | 0-A | Normal |
| TPD | 21 | 4/17 | 89 ± 3.4 | III-IV | Frequent | 0-A | AD or MCI |
| AD | 7 | 3/4 | 93 ± 3.9 | V-VI | Frequent B-C | B-C | AD |

SEM—standard error of the mean;
AD—Alzheimer's disease;
TPD—Tangle-predominant dementia:
MCI—mild cognitive impairment;
CERAD plaque score:
0 = none;
A = sparse;
B = moderate;
C = frequent

TABLE 2

Summary of Small RNA Sequencing Statistics in AD, TPD and Control

| Case | Classification | Total Reads | MicroRNA Reads | % | None Reads | % | rRNA Reads | % | tRNA Reads | % | Other RNA Reads | % | Marker Reads | % |
|---|---|---|---|---|---|---|---|---|---|---|---|---|---|---|
| 1 | AD | 16,013,090 | 13,516,502 | 84.4% | 631,838 | 3.9% | 216,699 | 1.4% | 1,071,952 | 6.7% | 359,765 | 2.2% | 3,435 | 0.02% |
| 2 | AD | 6,964,402 | 6,261,001 | 89.9% | 182,352 | 2.6% | 184,355 | 2.6% | 186,129 | 2.7% | 53,915 | 0.8% | 1,809 | 0.03% |
| 4 | AD | 13,401,542 | 11,839,644 | 88.3% | 490,613 | 3.7% | 140,233 | 1.0% | 647,086 | 4.8% | 127,928 | 1.0% | 4,356 | 0.01% |
| 5 | AD | 11,848,169 | 10,565,866 | 89.2% | 445,991 | 3.8% | 162,432 | 1.4% | 419,594 | 3.5% | 109,690 | 0.9% | 4,166 | 0.04% |
| 6 | AD | 5,515,061 | 4,552,854 | 82.6% | 232,377 | 4.2% | 60,701 | 1.1% | 510,384 | 9.3% | 74,651 | 1.4% | 1,109 | 0.02% |
| 7 | AD | 10,955,968 | 9,321,534 | 85.1% | 546,730 | 5.0% | 148,371 | 1.4% | 592,747 | 5.4% | 142,417 | 1.3% | 3,821 | 0.03% |
| 1 | Control | 6,965,614 | 5,822,543 | 83.6% | 257,263 | 3.7% | 222,735 | 3.2% | 446,921 | 6.4% | 60,513 | 0.9% | 2,390 | 0.03% |
| 2 | Control | 8,642,905 | 7,708,564 | 89.2% | 228,211 | 2.6% | 229,337 | 2.7% | 274,206 | 3.2% | 59,315 | 0.7% | 9,961 | 0.12% |
| 4 | Control | 9,460,257 | 8,382,841 | 88.6% | 244,563 | 2.6% | 251,069 | 2.7% | 339,873 | 3.6% | 100,199 | 1.1% | 5,051 | 0.05% |
| 5 | Control | 8,041,382 | 7,043,196 | 87.6% | 231,342 | 2.9% | 227,777 | 2.8% | 320,541 | 4.0% | 75,385 | 0.9% | 2,579 | 0.03% |
| 6 | Control | 47,219,748 | 38,939,377 | 82.5% | 2,720,085 | 5.8% | 1,141,842 | 2.4% | 2,974,965 | 6.3% | 491,026 | 1.0% | 6,035 | 0.01% |
| 16 | Control | 10,182,030 | 8,722,291 | 85.7% | 348,294 | 3.4% | 394,717 | 3.9% | 410,679 | 4.0% | 108,940 | 1.1% | 4,951 | 0.05% |
| 18 | Control | 5,517,456 | 4,581,894 | 83.0% | 365,643 | 6.6% | 179,489 | 3.3% | 195,525 | 3.5% | 70,389 | 1.3% | 644 | 0.01% |
| 7 | TPD | 7,358,781 | 6,254,750 | 85.0% | 267,537 | 3.6% | 313,761 | 4.3% | 271,358 | 3.7% | 100,916 | 1.4% | 6,708 | 0.09% |
| 15 | TPD | 46,009,737 | 40,915,306 | 88.9% | 2,178,534 | 4.7% | 582,308 | 1.3% | 1,424,294 | 3.1% | 349,222 | 0.8% | 6,140 | 0.01% |
| 18 | TPD | 11,761,875 | 9,848,425 | 83.7% | 409,442 | 3.5% | 434,062 | 3.7% | 708,530 | 6.0% | 118,867 | 1.0% | 4,886 | 0.04% |

AD = Alzheimer disease;
TPD = tangle-predominant dementia;
other RNA = piRNA, snRNA and snoRNA mammals (Table 5) as well as microRNA families that are able to bind a subset of other microtubule associated proteins (Table 6).

Results

Expression profiles obtained in Example 1 were analyzed using a bioinformatics approach for candidate microRNAs that might target the tau mRNA. Of all the microRNAs detected, 9.61% were thought to be brain specific (Sempere et al. (2004)) and 14.13% were predicted to target tau. Among microRNAs that differ significantly among AD, TPD and controls, six were predicted to target tau (Table 3). Two of these, miR-219-5p and miR-181d, both have predicted recognition elements that are broadly conserved among vertebrates within the tau 3' UTR. miR-181d was increased in AD and TPD compared to controls. In contrast, miR-219-5p was decreased in AD and TPD compared to controls.

Two precursors, designated mir-219-1 and mir-219-2, that arise from separate genes on chromosome 6 and 9, respectively, can produce an identical mature miR-219-5p. In the obtained profiles, negligible levels of miR-219-1-3p were obtained, suggesting the differences in the mir-219-2 precursor are responsible for the observed changes in miR-219-5p (Table 7).

The mature miR-219-5p sequence was highly conserved and distinct from miR-219-2-3p, which was not predicted to target tau. In contrast, while the miR-219-5p family (miR-219-515081508-3p/4782-3p) recognition element was not contained in the 3' UTR of other representative microtubule associated proteins, a highly-conserved miR-181 recognition element is found in the MAP1a, MAP1b and MAP2 3' UTRs, suggesting a relative selectivity of miR-219-5p for MAPT-derived transcripts (Table 6). Thus, miR-219-5p is the only highly-conserved microRNA predicted to target tau that was observed to be down-regulated in AD and TPD brain.

TABLE 3

Human Brain microRNAs Differing among TPD, AD and Control that are predicted to target MAPT

| | TargetScan MAPT prediction | | Fold change (log$_2$) | | | p (One-way ANOVA) p | p (Student-Newman-Keuls) | | |
|---|---|---|---|---|---|---|---|---|---|
| microRNA | Conservation | Total Context Score | Aggregate P$_{CT}$ | TPD v. Control | TPD v. AD | AD v. Control | | TPD v. Control | AD v. TPD | AD v. Control |
| miR-185 | Only among mammals | −0.02 | <0.1 | −0.2 | 0.8 | −0.9 | 0.016 | 0.707 | 0.040 | 0.016 |
| miR-151-5p | Poorly | −0.21 | <0.1 | −0.4 | 0.5 | −0.8 | 0.026 | 0.293 | 0.162 | 0.020 |
| miR-219-5p | Broadly among vertebrates | −0.03 | 0.5 | −1.9 | −0.4 | −1.4 | 0.027 | 0.061 | 0.752 | 0.018 |
| miR-149 | Only among mammals | −0.08 | <0.1 | 0.8 | −0.1 | 0.9 | 0.019 | 0.054 | 0.624 | 0.018 |
| miR-181d | Broadly among vertebrates | −0.12 | 0.77 | 0.8 | 0.1 | 0.6 | 0.009 | 0.022 | 0.639 | 0.007 |
| miR-409-3p | Poorly | −0.07 | <0.1 | 0.9 | 1.3 | −0.1 | 0.001 | 0.001 | 0.002 | 0.694 |

Significant values in bold.

TABLE 4 miRNA families broadly conserved among vertebrates that are predicted to silence tau using TargetScan

| | Conserved sites | | | | Poorly conserved sites | | | | Total | |
|---|---|---|---|---|---|---|---|---|---|---|
| miRNA | Total | 8mer | 7mer-m8 | 7mer-A1 | Total | 8mer | 7mer-m8 | 7mer-A1 | Context score | Aggregate PCT |
| miR-132/212/212-3p | 1 | 0 | 1 | 0 | 0 | 0 | 0 | 0 | −0.21 | 0.48 |
| miR-22/22-3p | 0 | 0 | 0 | 0 | 4 | 0 | 2 | 2 | −0.19 | <0.1 |
| miR-34ac/34bc-5p/449abc/449c-5p | 1 | 0 | 1 | 0 | 2 | 1 | 0 | 1 | −0.18 | 0.63 |
| miR-214/761/3619-5p | 0 | 0 | 0 | 0 | 4 | 0 | 3 | 1 | −0.16 | 0.61 |
| miR-27abc/27a-3p | 1 | 0 | 0 | 1 | 0 | 0 | 0 | 0 | −0.12 | 0.6 |
| miR-150/5127 | 0 | 0 | 0 | 0 | 4 | 1 | 0 | 3 | −0.12 | 0.34 |
| miR-181abcd/4262 | 1 | 0 | 1 | 0 | 0 | 0 | 0 | 0 | −0.12 | 0.77 |
| miR-218/218a | 0 | 0 | 0 | 0 | 2 | 1 | 1 | 0 | −0.1 | 0.17 |
| miR-199ab-5p | 0 | 0 | 0 | 0 | 2 | 0 | 2 | 0 | −0.09 | 0.13 |
| miR-93/93a/105/106a/291a-3p/294/295/302abcde/372/373/428/519a/520be/520acd-3p/1378/1420ac | 0 | 0 | 0 | 0 | 1 | 1 | 0 | 0 | −0.08 | <0.1 |
| miR-338/338-3p | 0 | 0 | 0 | 0 | 2 | 0 | 0 | 2 | −0.07 | 0.36 |
| miR-204/204b/211 | 1 | 1 | 0 | 0 | 2 | 0 | 1 | 1 | −0.06 | 0.28 |
| miR-223 | 0 | 0 | 0 | 0 | 1 | 0 | 0 | 1 | −0.06 | 0.2 |
| miR-219-5p/508/508-3p/4782-3p | 1 | 0 | 1 | 0 | 1 | 0 | 0 | 1 | −0.03 | 0.5 |
| miR-96/507/1271 | 0 | 0 | 0 | 0 | 1 | 0 | 1 | 0 | −0.03 | <0.1 |
| miR-144 | 0 | 0 | 0 | 0 | 1 | 1 | 0 | 0 | −0.03 | <0.1 |
| miR-24/24ab/24-3p | 0 | 0 | 0 | 0 | 2 | 0 | 1 | 1 | −0.03 | <0.1 |
| miR-10abc/10a-5p | 0 | 0 | 0 | 0 | 1 | 0 | 0 | 1 | −0.03 | <0.1 |
| miR-503 | 0 | 0 | 0 | 0 | 1 | 0 | 1 | 0 | −0.02 | 0.15 |
| miR-135ab/135a-5p | 0 | 0 | 0 | 0 | 1 | 0 | 1 | 0 | −0.02 | <0.1 |
| miR-146ac/146b-5p | 1 | 0 | 1 | 0 | 0 | 0 | 0 | 0 | −0.02 | <0.1 |
| miR-203 | 0 | 0 | 0 | 0 | 2 | 0 | 0 | 2 | −0.02 | 0.17 |

TABLE 4-continued miRNA families broadly conserved among vertebrates that are predicted to silence tau using TargetScan

| miRNA | Conserved sites | | | | Poorly conserved sites | | | | Total | |
|---|---|---|---|---|---|---|---|---|---|---|
| | Total | 8mer | 7mer-m8 | 7mer-A1 | Total | 8mer | 7mer-m8 | 7mer-A1 | Context score | Aggregate PCT |
| miR-19ab | 0 | 0 | 0 | 0 | 1 | 0 | 0 | 1 | −0.01 | <0.1 |
| miR-101/101ab | 0 | 0 | 0 | 0 | 1 | 0 | 0 | 1 | −0.01 | <0.1 |
| miR-17/17-5p/20ab/20b-5p/93/106ab/427/518a-3p/519d | 0 | 0 | 0 | 0 | 1 | 0 | 0 | 1 | −0.01 | <0.1 |

TABLE 5 miRNA families conserved only among mammals that are predicted to silence tau using TargetScan

| miRNA | Conserved sites | | | | Poorly conserved sites | | | | Total | |
|---|---|---|---|---|---|---|---|---|---|---|
| | Total | 8mer | 7mer-m8 | 7mer-A1 | Total | 8mer | 7mer-m8 | 7mer-A1 | Context score | Aggregate PCT |
| miR-615-3p | 1 | 0 | 1 | 0 | 0 | 0 | 0 | 0 | −0.35 | <0.1 |
| miR-485-5p/1698/1703/1962 | 0 | 0 | 0 | 0 | 6 | 2 | 2 | 2 | −0.21 | <0.1 |
| miR-874 | 1 | 0 | 1 | 0 | 4 | 0 | 3 | 1 | −0.19 | <0.1 |
| miR-370 | 0 | 0 | 0 | 0 | 3 | 0 | 2 | 1 | −0.19 | <0.1 |
| miR-346 | 0 | 0 | 0 | 0 | 1 | 0 | 1 | 0 | −0.19 | <0.1 |
| miR-329/329ab/362-3p | 0 | 0 | 0 | 0 | 1 | 0 | 1 | 0 | −0.19 | <0.1 |
| miR-320abcd/4429 | 0 | 0 | 0 | 0 | 2 | 0 | 1 | 1 | −0.19 | <0.1 |
| miR-197 | 0 | 0 | 0 | 0 | 1 | 0 | 1 | 0 | −0.13 | <0.1 |
| miR-342-3p | 0 | 0 | 0 | 0 | 1 | 0 | 1 | 0 | −0.11 | <0.1 |
| miR-125a-3p/1554 | 0 | 0 | 0 | 0 | 1 | 0 | 1 | 0 | −0.11 | <0.1 |
| miR-149 | 0 | 0 | 0 | 0 | 2 | 0 | 2 | 0 | −0.08 | <0.1 |
| miR-377 | 0 | 0 | 0 | 0 | 1 | 0 | 1 | 0 | −0.05 | <0.1 |
| miR-539/539-5p | 0 | 0 | 0 | 0 | 1 | 0 | 1 | 0 | −0.05 | <0.1 |
| miR-542-3p | 0 | 0 | 0 | 0 | 1 | 0 | 0 | 1 | −0.03 | <0.1 |
| miR-378/422a/378bcdefhi | 0 | 0 | 0 | 0 | 1 | 0 | 1 | 0 | −0.03 | <0.1 |
| miR-876-5p/3167 | 0 | 0 | 0 | 0 | 1 | 1 | 0 | 0 | −0.03 | <0.1 |
| miR-505/505-3p | 0 | 0 | 0 | 0 | 1 | 1 | 0 | 0 | −0.03 | <0.1 |
| miR-335/335-5p | 0 | 0 | 0 | 0 | 1 | 0 | 1 | 0 | −0.02 | <0.1 |
| miR-296-3p | 0 | 0 | 0 | 0 | 1 | 0 | 1 | 0 | −0.02 | <0.1 |
| miR-421 | 0 | 0 | 0 | 0 | 1 | 0 | 1 | 0 | −0.02 | <0.1 |
| miR-758 | 0 | 0 | 0 | 0 | 1 | 0 | 1 | 0 | −0.02 | <0.1 |
| miR-186 | 0 | 0 | 0 | 0 | 1 | 0 | 1 | 0 | −0.02 | <0.1 |
| miR-134/3118 | 0 | 0 | 0 | 0 | 1 | 0 | 1 | 0 | −0.02 | <0.1 |
| miR-185/882/3473/4306/4644 | 0 | 0 | 0 | 0 | 2 | 0 | 0 | 2 | −0.02 | <0.1 |
| miR-136 | 0 | 0 | 0 | 0 | 1 | 0 | 0 | 1 | −0.01 | <0.1 |
| miR-873 | 0 | 0 | 0 | 0 | 1 | 0 | 0 | 1 | −0.01 | <0.1 |
| miR-491-5p | 0 | 0 | 0 | 0 | 1 | 0 | 0 | 1 | −0.01 | <0.1 |

TABLE 6

Comparison of Conserved microRNA Recognition Elements by Family in Selected MAPs

| | MAP1a | MAP1b | MAP2 | MAP4 | MAPT |
|---|---|---|---|---|---|
| miR-181abcd/4262 | + | + | + | − | + |
| miR-27abc/27a-3p | − | + | + | − | + |
| miR-34ac/34bc-5p/449abc/449c-5p | + | + | − | − | + |
| miR-132/212/212-3p | − | − | − | − | + |
| miR-146ac/146b-5p | − | − | − | − | + |
| miR-204/204b/211 | − | − | − | − | + |
| miR-219-5p/508/508-3p/4782-3p | − | − | − | − | + |
| miR-615-3p | − | − | − | − | + |
| miR-874 | − | − | − | − | + |
| miR-186 | − | − | + | + | − |
| miR-214/761/3619-5p | − | − | + | + | − |
| miR-224 | − | + | − | + | − |
| miR-23abc/23b-3p | − | − | − | + | − |
| miR-103a/107/107ab | − | − | − | + | − |
| miR-185/882/3473/4306/4644 | − | − | − | + | − |
| miR-199ab-5p | − | − | − | + | − |

TABLE 6-continued

Comparison of Conserved microRNA Recognition Elements by Family in Selected MAPs

| | MAP1a | MAP1b | MAP2 | MAP4 | MAPT |
|---|---|---|---|---|---|
| miR-494 | − | − | − | + | − |
| miR-9/9ab | + | + | + | − | − |
| miR-26ab/1297/4465 | + | + | + | − | − |
| miR-25/32/92abc/363/363-3p/367 | − | + | + | − | − |
| miR-93/93a/105/106a/291a-3p/294/295/302abcde/372/ | − | + | + | − | − |
| miR-124/124ab/506 | − | + | + | − | − |
| miR-130ac/301ab/301b/301b-3p/454/721/4295/3666 | − | + | + | − | − |
| miR-143/1721/4770 | − | + | + | − | − |
| miR-148ab-3p/152 | − | + | + | − | − |
| miR-150/5127 | − | + | + | − | − |
| miR-182 | − | + | + | − | − |
| miR-194 | − | − | + | − | − |
| miR-200bc/429/548a | − | − | + | − | − |
| miR-335/335-5p | − | − | + | − | − |
| miR-361-5p | − | − | + | − | − |
| miR-374ab | − | − | + | − | − |
| miR-488 | − | − | + | − | − |
| miR-539/539-5p | − | − | + | − | − |
| miR-544/544ab/544-3p | − | − | + | − | − |
| miR-590-3p | − | − | + | − | − |
| miR-1ab/206/613 | + | + | − | − | − |
| miR-15abc/16/16abc/195/322/424/497/1907 | + | + | − | − | − |
| miR-338/338-3p | + | + | − | − | − |
| miR-19ab | − | + | − | − | − |
| miR-326/330/330-5p | + | − | − | − | − |
| miR-377 | + | − | − | − | − |
| miR-491-5p | + | − | − | − | − |

MAPs = microtubule-associated proteins;
bolded microRNA families are broadly conserved among vertebrates

TABLE 7

Comparison of miR-219 Read Frequencies in AD, TPD and Control

| Case | Classification | miR-219-5p Reads | % | miR-219-1-3p Reads | % | miR-219-2-3p Reads | % |
|---|---|---|---|---|---|---|---|
| 1 | AD | 183,085 | 1.35% | 1 | 0.00% | 11,165 | 0.08% |
| 2 | AD | 14,303 | 0.23% | 1 | 0.00% | 8,118 | 0.13% |
| 4 | AD | 48,438 | 0.41% | 6 | 0.00% | 26,038 | 0.22% |
| 5 | AD | 50,131 | 0.48% | 1 | 0.00% | 17,342 | 0.16% |
| 6 | AD | 13,928 | 0.31% | 3 | 0.00% | 5,127 | 0.11% |
| 7 | AD | 28,084 | 0.30% | 3 | 0.00% | 14,228 | 0.15% |
| 1 | Control | 121,194 | 2.08% | 1 | 0.00% | 33,834 | 0.58% |
| 2 | Control | 77,222 | 1.00% | 2 | 0.00% | 72,402 | 0.94% |
| 4 | Control | 57,114 | 0.68% | 1 | 0.00% | 39,576 | 0.47% |
| 5 | Control | 119,188 | 1.70% | 5 | 0.00% | 77,779 | 1.10% |
| 6 | Control | 217,944 | 0.56% | 8 | 0.00% | 81,925 | 0.21% |
| 16 | Control | 47,953 | 0.55% | 2 | 0.00% | 49,236 | 0.56% |
| 18 | Control | 11,494 | 0.25% | 2 | 0.00% | 6,489 | 0.14% |
| 7 | TPD | 25,975 | 0.41% | 2 | 0.00% | 18,523 | 0.30% |
| 15 | TPD | 228,931 | 0.55% | 10 | 0.00% | 140,699 | 0.34% |
| 18 | TPD | 21,249 | 0.21% | 3 | 0.00% | 9,631 | 0.10% |

Example 3—Validation of Differential Expression of microRNA-219-5p in Post-Mortem AD, TPD, and Control Brains Materials and Methods TaqMan MicroRNA assays were used to measure miR-219-5p levels (Applied Biosystems/Life Technologies, Carlsbad, Calif.) in AD (n=7), TPD (n=19) and control (n=20), and validate the findings of Example 2.

100 ng of total RNA was reverse-transcribed using specific stem-loop reverse transcription primers (Applied Biosystems) and miR-219-5p levels were measured with TaqMan microRNA assays on a Mastercycler ep realplex (Eppendorf, Hamburg, Germany). The levels of U24/SNORD24 and Z30/SNORD7 were used as endogenous controls for normalization using the comparative CT method.

Results

Using the TaqMan microRNA assays to validate the findings set forth in Example 2, a significant down-regulation of miR-219-5p in both in AD and TPD samples (p<0.05, Student's t-test) was found when compared to non-demented controls (FIG. 3). Together, these results confirm that miR-219-5p expression is decreased in AD and TPD as compared to controls.

Example 4—Regulation of Tau Expression by MicroRNAs

Materials and Methods

The full-length human MAPT 3' UTR was amplified from genomic DNA from a control subject (homozygous MAPT H1) using the following primers

```
F:
                                     (SEQ ID NO: 9)
5'-AATTCTAGGC GATCGCTCGA GAAGCAGGGT

TTGTGATCAG G-3'
and

R:
                                    (SEQ ID NO: 10)
5'-ATTTTATTGC GGCCAGCGGC CGCGGTGCGT

GGGAAAGAAC TTA-3'
``` and cloned between the XhoI and NotI sites of the dual-luciferase reporter psiCHECK-2 vector (Promega, Madison, Wis.) using the In-Fusion HD cloning kit (Clontech/Takara Bio Inc., Mountain View, Calif.). This quantitative system utilizes a primary Renilla luciferase reporter and a secondary firefly luciferase reporter expression cassette for normalization, which controls for transfection efficiency and cell death.

Site-directed mutagenesis of the miR-219-5p recognition element was generated by using QuickChange II XL Site-Directed Mutagenesis Kit (Agilent/Stratagene, Santa Clara, Calif.), using primers generated using QuickChange Primer Design.

```
miR-219 site_F:
                                    (SEQ ID NO: 11)
5'-CACGCTGGCTTGTGATCTTAAATGAGGGTCGATCCC CCAGGGCTGGGCACTC-3';
and miR-219site_R:
                                    (SEQ ID NO: 12)
5'-GAGTGCCCAGCCCTGGGGATCGACCCTCATTTAAG

ATCACAAGCCAG CGTG-3'.
```

All sequences were verified by Sanger sequencing (Genewiz, South Plainfield, N.J.).

SH-SY5Y neuroblastoma cells were plated at a density of $8 \times 10^4$ cells per well (in 24-well plates) 24 hours before transfection. Luciferase reporter constructs containing the MAPT 3' UTR were cotransfected with microRNA mirVana mimics (Ambion) using Lipofectamine 2000 (Invitrogen, Carlsbad, Calif.), following the manufacturer's protocols. The mutated miR-219-5p binding site MAPT 3' UTR vector was included in indicated experiments as a control. Firefly and Renilla luciferase activities were measured 48 hours after transfection using the dual-luciferase reporter assay system (Promega, Madison, Wis.). At least six transfection assays were performed to obtain statistically significant data for each individual condition.

Results

In order to determine whether miR-219-5p can silence tau expression in vitro, the full-length human tau 3' UTR was inserted into a dual-luciferase reporter construct downstream of the Renilla luciferase and transiently cotransfected this construct along with three microRNA mimics that are predicted to target tau (i.e., miR-219-5p, miR-181d, miR-485-5p) and one that is not (miR-217) into a human neuroblastoma cell line (SH-SY5Y).

While miR-219-5p and miR-181d both have a highly-conserved binding site in the tau 3' UTR, miR-485-5p has six that are poorly conserved. It was found that miR-219-5p (p=0.0362), miR-485-5p (p=0.0115) and miR-181d (p=0.0009) are all capable of significantly reducing luciferase activity compared to mock transfection, but miR-217 is not (FIG. 4A).

Figures 4A, 4B:
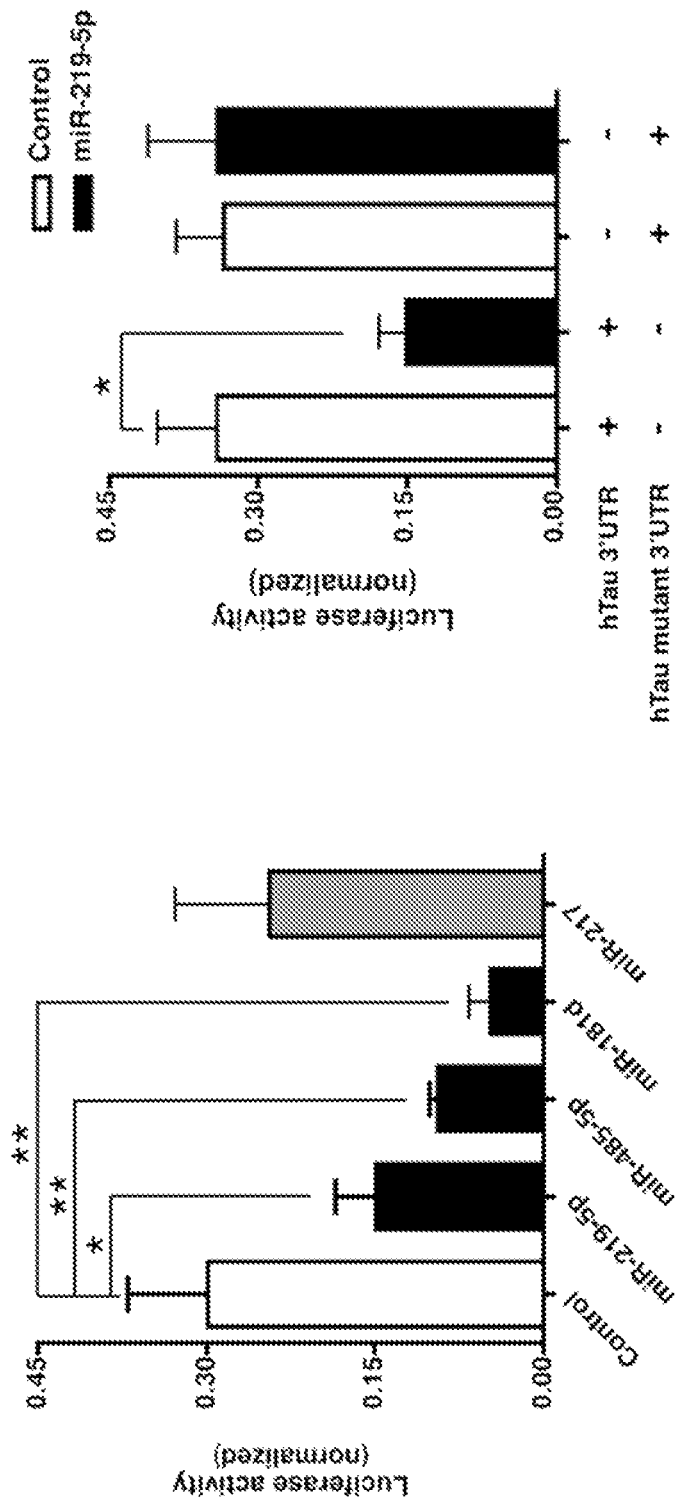
FIG. 4A shows a graph of the luciferase activity of the luciferase reporter construct that contains the entire tau 3' UTR, ones co-transfected with various microRNAs, and an empty vector control.
FIG. 4B is a graph of luciferase activity of constructs with and without site-directed mutagenesis of the miR-219-5p recognition element. * p<0.05, ** p<0.01.

Furthermore, mutation of the miR-219-5p recognition element in the human tau 3' UTR luciferase reporter vector abrogates silencing (FIG. 4B). These findings demonstrate that silencing of tau expression by miR-219-5p is through direct interaction with the predicted and highly conserved recognition element in the tau 3' UTR.

Example 5—miR-219-5p Regulated Tau Expression in Primary Hippocampal Neuronal Cultures Materials and Methods The full-length 3' UTR of human MAPT was also cloned into the lentiviral luciferase transfer vector pLenti-Luc-UTR (Applied Biological Materials, Vancouver, British Columbia, Canada).

Genomic DNA from the same control individual described above was amplified using the following primers:

```
Lenti-MAPT3'UTR-EcoRI_F:
                                    (SEQ ID NO: 13)
5'-TGGTGGCCTGCAGGTGAATTCAAGCAGGGTTTG TGATCAGG-3';
and LentiMAPT3'UTR-BamHI_R:
                                    (SEQ ID NO: 14)
5'-GAGCTGCAGTCTAGAGGATCCGGTGCGTGGG

AAAGAA CTTA-3'
``` and cloned into the EcoRI-BamHI sites of the pLenti-UTR-Luc vector. The human mir-219 precursor sequence and the scrambled microRNA control were made using the lentiviral vector pEZX-MR03 (Genecopoeia, Rockville, Md.). Lentiviral packaging and stock production of lentiviral transfer vectors containing the miR-219 precursor or scrambled control and the lenti-LucMAPT 3'UTR were performed as described by Follenzi and Naldini (2002).

The human HEK 293T cell line that stably and constitutively expresses the SV40 large T antigen and facilitates optimal lentivirus production was used. HEK 293T cells (ATCC) were grown either in Dulbecco's modified Eagle's medium (DMEM) or DMEM/F12 medium (Cellgro) supplemented with 10% fetal bovine serum, 2 mM glutamine, 100 units/ml penicillin, and 100 µg/ml streptomycin in a humidified atmosphere of 5% CO2 and 95% air at 37° C. Lentiviral stock titration was carried out using Global UltraRapid Lentiviral Titer Kit (System Biosciences).

Primary rat hippocampal cultures from both male and female rat pups were generated as described by Brewer et al. (1993). Hippocampal cultures were kept at 37° C. with 5% $CO_2$ in Neurobasal medium (Invitrogen) with B27 supplement and Glutamax (Invitrogen) and plated at a density of $2.5 \times 10^5$ cell/ml on dishes coated with poly-L-lysine (Sigma-Aldrich, St. Louis, Mo.). Cultures were used after approximately 14 to 21 days in vitro.

Primary hippocampal cultures were co-transduced with vectors containing either the miR-219 precursor or scrambled control and the lenti-LucMAPT 3'UTR.

After 72 or 96 hours, luciferase activity was assayed.

Results

Since it was not clear whether observations in neuroblastoma cells would be valid in non-neoplastic neurons, the findings were replicated in rat primary hippocampal neuronal cultures. The interaction between the miR-219-5p recognition element and the human tau 3' UTR is highly conserved, justifying the use of this cellular model.

These cultures were co-transfected with lentiviral constructs containing the entire tau 3' UTR and either miR-219-5p or a scrambled control. After 72 hours, a six fold increase in miR-219-5p expression was observed (FIG. 5D). When miR-219-5p and tau 3' UTR lentiviral constructs were cotransduced into the hippocampal cultures, a significant reduction of 3' UTR activity is observed. There is no difference with the scrambled control microRNA lentivirus (FIG. 6A). Transduction with the lentiviral miR-219-5p, but not the scrambled control, also significantly reduces expression of endogenous tau protein (FIG. 6B). Real-time QPCR expression analysis does not show a significant difference in tau mRNA levels in these cultures transduced with lentiviral miR-219-5p or scrambled control, suggesting that the mechanism of miR-219-5p is to repress protein translation (FIG. 6C).

Example 6—NGF-Induced Tau Expression and Neurite Outgrowth were Reduced by miR-219

Materials and Methods

PC12 cells or primary hippocampal neurons were fixed with 4.0% paraformaldehyde (Thermo Fisher Scientific/Pierce, Rockford, Ill.) and permeabilized with 0.4% Triton X-100 (Sigma-Aldrich) in PBS, blocked with SuperBlock buffer in TBS (Thermo Fisher Scientific, Rockford, Ill.) and incubated overnight in the MAP2 (Cell Signaling, Danvers, Mass.) or TauC antisera (DAKO, Glostrup, Den-mark). Anti-mouse secondary antisera conjugated with Alexa Fluor dyes (Invitrogen) were used.

Labeled PC12 cells or neurons were imaged using either LSM 510 Meta confocal micro-scope, equipped with 40×1.3 NA and a 100×1.4 NA oil-immersion objectives and Zeiss observer Z1 or an AxioObserver Z1 microscope (Carl Zeiss, Oberkochen, Del.). Scanning used two excitation lines of the argon laser (488 nm for Alexa Fluor-488, 568 nm for Alexa Fluor-568). For confocal images, Z-stacks were collected at 1.0 μm intervals and then compressed into a single image for analysis using Volocity Imaging software (Volocity Acquisition and Volocity Visualization, PerkinElmer). For AxioOb-server fluorescence imaging Axiovision Rel 4.8.2 was used.

PC12 cells were cultured as described previously by Greene and Tischler (1976), and Grau and Greene (2012), in collagen-coated dishes with RPMI 1640 medium supplemented with 10% heat-inactivated horse serum and 5% fetal bovine serum. Neuronal differentiation media for PC12 contains NGF (100 ng of human recombinant protein per ml) and RPMI 1640 medium supplemented with 1% heat-inactivated donor horse serum.

Immunoblotting was performed by resolving total protein by SDS-PAGE and transblotted using standard procedures. Nitrocellulose membranes (BioRad, Hercules, Calif.) were incubated with TauC (DAKO, Glostrup, Denmark), β-actin (Sigma-Aldrich, St. Louis, Mo.) and secondary antibodies (Thermo Fisher Scientific, Waltham, Mass.), and revealed by chemiluminescence using the ECL kit (Millipore, Billerica, Mass.) and Biomax Light films (Sigma-Aldrich).

Results

Having demonstrated that microRNAs were capable of regulating tau expression, it was asked whether they can modulate tau in a physiological context. Previous work has shown that tau protein plays a functional role in neurite outgrowth in PC12 cells following exposure to nerve growth factor (NGF) (Drubin et al. (1985); Drubin et al. (1988)).

Application of NGF to PC12 cells induced differentiation into neuron-like cells with neurite outgrowth with concomitant increases in tau mRNA and protein levels (FIGS. 7A and 7B).

Intriguingly, it was found that that NGF also induced a transient reduction in miR-219-5p at three days, however this returned to baseline once the cells had fully differentiated at seven days (FIG. 7C).

To determine whether these changes in miR-219-5p play a direct role in tau-mediated neurite outgrowth, miR-219-5p was overexpressed in PC12 cells that were exposed to NGF. QPCR confirmed overexpression of miR-219-5p (FIG. 7D). Immunoblot and QPCR analysis in NGF-treated PC12 cells demonstrated that lentiviral overexpression of miR-219-5p attenuated tau mRNA and protein expression (FIGS. 7E and 7F). While an approximately 35% decrease in tau mRNA levels following miR-219-5p treatment was observed, an approximately 75% reduction in tau protein levels was also observed.

Immunofluorescence microscopy with antisera recognizing tau in NGF-treated PC12 cells confirmed that NGF treatment results in neurite outgrowth (FIGS. 7G and 7H). Cells that had been transduced with lentiviral miR-219-5p and a GFP reporter showed cells that fail to extend tau-positive processes compared to uninfected cells (FIGS. 7I-K). These results suggested that the effect of NGF on tau-mediated neurite outgrowth is modulated by miR-219-5p by directly influencing tau expression on the post-transcriptional level. Overexpression of miR-219-5p and a GFP reporter as observed by immunofluorescence confocal microscopy using antisera against tau demonstrated abrogation of neurite outgrowth as demonstrated by the merged image. Note that cells that are not transduced with the miR-219-5p construct maintained their ability to elaborate neurites.

Example 7—miRNA Recognition Elements in *Drosophila* Tau 3'UTR

Materials and Methods

TargetScan described in Example 2 was used on the *Drosophila* genome.

Results

Examination of the *Drosophila* genome revealed a tau gene that has a previously incompletely annotated 3'UTR region that extends 1439 base pairs and contains a miR-219 recognition element as shown in Table 8.

TABLE 8

Predicted miRNA Recognition Elements in the *Drosophila* tau 3' UTR

| miRNA family | Site type | 3' UTR start | 3' UTR end |
| --- | --- | --- | --- |
| miR-980 | 1a | 90 | 96 |
| miR-33 | 8mer | 129 | 135 |
| miR-954 | 8mer | 164 | 170 |
| miR-193 | 1a | 182 | 188 |

TABLE 8-continued

Predicted miRNA Recognition Elements in the *Drosophila* tau 3' UTR

| miRNA family | Site type | 3' UTR start | 3' UTR end |
| --- | --- | --- | --- |
| miR-1012 | m8 | 304 | 310 |
| miR-33 | m8 | 317 | 323 |
| miR-977 | 8mer | 356 | 362 |
| miR-967 | 1a | 357 | 363 |
| miR-33 | 1a | 534 | 540 |
| miR-3/309/318 | 1a | 561 | 567 |
| miR-219 | 8mer | 864 | 870 |
| miR-315 | m8 | 867 | 873 |
| miR-966 | 1a | 889 | 895 |
| miR-961 | m8 | 1015 | 1021 |
| miR-281-2-3p | 1a | 1056 | 1062 |
| miR-959 | 1a | 1056 | 1062 |
| miR-8 | m8 | 1136 | 1142 |
| miR-184 | 1a | 1293 | 1299 |
| miR-927 | 1a | 1421 | 1427 |
| miR-277 | 1a | 1496 | 1502 |
| miR-1000 | 1a | 1510 | 1516 |
| miR-210.1 | 1a | 1542 | 1548 |

TargetScan predicts the following site types: 8mer: an exact match to positions 2-8 of the mature miRNA (the seed + position 8) followed by an 'A'. m8: an exact match to positions 2-8 of the mature miRNA (the seed + position 8). 1a: an exact match to positions 2-8 of the mature miRNA (the seed) followed by an 'A' (6).

Example 8—Overexpression of miR-219 in *Drosophila melanogaster* Results in Neural Dysfunction and Decreased Tan Expression Materials and Methods

*Drosophila melanogaster* overexpressing full length miR-219 microRNA were obtained from the Bloomington stock center. These flies overexpress the miR-219 in the pan-neuronal ELAV driver.

The flies were examined visually for phenotypes versus control flies and flies overexpressing microRNA miR-34. They were also subject to a negative geotaxis or climbing assay.

*Drosophila* Immunoblotting

Adult Drosophilae were homogenized in Neuronal Protein Extraction Reagent (N-PER) supplemented with Halt Protease & Phosphatase inhibitor cocktail (Thermo Scientific). Lysates were incubated on ice for 10 minutes and centrifuged at 13,000×g for 15 minutes at 4° C. The protein concentration was determined using the BCA protein assay kit (Thermo Scientific). Samples were resolved by SDS-PAGE and analyzed by Western blot. Nitrocellulose membranes (BioRad, Hercules, Calif.) were incubated with an anti-*Drosophila* tau antibody (a generous gift from Dr. Nick Lowe, UK), β-actin (Sigma-Aldrich, St. Louis, Mo.) and secondary antibodies (Thermo Fisher Scientific), and revealed by chemiluminescence using the ECL kit (Millipore, Billerica, Mass.) and Biomax Light films (Sigma-Aldrich).

Immunoblots were also performed on protein extracts from the whole fly, the head only, and the body only of representative flies from each group using antisera from Dr. Nick Lowe that targets *Drosophila* tau (dTau).

Results

Figure 8A:
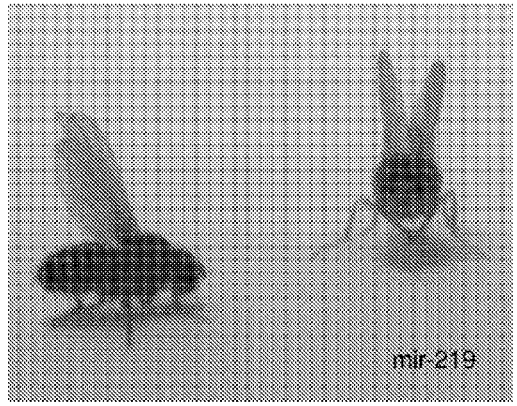
FIG. 8A-D depict the results of in vivo experiments with Drosophila melanogaster.
Figure 8B:
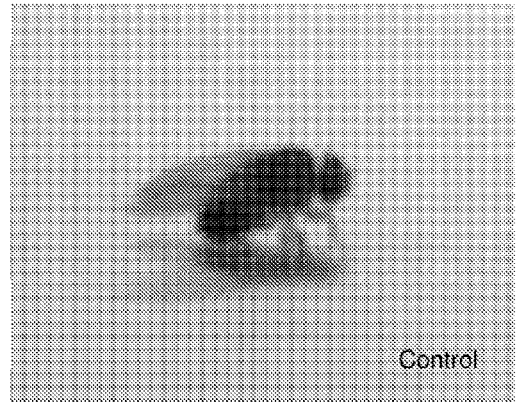
Figure 8C:
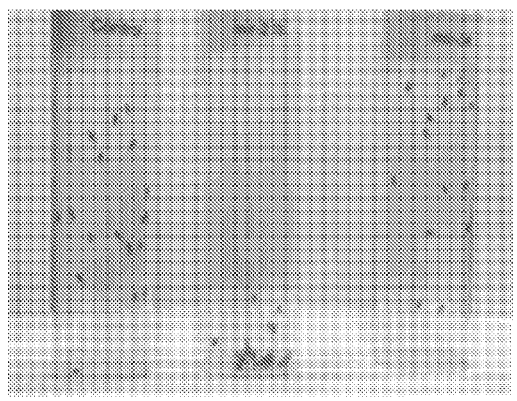

As shown in FIG. 8A, flies that overexpressed miR-219 have a wings up phenotype as compared to controls in FIG. 8B.

Figure 8D:
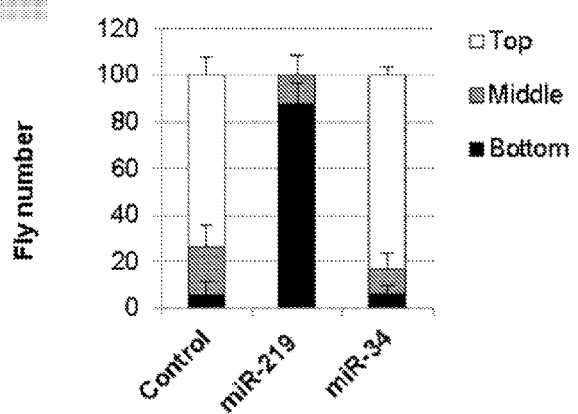

When subjected to a negative geotaxis or climbing assay, the flies overexpressing the miR-219 (middle cylinder) were unable to climb as high as the controls (left cylinder) and flies overexpressing miR-34, which does not contain a conserved recognition element in the fly tau 3'UTR (right cylinder). See also FIG. 8D.

This assay together with the wings up phenotype showed a weakness in the flight muscles.

Figure 8E:
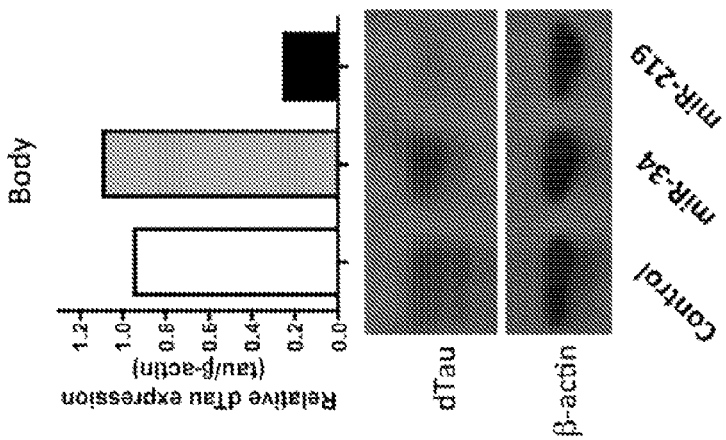
FIG. 8E-G are representative immunoblots, both images and graphs quantifying the results, using antisera targeting Drosophila tau in the whole fly (FIG. 8E), the head (FIG. 8F), and the body (FIG. 8G) of control flies, flies overexpressing miR-219, and flies overexpressing miR-34.
Figure 8F:
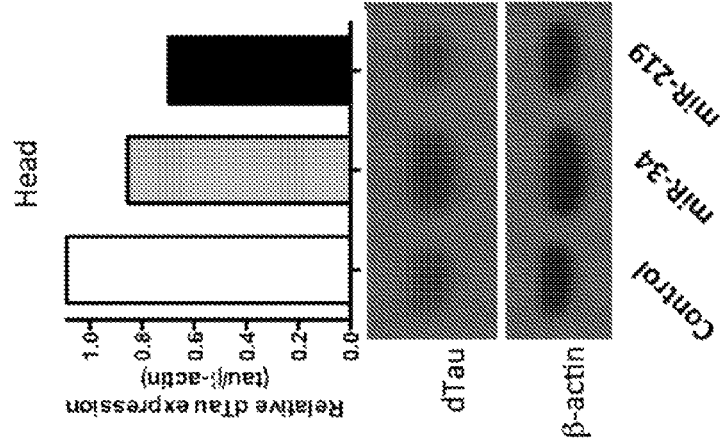
Figure 8G:
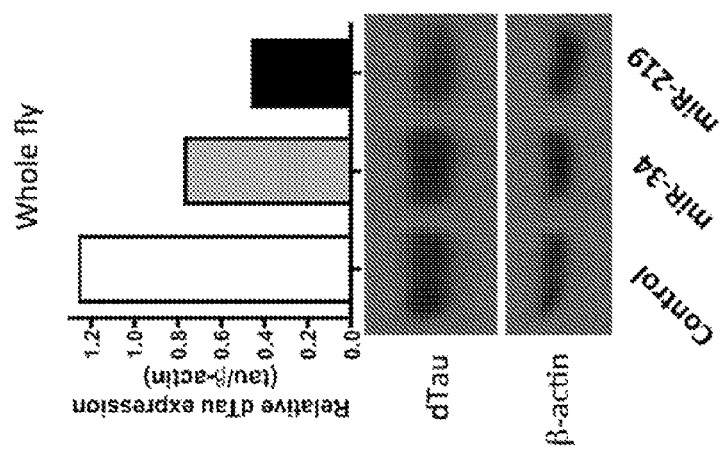

Flies overexpressing miR-219 also had decreased tau expression as compared to controls and flies overexpressing miR-34 (FIGS. 8E-G).

Example 9—Further Evidence that Overexpression of mir-219 in *Drosophila* Melanogaster Results in Decreased Tan Expression Materials and Methods

*Drosophila* Strains

*Drosophila* miR-219 or scrambled control lines (a generous gift from Eric C. Lai) were derived from a UAS-DsRed-miRNA plasmid collection (Bejarano et al. (2012); Silver et al. (2007)). The miRNA inserts included approximately 200-250 nucleotides flanking each side of the pre-miRNA hairpin and were amplified from w1118 or Canton S genomic DNA.

To generate *Drosophila* miRNA sponge (miR-219 sponge) or scrambled controls, ten repetitive sequences complementary to a miRNA with mismatches at positions 9-12 for enhanced stability were introduced into the 3' UTR of EGFP or mCherry in a pUAST expression vector (Loya et al. (2009); Ebert and Sharp (2010)).

Transgenic luciferase reporter *Drosophila* lines were generated that express the luciferase coding region fused with either a control GAPDH 3'UTR (200 bp; lacks the miR-219 binding site), or the human tau 3' UTR (4162 bp), using a series of *Drosophila* phiC31 compatible GAL4-UAS vectors termed pBID (attB, Insulated, *Drosophila*) (Wang et al. (2012)). The pan-neuronal elav-GAL4 driver was used to drive transgene expression. All *Drosophila* crosses were maintained at 25° C.

miRNA-219 was overexpressed in the neurons of the *Drosophila* per Bejarano et al. (2012)).

Immunoblots were performed as described in Example 7.

*Drosophila* Luciferase Reporter Assay

*Drosophila* luciferase reporter lines were crossed with either the miR-219 or the miR-219 sponge lines. The pan-neuronal elav-GAL4 driver was used to drive transgene expression. Luciferase activity was measured from the lysate of pooled adult *Drosophila* heads using the Luciferase Reporter Assay System (Promega, Madison, Wis.). A control line with a GAPDH 3' UTR was used for normalization.

*Drosophila* Quantitative PCR

Total RNA was isolated from the whole *Drosophila*. Briefly, flies were lysed in QIAzol and homogenized using a QIAshredder column. Total RNA was extracted using the miRNeasy Kit (Qiagen, Valencia, Calif.). RNA concentrations were measured with a Nanodrop ND-1000 Spectrophotometer. Equal amounts of RNA were reverse transcribed using the First Strand cDNA Synthesis Kit (Origene, Rockville, Md.) according to the manufacturer's instructions. QPCR for *Drosophila* tau and the endogenous control RpL32 was performed using TaqMan Gene Expression assays (Applied Biosystems, Foster, Calif.). Real-time PCR reactions were performed in triplicate with MicroAmp optical 96-well plates using a Mastercycler ep realplex (Eppendorf, Hauppauge, N.Y.) with the following conditions; an initial step of 10 minutes at 95° C., followed by 40 cycles of 15 seconds at 95° C., 1 minute at 60° C. TaqMan MicroRNA assays were used to measure miR-219-5p levels (Applied Biosystems). Total RNA was reverse-transcribed using specific stem-loop reverse transcription primers (TaqMan MicroRNA assays, Applied Biosystems) and miR-219-5p levels were measured with TaqMan MicroRNA assays on a Mastercycler ep realplex (Eppendorf). The levels of 2srRNA were used as endogenous control for normalization using the comparative CT method. Each data point is the result of at least three biological replicates each composed of three technical replicates.

Results

Figure 9B:
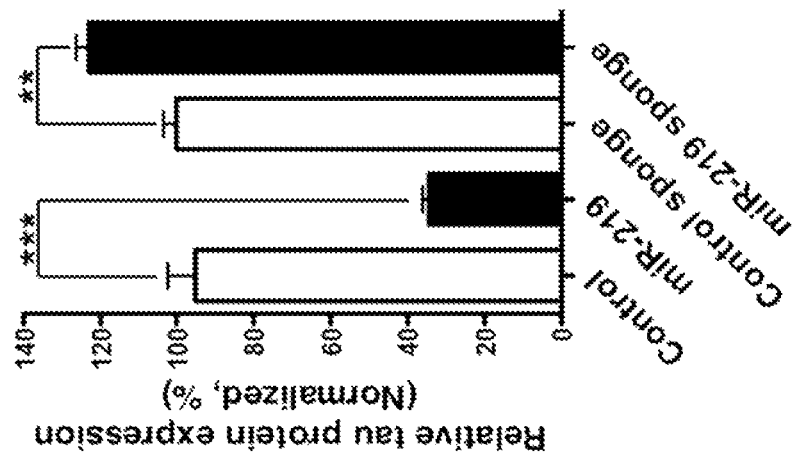
FIG. 9B is a graph quantifying these immunoblots results.
Figure 9A:
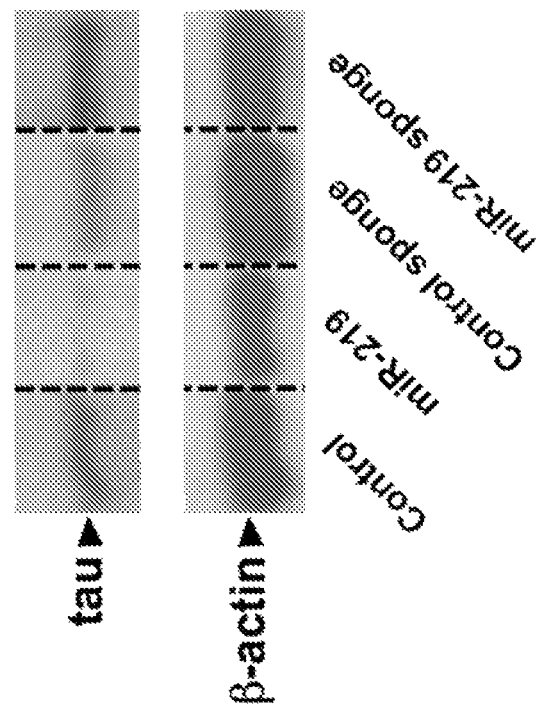
FIG. 9A is an image of an immunoblot of extracts from Drosophila overexpressing miR-219 using the elav-GAL4 neural driver, Drosophila scrambled miRNA control, Drosophila overexpressing the miRNA sponge inhibitor, a transgene containing multiple miR-219 recognition elements, and Drosophila scrambled control sponge.
Figures 9C, 9D:
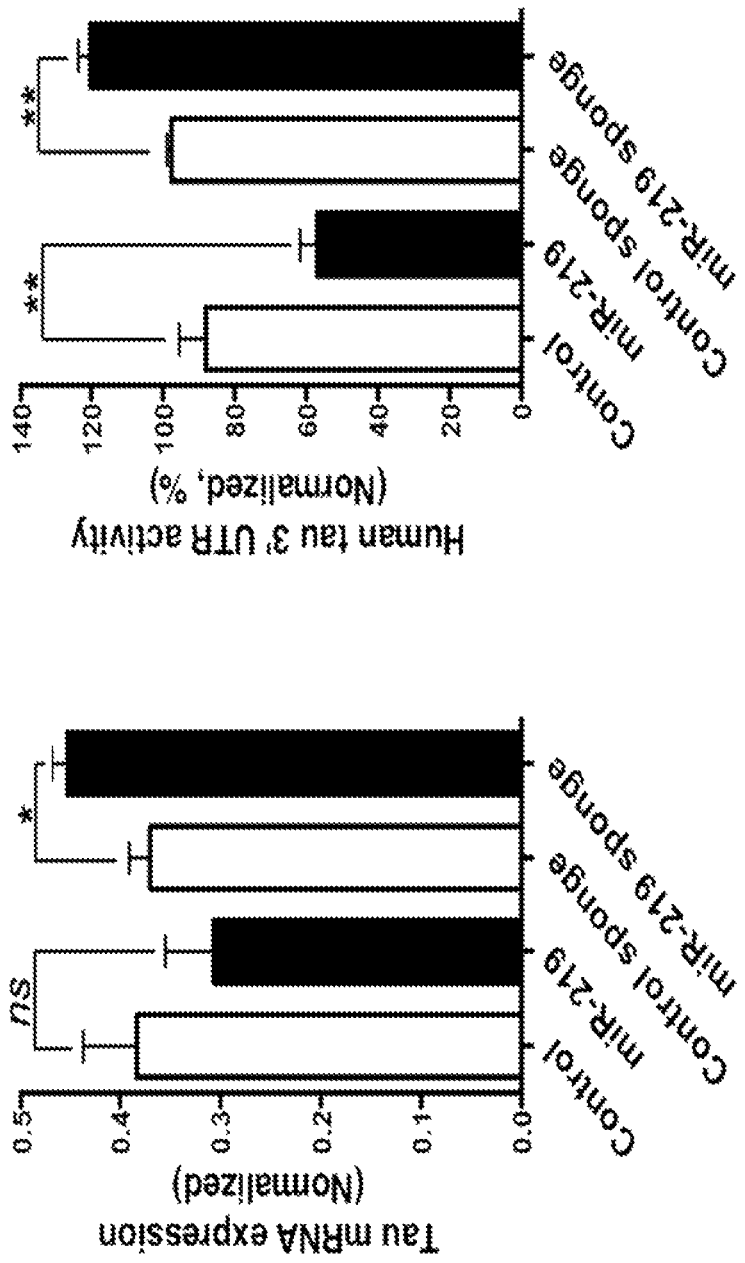
FIG. 9C is a graph of the results of total RNA from flies overexpressing miR-219 or the miR-219 sponge using elav-GAL4 as compared to controls.
FIG. 9D is a graph of the results of luciferase reporter assay of lysates from flies that co-express firefly luciferase fused to the human tau 3' UTR with miR-219, scrambled control, the miR-219 sponge inhibitor, and scrambled control sponge. A control line with a human GAPDH 3' UTR fused to luciferase was used for normalization.
Figure 9E:
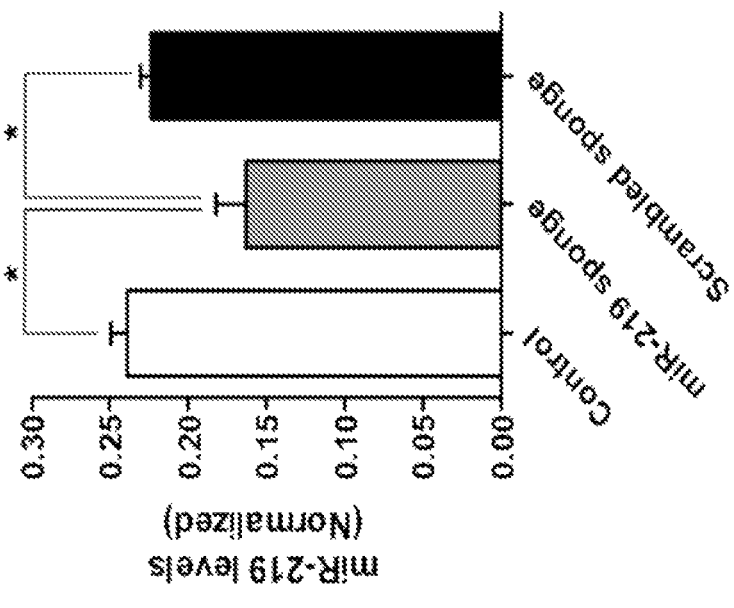
FIG. 9E is a graph showing the quantification of miR-219 levels in flies overexpressing miR-219, controls and scrambled. 2sRNA levels were used for normalization.
Figure 9F:
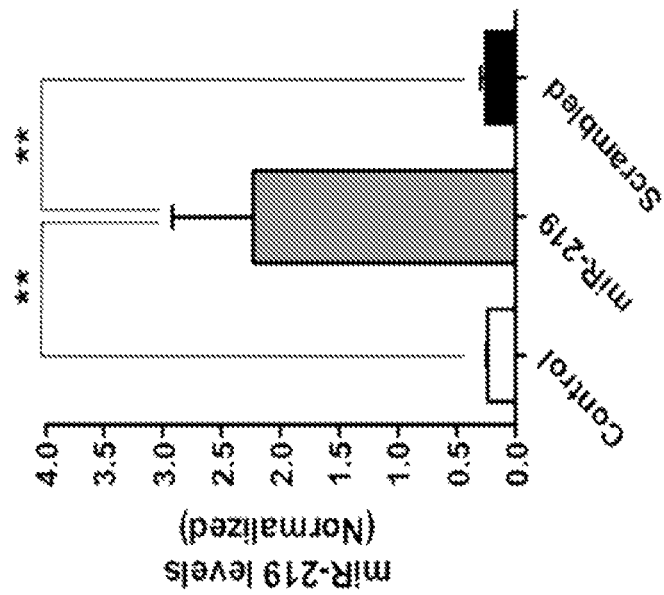
FIG. 9F is a graph showing the quantification of in flies expressing the miR-219 sponge, controls and scrambled sponge. Data are means±SEM and are representative of ≥3 experiments. Statistical analysis was performed using Student's t-test (two-tailed distribution, *P≤0.05, **P≤0.01).

When miR-219 was overexpressed in the fly brain, a highly significant reduction in tau protein level was found (63.8%; P<0.001) as compared to the scrambled miRNA control as shown by immunoblots (FIGS. 9A, B, and E).

miR-219 levels were depleted using a sponge inhibitor, a recombinant transcript containing multiple tandem miR-219 binding sites that significantly reduces the levels of miR-219 when expressed in Drosophila neurons (FIG. 9F). Expression of the miR-219 sponge resulted in a significant increase in the levels of endogenous tau protein (23.1%; P<0.05) compared to controls as shown by immunoblots (FIGS. 9A and B). Overexpression of the miR-219 sponge resulted in a significant increase (22%; P<0.05) in the Drosophila tau mRNA as measured by quantitative PCR (FIG. 9C). However, the Drosophila tau mRNA levels were unchanged following overexpression of miR-219, suggesting effects on both mRNA levels and translation.

The analysis was extended and confirmed that miR-219 was also capable of regulating human tau 3' UTR activity in vivo. Transgenic Drosophila were generated that express a luciferase reporter fused to the human tau 3' UTR. It was found that the overexpression of miR-219 significantly reduced the luciferase activity of the human tau 3' UTR constructs compared to the scrambled control. In contrast, the miR-219 sponge inhibitor significantly increases luciferase activity, confirming an evolutionarily conserved bidirectional mechanism of tau regulation (FIG. 9D).

Example 10—Human Tau Toxicity in the Drosophila Eye is Abrogated by miR-219

Materials and Methods

Studies have shown that overexpression of tau results in a marked rough eye phenotype in Drosophila (Jackson et al. (2002); Wittman et al. (2001); Williams et al. (2000)). To determine whether miR-219 influences tau toxicity, miR-219 and htau (without the 3' UTR) was co-expressed in the Drosophila eye. A transgenic Drosophila that expressed the htau protein coding region alone, without its 3' UTR, was generated using a series of pBID vectors described in Example 9. Crosses were made with transgenic miR-219 flies (Bloomington stocks), the miR-219 sponge inhibitor (as described in Example 9) or the scrambled miR (generous gift of Dr. Van Vactor). The GMR-GAL4 driver was used to specifically express the transgenes in the eye. Eye phenotypes were recorded 2 days post eclosion (n=3).

Results

Control flies expressing the GMR driver alone showed a normal eye phenotype (FIG. 10A). Overexpression of htau alone resulted in a rough eye phenotype (reduction in eye size and an irregular morphology) compared to controls, as predicted (FIG. 10B). Co-overexpression of htau and miR-219 resulted in a partial reversal of the rough eye phenotype, consistent with a protective role (FIG. 10C). In contrast, co-overexpression of htau and the miR-219 sponge resulted in a worsening of the phenotype, demonstrating bi-directionality (FIG. 10D). Co-overexpression of htau and the scrambled miRNA control did not rescue the rough eye phenotype (FIG. 10E).

These results demonstrated that miR-219 influences tau toxicity. This finding has prompted a hypothesis that miRNAs regulate tau toxicity either directly (perhaps by reducing endogenous fly tau), indirectly through GSK3β (because this htau transgene lacks a functional miR-219 site) or both.

Example 11—The Human Tau 3' UTR Contains Cis-Acting Elements that Ameliorate Tau Toxicity in the Drosophila Eye Materials and Methods Flies that overexpress htau coding sequence fused with the htau 3' UTR were generated by modifying pBID vector backbone described in Example 10 by inserting the htau protein coding region sequence upstream of the Gateway cassette without a synthetic SV40 polyadenylation site. The human GAPDH and tau 3' UTRs were then inserted. Flies were generated commercially. Expression in the eye was obtained with the GMR driver described in Example 10.

Results

Figures 11A, 11B, 11C:
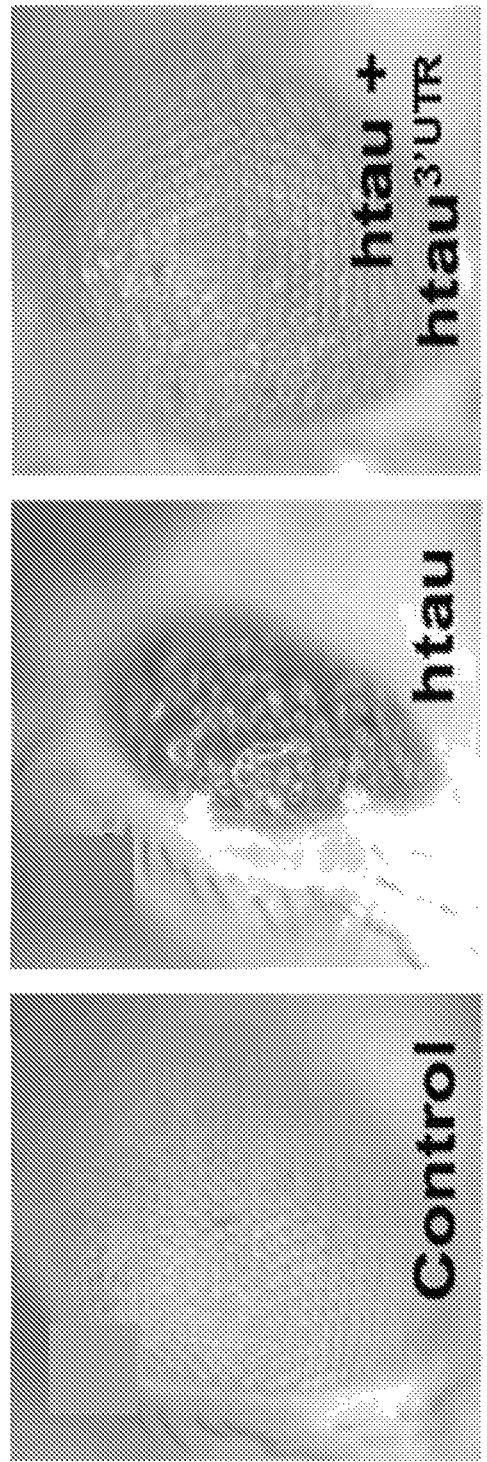
FIG. 11A-C are images of the eyes of Drosophila.

Control flies expressing the GMR driver alone showed a normal eye phenotype (FIG. 11A). Overexpression of htau fused to GADPH 3'UTR resulted in a rough eye phenotype (reduction in eye size and an irregular morphology) compared to controls, as predicted (FIG. 11B). In contrast, overexpression of tau fused to the tau 3' UTR diminishes the severity of the rough eye, indicating the presence of protective cis-acting regulatory elements in the tau 3' UTR (FIG. 11C).

Example 12—MiR-219 is Predicted to have Other Targets than Tau

Materials and Methods

Functional trend analysis was performed using FuncAssociate 2.0 (Berriz et al. (2009)) of predicted targets of miR-219 using TargetScan as described in Example 2.

Results

As shown in Table 9, miR-219 was predicted to play a role in neuron differentiation, axon development, and gene expression.

TABLE 9

Functional Trend Analysis of Predicted miR219 Targets Overrepresented Attributes

| Gene Ontology ID | Name | p (adjusted) |
| --- | --- | --- |
| GO:0010628 | Positive regulation of gene expression | <0.001 |
| GO:0022008 | Neurogenesis | <0.001 |
| GO:0030182 | Neuron differentiation | <0.001 |
| GO:0031175 | Neuron projection development | <0.001 |
| GO:0048666 | Neuron development | <0.001 |
| GO:0061564 | Axon development | 0.042 |
| GO:0007399 | Nervous system development | 0.004 |

Example 13—Evidence of Additional miRNAs Differentially Expressed in AD and TPD Patients Materials and Methods Patient samples as described in Example 1 from five controls, five patients with tangle-only dementia and three with Alzheimer's Disease were used. RNA was isolated by Trizol or Qiagen as described in Example 1. Approximately 0.5 μg of total RNA was loaded on a SmartChip (Wafergen Biosystems) with approximately 250,000 cells total, and approximately 5 cells per reaction. Samples were loaded onto a SmartChip miRNA Panel, v3.0 with 1,036 miRNA assays, each with four technical replicates. Additionally, seven endogenous on-chip control assays and four endogenous yeast cDNA fragment process controls were used. See Table 10.

Statistics utilized a Mann-Whitney test in qbase$^{plus}$ from biogazelle.

TABLE 10

Sample Information and Chip Stats

| SAMPLE | RNA KIT | RNA (ng/μl) | RNA RIN | PLATFORM miRNA CHIP FILL (ML) | CHIP MEAN COUNT (CYCLES) | CHIP MEAN TEMP (C. °) | CHIP # INFOR- MATIVE ASSAYS |
|---|---|---|---|---|---|---|---|
| NTC | | | | 0.55 | 22.4 | 68.6 | 20 |
| Ctrl1142 | Qiagen | 1050 | 7.1 | N/A | 23.0 | 77.5 | 822 |
| Ctrl1134 | Qiagen | 1262 | 6.9 | N/A | 22.9 | 77.7 | 765 |
| Ctrl1159 | Qiagen | 750 | 6.8 | 0.61 | 23.6 | 77.3 | 849 |
| Ctrl1161 | Qiagen | 739 | 5.3 | 0.55 | 23.5 | 77.5 | 837 |
| Ctrl1187 | Qiagen | 768 | 5.1 | 0.60 | 23.6 | 77.4 | 827 |
| TOD1178 | Qiagen | 1060 | 7.4 | 0.63 | 23.5 | 77.4 | 832 |
| TOD1099 | Qiagen | 666 | 6.7 | 0.60 | 23.6 | 77.6 | 781 |
| TOD4119 | Qiagen | 1195 | 5.9 | 0.56 | 23.4 | 77.3 | 817 |
| TOD4193 | Trizol | 1756 | 4.6 | N/A | 22.5 | 77.0 | 779 |
| TOD4153 | Trizol | 1673 | 4.2 | N/A | 23.1 | 77.3 | 851 |
| AD4152 | Qiagen | 596 | 5.0 | 0.57 | 24.2 | 77.2 | 851 |
| AD352 | Qiagen | 596 | 5.0 | 0.57 | 24.5 | 77.0 | 892 |
| AD1059 | Qiagen | 1488 | 7.3 | 0.58 | 23.5 | 77.4 | 815 |
| MEAN | | | | 0.58 | 23.5 | 77.4 | 824.5 |
| STDEV | | | | 0.04 | 0.5* | 0.2* | 34.7* |
| % CV | | | | 6.1 | 2.2* | 0.3* | 4.2* |

*NTC ommitted
RIN—RNA integrity number

Results

Seventy-eight (78) miRNAs displayed a significant difference between the Alzheimer's disease (AD) group and control groups (p≤0.05). Of those 78, thirty-three (33) were down-regulated and are listed in Table 11 and forty-five (45) were up-regulated and are listed in Table 12.

TABLE 11 miRNAs that are Down-regulated in Alzheimer's disease versus Control Group (p ≤ 0.05)

| miRNA | log2 (fold change) |
|---|---|
| HSA-MIR-503 | −0.1 |
| HSA-MIR-30C-2* | −0.1 |
| HSA-MIR-641 | −0.6 |
| HSA-MIR-323-3P | −0.6 |
| HSA-MIR-361-3P | −0.8 |
| HSA-MIR-130B | −0.9 |
| HSA-MIR-548C-5P | −0.9 |
| HSA-MIR-24-1* | −0.9 |
| HSA-MIR-374B* | −0.9 |
| HSA-MIR-922 | −0.9 |
| HSA-MIR-17 | −0.9 |
| HSA-MIR-296-5P | −1.0 |
| HSA-MIR-3660 | −1.0 |
| HSA-MIR-3186-5P | −1.1 |
| HSA-MIR-23B* | −1.1 |
| HSA-MIR-3130-5P | −1.1 |
| HSA-MIR-297 | −1.1 |
| HSA-MIR-20A* | −1.1 |
| HSA-MIR-644 | −1.2 |
| HSA-MIR-32 | −1.3 |
| HSA-MIR-18A | −1.3 |

TABLE 11-continued miRNAs that are Down-regulated in Alzheimer's disease versus Control Group (p ≤ 0.05)

| miRNA | log2 (fold change) |
|---|---|
| HSA-MIR-21 | −1.3 |
| HSA-MIR-148A* | −1.4 |
| HSA-MIR-576-5P | −1.4 |
| HSA-MIR-1250 | −1.4 |
| HSA-MIR-545 | −1.4 |
| HSA-MIR-151-5P | −1.4 |
| HSA-MIR-34C-5P | −1.4 |
| HSA-MIR-590-3P | −1.5 |
| HSA-MIR-34C-3P | −1.6 |
| HSA-MIR-338-3P | −1.7 |
| HSA-MIR-1277 | −1.8 |
| HSA-MIR-219-2-3P | −1.9 |

TABLE 12 miRNAs that are Up-regulated in Alzheimer's disease versus Control Group (p ≤ 0.05)*

| miRNA | log2 (fold change) |
|---|---|
| HSA-MIR-618 | 1.0 |
| HSA-MIR-519A | 1.0 |
| HSA-MIR-3185 | 0.9 |
| HSA-MIR-7 | 0.9 |
| HSA-MIR-518E* | 0.6 |
| HSA-MIR-1225-3P | 0.6 |
| HSA-MIR-124 | 0.6 |
| HSA-MIR-379 | 0.6 |
| HSA-MIR-1247 | 0.6 |
| HSA-MIR-516A-5P | 0.5 |
| HSA-MIR-411 | 0.5 |
| HSA-MIR-542-5P | 0.5 |

TABLE 12-continued miRNAs that are Up-regulated in Alzheimer's disease versus Control Group (p ≤ 0.05)*

| miRNA | log2 (fold change) |
| --- | --- |
| HSA-MIR-302A | 0.5 |
| HSA-MIR-139-5P | 0.4 |
| HSA-MIR-203 | 0.4 |
| HSA-MIR-378 | 0.4 |
| HSA-MIR-107 | 0.4 |
| HSA-MIR-539 | 0.4 |
| HSA-MIR-491-5P | 0.4 |
| HSA-MIR-3194 | 0.4 |
| HSA-MIR-222 | 0.4 |
| HSA-MIR-126* | 0.4 |
| HSA-MIR-138 | 0.4 |
| HSA-MIR-1283 | 0.3 |
| HSA-MIR-127-3P | 0.3 |
| HSA-MIR-939 | 0.3 |
| HSA-MIR-377* | 0.3 |
| HSA-MIR-29A* | 0.3 |
| HSA-MIR-339-3P | 0.3 |
| HSA-MIR-519C-3P | 0.3 |
| HSA-MIR-582-3P | 0.2 |
| HSA-MIR-134 | 0.2 |
| HSA-MIR-708 | 0.2 |
| HSA-MIR-126 | 0.2 |
| HSA-MIR-432 | 0.2 |
| HSA-MIR-744* | 0.2 |
| HSA-MIR-582-5P | 0.2 |
| HSA-MIR-324-3P | 0.2 |
| HSA-MIR-497 | 0.2 |
| HSA-MIR-31 | 0.2 |
| HSA-MIR-99A* | 0.1 |
| HSA-MIR-486-5P | 0.1 |
| HSA-MIR-218 | 0.1 |
| HSA-MIR-1197 | 0.0* |
| HSA-MIR-99B | 0.0* |

One hundred and fifty two (152) miRNAs displayed a significant difference between the tangle-only (TOD) group and the control group. Thirty-six (36) miRNAs displayed a significant difference between TOD and control groups (p≤0.01), forty-eight (48) miRNAs displayed a significant difference between TOD and control groups (0.01≤p<0.02) and sixty-eight (68) miRNAs displayed a significant difference between TOD and control groups (0.02≤p<0.05).

Of the 152, seventy-six (76) were down-regulated and are listed in Table 13, and seventy-six (76) were up-regulated and are listed in Table 14.

TABLE 13 miRNAs that are Down-regulated in TOD versus Control Group (p ≤ 0.05)

| miRNA | log2 (fold change) |
| --- | --- |
| HSA-MIR-1256 | -0.1 |
| HSA-MIR-4298 | -0.3 |
| HSA-MIR-141 | -0.3 |
| HSA-MIR-3692 | -0.4 |
| HSA-MIR-937 | -0.5 |
| HSA-MIR-200C* | -0.5 |
| HSA-MIR-4251 | -0.5 |
| HSA-MIR-3126-3P | -0.5 |
| HSA-MIR-3142 | -0.6 |
| HSA-MIR-593* | -0.6 |
| HSA-MIR-505 | -0.6 |
| HSA-MIR-186 | -0.6 |
| HSA-MIR-3922 | -0.6 |
| HSA-MIR-361-3P | -0.6 |
| HSA-MIR-500B | -0.6 |
| HSA-MIR-3195 | -0.6 |
| HSA-MIR-4311 | -0.7 |
| HSA-MIR-3184 | -0.7 |
| HSA-LET-7I* | -0.7 |
| HSA-MIR-24 | -0.7 |
| HSA-MIR-1205 | -0.7 |
| HSA-MIR-27B | -0.7 |
| HSA-MIR-151-5P | -0.8 |
| HSA-MIR-130B | -0.8 |
| HSA-MIR-1247 | -0.8 |
| HSA-MIR-1260 | -0.8 |
| HSA-MIR-3653 | -0.8 |
| HSA-MIR-182* | -0.8 |
| HSA-MIR-17 | -0.8 |
| HSA-MIR-4258 | -0.8 |
| HSA-MIR-93 | -0.8 |
| HSA-MIR-92A | -0.9 |
| HSA-LET-7A* | -0.9 |
| HSA-MIR-3907 | -0.9 |
| HSA-MIR-576-5P | -0.9 |
| HSA-MIR-20B | -0.9 |
| HSA-MIR-4276 | -0.9 |
| HSA-MIR-106A | -1.0 |
| HSA-MIR-29B | -1.0 |
| HSA-MIR-151-3P | -1.0 |
| HSA-MIR-20A | -1.0 |
| HSA-MIR-600 | -1.0 |
| HSA-MIR-140-5P | -1.0 |
| HSA-MIR-4278 | -1.0 |
| HSA-MIR-939 | -1.0 |
| HSA-MIR-556-3P | -1.0 |
| HSA-MIR-3174 | -1.0 |
| HSA-MIR-590-3P | -1.1 |
| HSA-MIR-181C | -1.1 |
| HSA-MIR-875-3P | -1.1 |
| HSA-MIR-106B | -1.2 |
| HSA-MIR-34C-5P | -1.2 |
| HSA-MIR-4254 | -1.2 |
| HSA-MIR-381 | -1.2 |
| HSA-MIR-181A | -1.3 |
| HSA-MIR-584 | -1.4 |
| HSA-MIR-4286 | -1.4 |
| HSA-MIR-24-1* | -1.4 |
| HSA-MIR-219-2-3P | -1.4 |
| HSA-MIR-100* | -1.5 |
| HSA-MIR-590-5P | -1.5 |
| HSA-MIR-141* | -1.5 |
| HSA-MIR-18A | -1.5 |
| HSA-MIR-19B | -1.6 |
| HSA-MIR-548A-3P | -1.6 |
| HSA-MIR-545 | -1.7 |
| HSA-MIR-200A | -1.8 |
| HSA-MIR-3691 | -1.9 |
| HSA-MIR-3690 | -2.0 |
| HSA-MIR-338-3P | -2.0 |
| HSA-MIR-32 | -2.0 |
| HSA-MIR-19A | -2.0 |
| HSA-MIR-34B* | -2.1 |
| HSA-MIR-33B | -2.2 |
| HSA-MIR-636 | -2.2 |
| HSA-MIR-219-5P | -3.0 |

TABLE 14 miRNAs that are Up-regulated in TOD versus Control Group (p ≤ 0.05)

| miRNA | log2 (fold change) |
| --- | --- |
| HSA-MIR-3622B-3P | 4.2 |
| HSA-MIR-3714 | 3.2 |
| HSA-MIR-4269 | 3.0 |
| HSA-MIR-3677 | 2.8 |
| HSA-MIR-1281 | 2.7 |
| HSA-MIR-4304 | 2.6 |

TABLE 14-continued miRNAs that are Up-regulated in TOD versus Control Group (p ≤ 0.05)

| miRNA | log2 (fold change) |
|---|---|
| HSA-MIR-3150B | 2.4 |
| HSA-MIR-3670 | 2.2 |
| HSA-MIR-524-3P | 2.0 |
| HSA-MIR-517A | 1.9 |
| HSA-MIR-575 | 1.9 |
| HSA-MIR-1224-3P | 1.7 |
| HSA-MIR-489 | 1.6 |
| HSA-MIR-493 | 1.6 |
| HSA-MIR-3652 | 1.6 |
| HSA-MIR-130A* | 1.5 |
| HSA-MIR-483-3P | 1.5 |
| HSA-MIR-1184 | 1.4 |
| HSA-MIR-4290 | 1.4 |
| HSA-MIR-766 | 1.4 |
| HSA-MIR-3665 | 1.2 |
| HSA-MIR-3622A-5P | 1.2 |
| HSA-MIR-572 | 1.2 |
| HSA-MIR-3918 | 1.2 |
| HSA-MIR-4292 | 1.1 |
| HSA-MIR-3678-5P | 1.1 |
| HSA-MIR-3651 | 1.1 |
| HSA-MIR-532-3P | 1.0 |
| HSA-MIR-3679-3P | 1.0 |
| HSA-MIR-1237 | 1.0 |
| HSA-MIR-1258 | 0.9 |
| HSA-MIR-518E | 0.9 |
| HSA-MIR-1182 | 0.9 |
| HSA-MIR-3194 | 0.9 |
| HSA-MIR-378* | 0.8 |
| HSA-MIR-513A-5P | 0.8 |
| HSA-MIR-718 | 0.8 |
| HSA-MIR-4257 | 0.8 |
| HSA-MIR-876-3P | 0.8 |
| HSA-MIR-15A* | 0.8 |
| HSA-MIR-1200 | 0.8 |
| HSA-MIR-558 | 0.8 |
| HSA-MIR-574-5P | 0.8 |
| HSA-MIR-503 | 0.8 |
| HSA-MIR-671-5P | 0.7 |
| HSA-MIR-187 | 0.7 |
| HSA-MIR-518C | 0.7 |
| HSA-MIR-877* | 0.7 |
| HSA-MIR-155* | 0.7 |
| HSA-MIR-302B | 0.7 |
| HSA-MIR-95 | 0.7 |
| HSA-MIR-767-3P | 0.7 |
| HSA-MIR-302D* | 0.7 |
| HSA-MIR-628-5P | 0.6 |
| HSA-MIR-134 | 0.6 |
| HSA-MIR-892A | 0.5 |
| HSA-MIR-614 | 0.5 |
| HSA-MIR-455-3P | 0.5 |
| HSA-MIR-149 | 0.5 |
| HSA-MIR-30C-2* | 0.5 |
| HSA-MIR-133A | 0.4 |
| HSA-MIR-562 | 0.4 |
| HSA-MIR-139-5P | 0.4 |
| HSA-MIR-369-5P | 0.4 |
| HSA-MIR-335* | 0.4 |
| HSA-MIR-31 | 0.4 |
| HSA-MIR-654-3P | 0.4 |
| HSA-MIR-409-5P | 0.4 |
| HSA-MIR-744* | 0.4 |
| HSA-MIR-628-3P | 0.3 |
| HSA-MIR-218-2* | 0.3 |
| HSA-MIR-514 | 0.3 |
| HSA-MIR-380* | 0.2 |
| HSA-MIR-802 | 0.1 |
| HSA-MIR-3915 | 0.1 |
| HSA-MIR-499-5P | 0.1 |

Fifty-four (54) miRNAs displayed a significant difference between TOD and AD groups (p≤0.05). Twenty (2) were down-regulated from TOD as compared to AD and are listed in Table 15, and thirty-four (34) were up-regulated from TOD as compared to AD and are listed in Table 16.

TABLE 15 miRNAs that Down-regulated between TOD and AD Groups (p ≤ 0.05)

| miRNA | log2 (fold change) |
|---|---|
| HSA-MIR-19B-2* | −0.6 |
| HSA-MIR-33B* | −0.7 |
| HSA-MIR-302D* | −0.9 |
| HSA-MIR-521 | −1.0 |
| HSA-MIR-877* | −1.1 |
| HSA-MIR-4292 | −1.2 |
| HSA-MIR-517A | −1.3 |
| HSA-MIR-3665 | −1.3 |
| HSA-MIR-1237 | −1.3 |
| HSA-MIR-585 | −1.4 |
| HSA-MIR-1915* | −1.4 |
| HSA-MIR-3651 | −1.4 |
| HSA-MIR-1295 | −1.4 |
| HSA-MIR-3681* | −1.5 |
| HSA-MIR-3918 | −1.6 |
| HSA-MIR-4304 | −1.7 |
| HSA-MIR-1224-3P | −1.9 |
| HSA-MIR-3150B | −1.9 |
| HSA-MIR-483-3P | −2.0 |
| HSA-MIR-1281 | −3.0 |

TABLE 16 miRNAs that Up-regulated between TOD and AD Groups (p ≤ 0.05*)

| miRNA | log2 (fold change) |
|---|---|
| HSA-MIR-4278 | 1.3 |
| HSA-MIR-3174 | 1.1 |
| HSA-MIR-1205 | 1.1 |
| HSA-MIR-4251 | 1.1 |
| HSA-MIR-29B | 0.9 |
| HSA-MIR-4301 | 0.8 |
| HSA-MIR-3943 | 0.8 |
| HSA-MIR-132* | 0.8 |
| HSA-MIR-140-5P | 0.8 |
| HSA-MIR-377 | 0.8 |
| HSA-MIR-618 | 0.8 |
| HSA-MIR-29A* | 0.7 |
| HSA-MIR-3653 | 0.7 |
| HSA-MIR-210 | 0.6 |
| HSA-LET-7I | 0.6 |
| HSA-MIR-381 | 0.5 |
| HSA-MIR-24-1* | 0.5 |
| HSA-MIR-3907 | 0.5 |
| HSA-MIR-126* | 0.5 |
| HSA-MIR-3647-3P | 0.5 |
| HSA-MIR-379 | 0.4 |
| HSA-MIR-3692 | 0.4 |
| HSA-MIR-34A | 0.4 |
| HSA-MIR-876-5P | 0.4 |
| HSA-MIR-324-3P | 0.3 |
| HSA-MIR-99A* | 0.3 |
| HSA-MIR-320B | 0.2 |
| HSA-MIR-4296 | 0.2 |
| HSA-MIR-3607-3P | 0.2 |
| HSA-MIR-99B | 0.1 |
| HSA-MIR-593* | 0.1 |
| HSA-MIR-425* | 0.1 |
| HSA-MIR-4298 | 0.1 |
| HSA-MIR-3142 | 0.0* |

Example 14—miR-219, miR181 and Other miRNAs are Predicted to Target GSK3β and Other Tau Phosphorylases Materials and Methods Using the TargetScan algorithm as described in Example 2, miRNA families predicted to target tau because of recognition sites on the 3'UTR (Table 6) were tested for potential binding to the 3'UTR of mRNA of other proteins implicated in tauopathies.

Results

As shown in Table 17, miRNA family miR-219-5p/508/508-3p/4782 is predicted to target not only GSK3β, but also other kinases implicated in tauopathy including PKC1, TTBK1, CAMK2G and PKA. As also can be seen from Table 17, miR181abcd14262 miRNA family also targeted GSK3β and other phosphorylases. Other miRNAs including those from miRNA families miR-204/204b/211, miR146ac/146b-5p, miR132/212/212-3p, and miR34ac/34bc-5p/449abc/449c-5p that are also predicted to target tau also are predicted to target these other proteins.

TABLE 17 miRNA Families Predicted to Target Kinases implicated in Tauopathies

| miRNA | GSK3β | PKC1 | TTBK1 | CAMK2G | PKA |
|---|---|---|---|---|---|
| miR-219-5p/508/508-3p/4782-3p | + | + | + | + | + |
| miR-204/204b/211 | + | + | + | + | + |
| miR-181abcd/4262 | + | + | + | + | + |
| miR146ac/146b-5p | − | + | − | − | + |
| miR132/212/212-3p | + | − | − | − | + |
| miR34ac/34bc-5p/449abc/449c-5p | − | − | + | − | + |

Example 15—Additional MicroRNAs Regulate of Tau Expression

Materials and Methods

The same luciferase reporter gene system and cells were used as in Example 4.

The full-length human tau 3' UTR was inserted into a dual-luciferase reporter construct downstream of the *Renilla* luciferase and transiently cotransfected this construct along with six microRNA mirVana mimics (Ambion) that are conserved microRNAs predicted to target the human tau 3'UTR (i.e., miR-219-5p, miR-181-5p, miR-34c-5p, miR-132-3p, miR-27a-5p, and miR-204-5p) into a human neuroblastoma cell line (SH-SY5Y) using FuGene (Promega).

Luciferase activity was assayed after 48 hours (n=8) using the dual-luciferase reporter that controls for transfection efficiency (Promega).

Results

Figure 12:
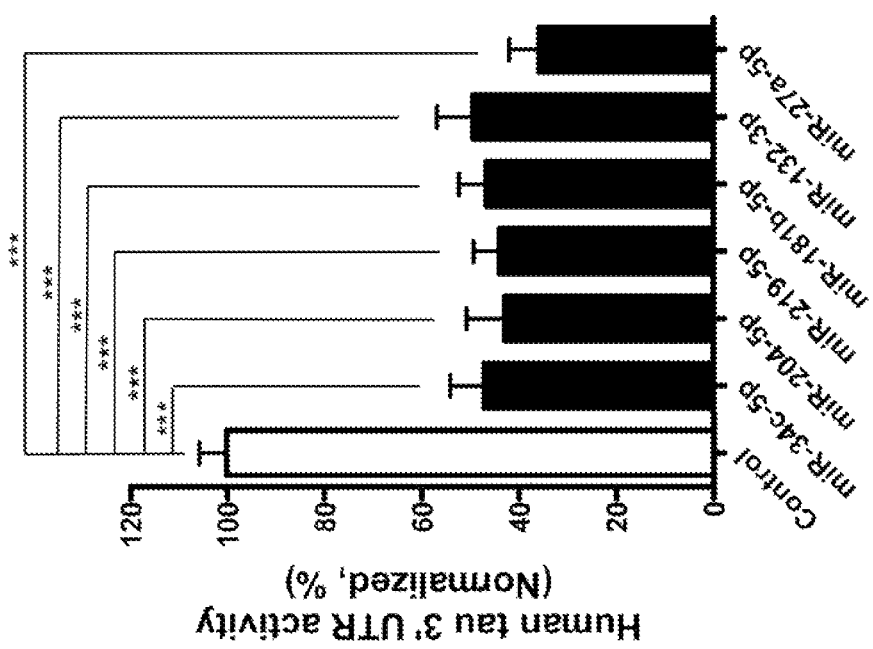
FIG. 12 shows a graph of the luciferase activity of the luciferase reporter construct that contains the entire tau 3' UTR, co-transfected with various microRNAs, compared to control (htau 3' UTR only). (*** p<0.0001).

It was found that along with miR-219-5p and miR-181, mir-34, miR-132, miR-27, and miR-204 are all capable of significantly reducing luciferase activity compared to control (htau 3' UTR only) (FIG. 12). These findings demonstrate that silencing of tau expression by these microRNAs is through direct interaction with the predicted and highly conserved recognition element in the tau 3' UTR.

REFERENCES

Abe and Bonini 2013. *Trends in Cell Biology* 23:30-36.
Ambros 2004. *Nature* 431:350-355.
Anders and Huber 2010. *Genome biology* 11:R106.
Aronov et al. 1999. *Journal of Molecular Neuroscience* 12:131-145.
Aronov et al. 2001. *Journal of Neuroscience* 21:6577-87.
Avila et al. 2004. *Physiological Reviews* 84:361-384.
Baek et al. 2008. *Nature* 455:64-71.
Rancher and Jellinger 1994. *Acta Neuropathol* 88:565-570.
Bartel 2009. *Cell* 136:215-233.
Barton et al. 1990. *The American Journal of Pathology* 137:497-502.
Bejarano et al. 2012. *Development* 139:2821.
Beveridge and Cairns 2012. *Neurobiology of Disease* 46:263-271.
Bilen et al. 2006. *Molecular Cell* 24:157-163.
Binder et al. 1985. *The Journal of Cell Biology* 101:1371-1378.
Borlongan 2012. *Experimental Neurology* 237:142-146.
Brewer et al. 1993. *Journal of Neuroscience Research* 35:567-576.
Bullmann et al. 2007. *Hippocampus* 17:98-102.
Caceres et al. 1991. *The Journal of Neuroscience* 11:1515-1523.
Chin and Goldman 1996. Journal of Neuropathology and Experimental Neurology 55:499-508.
Couratier et al. 1995. *Neurodegeneration* 4:33-41.
Dai et al. 2012. *Current Topics in Developmental Biology* 99:201.
Dawson et al. 2010. *Neuroscience* 169:516-531.
Dickson et al. (2013) *Journal of Neurochemistry* 127:739 (2013).
Dickson 2009. International Journal of Clinical and Experimental Pathology 3:1-23.
Dotti et al. 1987. *Neuroscience* 23:121-130.
Drubin and Hirokawa 1998. *Current Opinion in Cell Biology* 10:13-15.
Drubin et al. 1985. *The Journal of Cell Biology* 101:1799-1807.
Drubin et al. 1988. *The Journal of Cell Biology* 106:1583-1591.
Eacker et al. 2009. *Nature Reviews. Neuroscience* 10:837-841.
Ebert and Sharp 2010. *RNA* 16:2043.
Ebneth et al. 1998. *The Journal of Cell Biology* 143:777-794.
Esclaire et al. 1997. *Journal of Neuroscience Research* 49:309-318.
Eulalio et al. 2008. *Cell* 132:9-14.
Farias et al. 2002. *Journal of Cellular Biochemistry* 85:315-324.
Flynt and Lai 2008. *Nature Reviews. Genetics* 9:831-842.
Follenzi and Naldini 2002. *Methods in Molecular Medicine* 69:259-274.
Friedman et al. 2009. *Genome Research* 19:92-105.
Fulga et al. 2007. *Nature Cell Biology* 9:139-148.
Garcia et al. 2011. *Nature Structural and Molecular Biology* 18:1139-1146.
Gascon and Gao 2012. *Frontiers in Neuroscience* 6:48.
Gasparini et al. 2007. *Neurodegener Dis* 4:236-253.
Gentleman et al. 2004. *Genome Biology* 5:R80.
Gomez-Ramos et al. 2006. *FEBS Letters* 580:4842-4850.
Gong et al. 2005. *Journal of Neural Transmission* 112:813-838.

Grau and Greene 2012. *Methods in Molecular Biology* 846:201-211.
Greene and Tischler 1976. Proceedings of the National Academy of Sciences of the United States of America 73:2424-2428.
Griffiths-Jones 2004. *Nucleic Acids Research* 32:D109-111.
Grimson et al. 2007. *Molecular Cell* 27:91-105.
Guo and Lee 2011. *The Journal of Biological Chemistry* 286:15317-15331.
Hafner et al. 2011. *RNA* 17:1697-1712.
Hamada et al. 2012. *Neurochemistry International* 60:743-750.
Hanemaaijer and Ginzburg 1991. *Journal of Neuroscience Research* 30:163-171.
Hardy 2006. *Journal of Alzheimer's Disease* 9:151-153.
He et al. 2009. *BMC Cell Biology* 10:81.
Hebert et al. 2008. Proceedings of the National Academy of Sciences of the United States of America 105:6415-6420.
Hernandez and Avila 2008. *Journal of Alzheimer's Disease* 14:449-452.
Hebert et al. 2010. *Human Molecular Genetics* 19:3959-3969.
Heidary and Fortini 2001. *Mech Dev* 108:171.
Hong et al. 2010. *Hippocampus* 20:1339-1349.
Hutton et al. 1998. *Nature* 393:702-705.
Jackson et al. 2002. *Neuron* 4(4):509-19.
Jinwal et al. 2013 *Curr Enzym Inhib.* 9(1):41-5.
Kim et al. 2007. *Science* 317:1220-1224.
Kosik 2006. *Nature Reviews. Neuroscience* 7:911-920.
Kotani et al. 1985. *The Journal of Biological Chemistry* 260:10779-10783.
Kozomara and Griffiths-Jones 2011. *Nucleic Acids Research* 39:D152-157.
Kuersten and Goodwin. 2003. *Nature Reviews. Genetics* 4:626-637.
Lau et al. 2013. *EMBO Mol Med* 5:1613.
Le et al. 2012. *American Journal of Neurodegenerative Disease* 1:316-333.
Lee et al. 1993. *Cell* 75:843-854.
Lewis et al. 2005. *Cell* 120:15-20.
Lippens et al. 2012. *Biochemical Society Transactions* 40:698-703.
Litman et al. 1993. *Neuron* 10:627-638.
Loya et al. 2009. *Nature Methods* 6:897.
Maas et al. 2000 *The Journal of Biological Chemistry* 275:15733-15740.
Mandell and Banker 1995. *Neurobiology of Aging* 16:229-238.
Mandelkow and Mandelkow 2012. *Cold Spring Harbor Perspectives in Medicine* 2:a006247.
Maniatis et al. 1982. Molecular Cloning: A Laboratory Manual (*Cold Spring Harbor Laboratory, Cold Spring Harbor, N.Y.*
Matoulkova et al. 2012. *RNA Biology* 9:563-576.
Mazumder et al. 2003. *Trends in Biochemical Sciences* 28:91-98.
Morris et al, 2011. *Neuron* 70:410-426.
Nunez-Iglesias et al. 2010. *PLoS One* 5:e8898.
Packer et al. 2008. *The Journal of Neuroscience* 28:14341-14346.
Perron and Provost 2009. *Methods in Molecular Biology* 487:369-385.
Phelan and Larson 2002. *Journal of the American Geriatrics Society* 50:1306-1308.
Pittman et al. 2006. *Human Molecular Genetics* 15 Spec No 2:R188-195.
Rademakers et al. 2008. *Human Molecular Genetics* 17:3631-3642.
Roberson et al. 2007. *Science* 316:750-754.
Roberson et al. 2011. *The Journal of Neuroscience* 31:700-711.
Rowe and Kahn 1987. *Science* 237:143-149.
Sambrook et al. (1989) *Molecular Cloning: A Laboratory Manual* (*Cold Spring Harbor Laboratory*, 2nd Ed., Cold Spring Harbor, N.Y.
Santa-Maria et al. 2012 (1). *Acta Neuropathologica* 124: 693-704.
Santa-Maria et al. 2012 (2). *The Journal of Biological Chemistry* 287:20522-20533.
Santacruz et al. 2005. *Science* 309:476-481.
Sato et al. 2006 *Journal of Neurochemistry* 98(5):1573-84.
Saugstad 2010. *Journal of Cerebral Blood Flow and Metabolism* 30:1564-1576.
Schaefer et al. 2007. *The Journal of Experimental Medicine* 204:1553-1558.
Schonrock et al. 2012. *Experimental Neurology* 235:447-454.
Schonrock and Gotz 2012. *Cellular and Molecular Life Sciences* 69:3543-3559.
Selbach et al. 2008. *Nature* 455:58-63.
Sempere et al. 2004. *Genome Biology* 5:R13.
Silver et al. 2007. *Proc Natl Acad Sci USA* 104:18151.
Sindou et al. 1992. *Brain Research* 572:242-246.
Spencer et al. 2012. *Frontiers in Genetics* 3:192.
Tashiro et al. 1997. *Neuroreport* 8:2797-2801.
Terwel et al. 2002. *Neuromolecular medicine* 2:151-165.
Thinakaren and Koo 2008.
Trojanowski et al. 1989. *The Journal of Histochemistry and Cytochemistry* 37:209-215.
Ulrich et al. 1992. *Neurodegeneration* 1:257-284.
Vandrovcova et al. 2010. *Current Alzheimer Research* 7:726-734.
Wade-Martins 2012. *Nature Reviews. Neurology* 8:477-478.
Wang et al. 2012. *PLoS One* 7: e42102.
Wang and Mandelkow 2012. 40:644-652.
Wang et al. 2008. *Journal of Neuroscience* 28:1213-1223.
Wang et al. 2010. *Acta Neuropathol* 121:193-205.
Weingarten et al. 1975. Proceedings of the National Academy of Sciences of the United States of America 72:1858-1862.
Williams et al. 2000. *Journal of Comparative Neurology.* 428(4):630-40.
Wittmann et al. 2001. *Science* 293(5530):711-4.
Yamada et al. 2001. *Dement. Geriatr Cogn Disord* 12:117-126
Zhao et al. 2010. *Neuron* 65:612-626.
Zhang and Verbeek 2010. *Journal of Integrative Bioinformatics* 7.

The invention claimed is:

1. A method of treating or preventing a tauopathy comprising administering to a human subject known or suspected of having or being at risk for a tauopathy, a therapeutically effective amount of a composition comprising a microRNA that binds to the 3'UTR of the tau mRNA derived from the microtubule-associated protein tau gene, wherein the microRNA miR-219-5p is at decreased level, and/or the level of miR-181d-5p is at an increased level, in the subject as compared with a control.

2. The method of claim 1, wherein the composition further comprises a ligand, conjugate, vector, lipid, carrier, adjuvant or diluent.

3. The method of claim 1, wherein the composition comprises the microRNA chosen from the group consisting of miR-34c-5p, miR-132-3p, miR-27a-5p, miR-204-5p, miR-485-5p, miR-181b-5p, miR-181d-5p, and miR-219-5p.

4. The method of claim 1, wherein the microRNA comprises the nucleotide sequence of SEQ ID NO: 1, SEQ ID NO: 2, or SEQ ID NO: 3.

5. The method of claim 1, wherein the tauopathy is chosen from the group consisting of Alzheimer's disease, tangle-predominant dementia, progressive supranuclear palsy, chronic traumatic encephalopathy, frontotemporal dementia with Parkinsonism linked to chromosome 17 (FTLD-tau), frontotemporal dementia, ganglioglioma, gangliocytoma, meningioangiomatosis, Pick's disease, and corticobasal degeneration.

6. A method of treating or preventing a tauopathy comprising administering to a human subject known or suspected of having or being at risk for a tauopathy, a therapeutically effective amount of DNA that encodes a microRNA that binds to the 3'UTR of the tau mRNA derived from the microtubule-associated protein tau gene, wherein the microRNA miR-219-5p is at decreased level, and/or the level of miR-181d-5p is at an increased level, in the subject as compared with a control.

7. The method of claim 6, wherein the composition further comprises a ligand, conjugate, vector, lipid, carrier, adjuvant or diluent.

8. The method of claim 6, wherein the composition comprises the microRNA chosen from the group consisting of miR-34c-5p, miR-132-3p, miR-27a-5p, miR-204-5p, miR-485-5p, miR-181b-5p, miR-181d-5p and miR-219-5p.

9. The method of claim 6, wherein the microRNA comprises the nucleotide sequence of SEQ ID NO: 1, SEQ ID NO: 2, or SEQ ID NO: 3.

10. The method of claim 6, wherein the tauopathy is chosen from the group consisting of Alzheimer's disease, tangle-predominant dementia, progressive supranuclear palsy, chronic traumatic encephalopathy, frontotemporal dementia with Parkinsonism linked to chromosome 17 (FTLD-tau), frontotemporal dementia, ganglioglioma, gangliocytoma, meningioangiomatosis, Pick's disease, and corticobasal degeneration.

* * * * *